United States Patent
Griessl

(10) Patent No.: US 11,208,646 B2
(45) Date of Patent: Dec. 28, 2021

(54) ENDOLYSIN VARIANT

(71) Applicant: SASINAPAS CO., LTD., Bangkok (TH)

(72) Inventor: Martin Griessl, Hohenschambach (DE)

(73) Assignee: SASINAPAS CO., LTD., Bangkok (TH)

( * ) Notice: Subject to any disclaimer, the term of this patent is extended or adjusted under 35 U.S.C. 154(b) by 191 days.

(21) Appl. No.: 16/304,355

(22) PCT Filed: May 26, 2017

(86) PCT No.: PCT/IB2017/053099
§ 371 (c)(1),
(2) Date: Nov. 26, 2018

(87) PCT Pub. No.: WO2017/203471
PCT Pub. Date: Nov. 30, 2017

(65) Prior Publication Data
US 2019/0194637 A1     Jun. 27, 2019

(30) Foreign Application Priority Data

May 27, 2016 (WO) ................ PCT/TH2016/000048

(51) Int. Cl.
*C12N 9/80* (2006.01)
*A61P 31/04* (2006.01)

(52) U.S. Cl.
CPC ............ *C12N 9/80* (2013.01); *A61P 31/04* (2018.01)

(58) Field of Classification Search
None
See application file for complete search history.

(56) References Cited

U.S. PATENT DOCUMENTS

2011/0039786 A1* 2/2011 Fujii ............... A61P 15/00
514/17.8

FOREIGN PATENT DOCUMENTS

| WO | WO 2012/059545 A1 | 5/2012 |
| WO | WO 2015/070911 A1 | 5/2015 |
| WO | WO 2015/121443 A1 | 8/2015 |

OTHER PUBLICATIONS

Blast search results for Seq ID No. 10 (retrieved from https://blast.ncbi.nlm.nih.gov/Blast.cgi on Jul. 1, 2020, 40 pages) (Year: 2020).*

(Continued)

*Primary Examiner* — Ronald T Niebauer
(74) *Attorney, Agent, or Firm* — Parker Highlander PLLC

(57) ABSTRACT

The present invention relates to the field of antimicrobial enzymes. In particular, the present invention relates to a polypeptide comprising an amino acid sequence exhibiting at least 90% sequence identity with the sequence of SEQ ID NO:1, with the proviso that the polypeptide does neither comprise the sequence according to SEQ ID NO:2, nor the sequence according to SEQ ID NO:3, nor the sequence according to SEQ ID NO:4. The present invention relates also to nucleic acids encoding an inventive polypeptide, vectors or bacteriophages comprising an inventive nucleic acid as well as host cells comprising an inventive polypeptide, nucleic acid, vector, and/or bacteriophage. Similarly, the present invention relates to compositions comprising a polypeptide, nucleic acid, vector, bacteriophage, and/or host cell according to the present invention.

14 Claims, 1 Drawing Sheet
Specification includes a Sequence Listing.

(56) References Cited

OTHER PUBLICATIONS

Oliveira et al. ('A thermostable *Salmonella* Phage Endolysin, Lys68, with broad bactericidal properties against gram-negative pathogens in presence of weak acids' PLoS One v9(10) Oct. 2014 pp. 1-11) (Year: 2014).*

Oliveira et al. (Supporting info (retrieved from https://journals.plos.org/plosone/article?id=10.1371/journal.pone.0108376) figure S1 for 'A thermostable *Salmonella* Phage Endolysin, Lys68, with broad bactericidal properties against pathogens in presence of weak acids' PLoS One v9(10) Oct. 2014 1 page) (Year: 2014).*

Database UniProt [Online] Feb. 15, 2005.

Database UniProt [Online] Oct. 16, 2013.

Ding, J. L., P. Li, and B. Ho. "The Sushi peptides: structural characterization and mode of action against Gram-negative bacteria." *Cellular and Molecular Life Sciences* 65.7-8 (2008): 1202-1219.

International Search Report and Written Opinion of International Application No. PCT/IB2017/053099, dated Nov. 6, 2017.

Lim, Jeong-A., et al. "Characterization of endolysin from a *Salmonella typhimurium*-infecting bacteriophage SPN1S." *Research in Microbiology* 163.3 (2012): 233-241.

Nelson, Daniel, Lawrence Loomis, and Vincent A. Fischetti. "Prevention and elimination of upper respiratory colonization of mice by group A *Streptococci* by using a bacteriophage lytic enzyme." *Proceedings of the National Academy of Sciences* 98.7 (2001): 4107-4112.

Oliveira, Hugo, et al. "A thermostable *Salmonella* phage endolysin, Lys68, with broad bactericidal properties against gram-negative pathogens in presence of weak acids." *PLoS One* 9.10 (2014): e108376.

Tan, Nguan Soon, et al. "Definition of endotoxin binding sites in horseshoe crab factor C recombinant sushi proteins and neutralization of endotoxin by sushi peptides." *The FASEB Journal* 14.12 (2000): 1801-1813.

Walmagh, Maarten, et al. "Characterization of modular bacteriophage endolysins from Myoviridae phages OBP, 201φ2-1 and PVP-SE1." *PLoS One* 7.5 (2012): e36991.

"Lysozyme [*Salmonella* phage wksl3]", GenBank Accession No. AFO12350.1, dated Mar. 8, 2013, accessed on May 25, 2020.

Kang, Hyun-Wol, et al. "wksl3, a New biocontrol agent for *Salmonella enterica* serovars *enteritidis* and *typhimutium* in foods: characterization, application, sequence analysis, and oral acute toxicity study." *Applied and environmental microbiology* 79.6 (2013): 1956-1968.

* cited by examiner

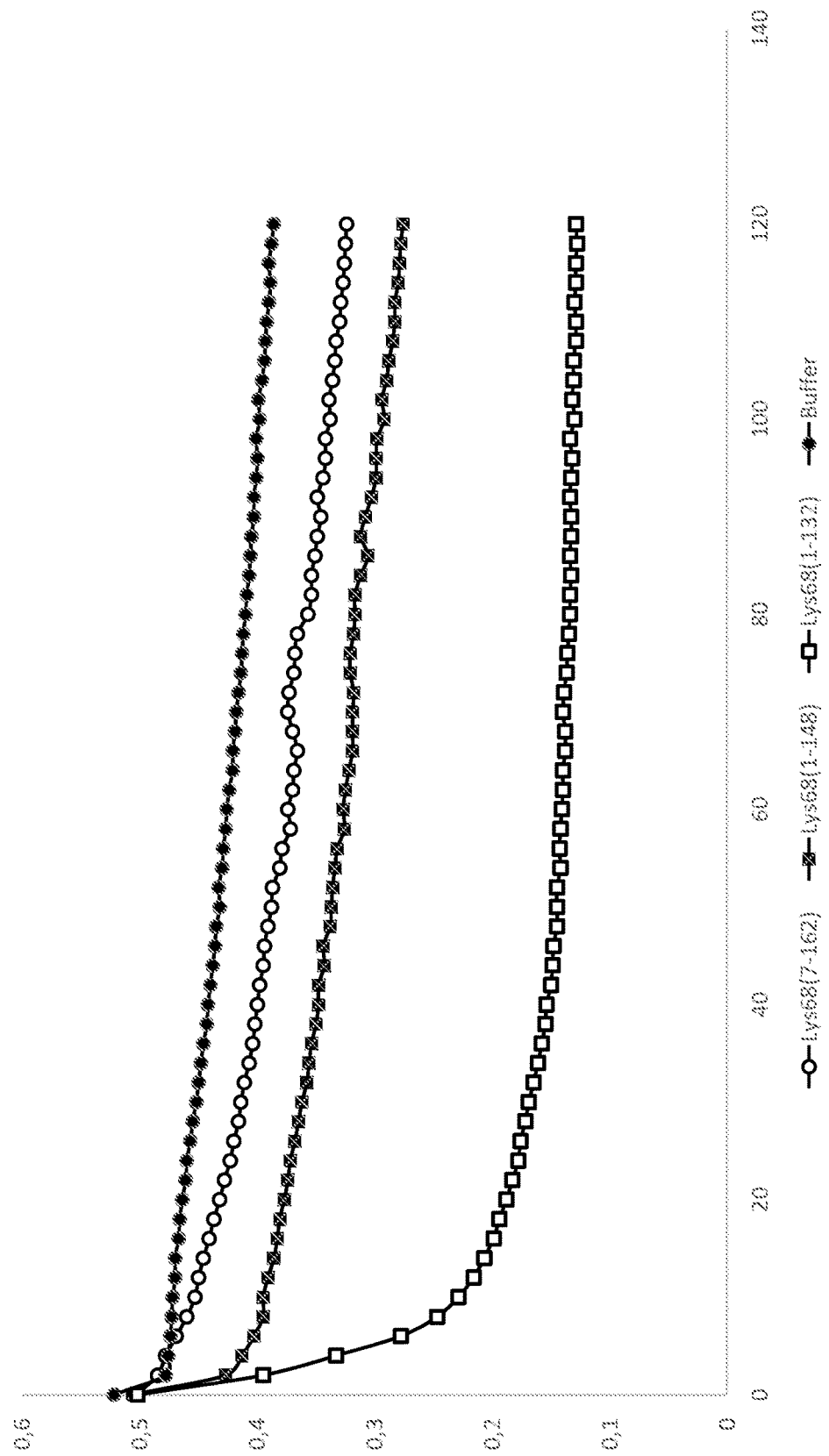

SEQUENCE LISTING

```
<160> NUMBER OF SEQ ID NOS: 120

<210> SEQ ID NO 1
<211> LENGTH: 126
<212> TYPE: PRT
<213> ORGANISM: Artificial sequence
<220> FEATURE:
```

-continued

```
<223> OTHER INFORMATION: Synthetic Consensus Sequence
<220> FEATURE:
<221> NAME/KEY: MISC_FEATURE
<222> LOCATION: (5)..(5)
<223> OTHER INFORMATION: Xaa can be any amino acid, preferably Ile or
      Val
<220> FEATURE:
<221> NAME/KEY: MISC_FEATURE
<222> LOCATION: (13)..(13)
<223> OTHER INFORMATION: Xaa can be any amino acid, preferably Gly or
      Ser
<220> FEATURE:
<221> NAME/KEY: MISC_FEATURE
<222> LOCATION: (72)..(72)
<223> OTHER INFORMATION: Xaa can be any amino acid, preferably Pro, Leu
      or Ser
<220> FEATURE:
<221> NAME/KEY: MISC_FEATURE
<222> LOCATION: (98)..(98)
<223> OTHER INFORMATION: Xaa can be any amino acid, preferably Gly or
      Asp

<400> SEQUENCE: 1

Ser Asp Asn Gly Xaa Lys Phe Thr Ala Ala Phe Glu Xaa Phe Arg Gly
1               5                   10                  15

Thr Ala Tyr Arg Ala Thr Lys Asn Glu Lys Tyr Leu Thr Ile Gly Tyr
            20                  25                  30

Gly His Tyr Gly Ala Asp Val Lys Glu Gly Gln Lys Ile Thr Glu Gly
        35                  40                  45

Gln Gly Leu Leu Leu His Lys Asp Met Val Lys Ala Val Ala Ala
    50                  55                  60

Val Asp Ala Val Ala His Pro Xaa Leu Asn Gln Ser Gln Phe Asp Ala
65                  70                  75                  80

Met Cys Asp Leu Val Tyr Asn Ala Gly Val Gly Val Ile Ala Ala Ser
                85                  90                  95

Thr Xaa Thr Gly Gln Ala Leu Arg Lys Gly Asp Val Ala Thr Leu Arg
            100                 105                 110

Asn Lys Leu Thr Gln Phe His Tyr Gln Asn Gly Lys Ser Leu
        115                 120                 125

<210> SEQ ID NO 2
<211> LENGTH: 162
<212> TYPE: PRT
<213> ORGANISM: Salmonella phage phi68

<400> SEQUENCE: 2

Met Ser Asn Arg Asn Ile Ser Asp Asn Gly Ile Lys Phe Thr Ala Ala
1               5                   10                  15

Phe Glu Gly Phe Arg Gly Thr Ala Tyr Arg Ala Thr Lys Asn Glu Lys
            20                  25                  30

Tyr Leu Thr Ile Gly Tyr Gly His Tyr Gly Ala Asp Val Lys Glu Gly
        35                  40                  45

Gln Lys Ile Thr Glu Gly Gln Gly Leu Leu Leu His Lys Asp Met
    50                  55                  60

Val Lys Ala Val Ala Ala Val Asp Ala Val Ala His Pro Leu Asn
65                  70                  75                  80

Gln Ser Gln Phe Asp Ala Met Cys Asp Leu Val Tyr Asn Ala Gly Val
                85                  90                  95

Gly Val Ile Ala Ala Ser Thr Gly Thr Gly Gln Ala Leu Arg Lys Gly
            100                 105                 110

Asp Val Ala Thr Leu Arg Asn Lys Leu Thr Gln Phe His Tyr Gln Asn
        115                 120                 125
```

```
Gly Lys Ser Leu Leu Gly Leu Arg Arg Arg Ala Ala Gly Arg Val Ala
    130                 135                 140

Leu Phe Asp Gly Met Leu Trp Gln Gln Ala Glu Ala Ile Gly Arg Gly
145                 150                 155                 160

Ala Lys

<210> SEQ ID NO 3
<211> LENGTH: 162
<212> TYPE: PRT
<213> ORGANISM: Artificial sequence
<220> FEATURE:
<223> OTHER INFORMATION: Synthetic Lys68 (T35A)

<400> SEQUENCE: 3

Met Ser Asn Arg Asn Ile Ser Asp Asn Gly Ile Lys Phe Thr Ala Ala
1               5                   10                  15

Phe Glu Gly Phe Arg Gly Thr Ala Tyr Arg Ala Thr Lys Asn Glu Lys
                20                  25                  30

Tyr Leu Ala Ile Gly Tyr Gly His Tyr Gly Ala Asp Val Lys Glu Gly
            35                  40                  45

Gln Lys Ile Thr Glu Gly Gln Gly Leu Leu Leu His Lys Asp Met
    50                  55                  60

Val Lys Ala Val Ala Ala Val Asp Ala Val Ala His Pro Pro Leu Asn
65                  70                  75                  80

Gln Ser Gln Phe Asp Ala Met Cys Asp Leu Val Tyr Asn Ala Gly Val
                85                  90                  95

Gly Val Ile Ala Ala Ser Thr Gly Thr Gly Gln Ala Leu Arg Lys Gly
            100                 105                 110

Asp Val Ala Thr Leu Arg Asn Lys Leu Thr Gln Phe His Tyr Gln Asn
        115                 120                 125

Gly Lys Ser Leu Leu Gly Leu Arg Arg Arg Ala Ala Gly Arg Val Ala
    130                 135                 140

Leu Phe Asp Gly Met Leu Trp Gln Gln Ala Glu Ala Ile Gly Arg Gly
145                 150                 155                 160

Ala Lys

<210> SEQ ID NO 4
<211> LENGTH: 162
<212> TYPE: PRT
<213> ORGANISM: Artificial sequence
<220> FEATURE:
<223> OTHER INFORMATION: Synthetic Lys68 (E18A)

<400> SEQUENCE: 4

Met Ser Asn Arg Asn Ile Ser Asp Asn Gly Ile Lys Phe Thr Ala Ala
1               5                   10                  15

Phe Ala Gly Phe Arg Gly Thr Ala Tyr Arg Ala Thr Lys Asn Glu Lys
                20                  25                  30

Tyr Leu Thr Ile Gly Tyr Gly His Tyr Gly Ala Asp Val Lys Glu Gly
            35                  40                  45

Gln Lys Ile Thr Glu Gly Gln Gly Leu Leu Leu His Lys Asp Met
    50                  55                  60

Val Lys Ala Val Ala Ala Val Asp Ala Val Ala His Pro Pro Leu Asn
65                  70                  75                  80

Gln Ser Gln Phe Asp Ala Met Cys Asp Leu Val Tyr Asn Ala Gly Val
                85                  90                  95
```

```
Gly Val Ile Ala Ala Ser Thr Gly Thr Gly Gln Ala Leu Arg Lys Gly
            100                 105                 110

Asp Val Ala Thr Leu Arg Asn Lys Leu Thr Gln Phe His Tyr Gln Asn
        115                 120                 125

Gly Lys Ser Leu Leu Gly Leu Arg Arg Arg Ala Ala Gly Arg Val Ala
    130                 135                 140

Leu Phe Asp Gly Met Leu Trp Gln Gln Ala Glu Ala Ile Gly Arg Gly
145                 150                 155                 160

Ala Lys

<210> SEQ ID NO 5
<211> LENGTH: 132
<212> TYPE: PRT
<213> ORGANISM: Artificial sequence
<220> FEATURE:
<223> OTHER INFORMATION: Synthetic Consensus sequence
<220> FEATURE:
<221> NAME/KEY: MISC_FEATURE
<222> LOCATION: (1)..(1)
<223> OTHER INFORMATION: Xaa may be absent or any amino acid, in
      particular Met
<220> FEATURE:
<221> NAME/KEY: MISC_FEATURE
<222> LOCATION: (11)..(11)
<223> OTHER INFORMATION: Xaa may be any amino acid, preferably Ile or
      Val
<220> FEATURE:
<221> NAME/KEY: MISC_FEATURE
<222> LOCATION: (19)..(19)
<223> OTHER INFORMATION: Xaa may be any amino acid, preferably Gly or
      Ser
<220> FEATURE:
<221> NAME/KEY: MISC_FEATURE
<222> LOCATION: (78)..(78)
<223> OTHER INFORMATION: Xaa may be any amino acid, preferably Pro, Leu
      or Ser
<220> FEATURE:
<221> NAME/KEY: MISC_FEATURE
<222> LOCATION: (104)..(104)
<223> OTHER INFORMATION: Xaa may be any amino acid, preferably Gly or
      Asp

<400> SEQUENCE: 5

Xaa Ser Asn Arg Asn Ile Ser Asp Asn Gly Xaa Lys Phe Thr Ala Ala
1               5                   10                  15

Phe Glu Xaa Phe Arg Gly Thr Ala Tyr Arg Ala Thr Lys Asn Glu Lys
                20                  25                  30

Tyr Leu Thr Ile Gly Tyr Gly His Tyr Gly Ala Asp Val Lys Glu Gly
            35                  40                  45

Gln Lys Ile Thr Glu Gly Gln Gly Leu Leu Leu Leu His Lys Asp Met
        50                  55                  60

Val Lys Ala Val Ala Val Asp Ala Val Ala His Pro Xaa Leu Asn
65                  70                  75                  80

Gln Ser Gln Phe Asp Ala Met Cys Asp Leu Val Tyr Asn Ala Gly Val
                85                  90                  95

Gly Val Ile Ala Ala Ser Thr Xaa Thr Gly Gln Ala Leu Arg Lys Gly
            100                 105                 110

Asp Val Ala Thr Leu Arg Asn Lys Leu Thr Gln Phe His Tyr Gln Asn
        115                 120                 125

Gly Lys Ser Leu
    130

<210> SEQ ID NO 6
<211> LENGTH: 148
```

```
<212> TYPE: PRT
<213> ORGANISM: Artificial sequence
<220> FEATURE:
<223> OTHER INFORMATION: Synthetic Consensus sequence
<220> FEATURE:
<221> NAME/KEY: MISC_FEATURE
<222> LOCATION: (1)..(1)
<223> OTHER INFORMATION: Xaa may be absent or any amino acid, in
      particular Met
<220> FEATURE:
<221> NAME/KEY: MISC_FEATURE
<222> LOCATION: (11)..(11)
<223> OTHER INFORMATION: Xaa may be any amino acid, preferably Ile or
      Val
<220> FEATURE:
<221> NAME/KEY: MISC_FEATURE
<222> LOCATION: (19)..(19)
<223> OTHER INFORMATION: Xaa may be any amino acid, preferably Gly or
      Ser
<220> FEATURE:
<221> NAME/KEY: MISC_FEATURE
<222> LOCATION: (78)..(78)
<223> OTHER INFORMATION: Xaa may be any amino acid, preferably Pro, Leu
      or Ser
<220> FEATURE:
<221> NAME/KEY: MISC_FEATURE
<222> LOCATION: (104)..(104)
<223> OTHER INFORMATION: Xaa may be any amino acid, preferably Gly or
      Asp
<220> FEATURE:
<221> NAME/KEY: MISC_FEATURE
<222> LOCATION: (134)..(134)
<223> OTHER INFORMATION: Xaa may be any amino acid, preferably Gly or
      Cys

<400> SEQUENCE: 6

Xaa Ser Asn Arg Asn Ile Ser Asp Asn Gly Xaa Lys Phe Thr Ala Ala
1               5                   10                  15

Phe Glu Xaa Phe Arg Gly Thr Ala Tyr Arg Ala Thr Lys Asn Glu Lys
            20                  25                  30

Tyr Leu Thr Ile Gly Tyr Gly His Tyr Gly Ala Asp Val Lys Glu Gly
        35                  40                  45

Gln Lys Ile Thr Glu Gly Gln Gly Leu Leu Leu His Lys Asp Met
    50                  55                  60

Val Lys Ala Val Ala Ala Val Asp Ala Val Ala His Pro Xaa Leu Asn
65                  70                  75                  80

Gln Ser Gln Phe Asp Ala Met Cys Asp Leu Val Tyr Asn Ala Gly Val
                85                  90                  95

Gly Val Ile Ala Ala Ser Thr Xaa Thr Gly Gln Ala Leu Arg Lys Gly
            100                 105                 110

Asp Val Ala Thr Leu Arg Asn Lys Leu Thr Gln Phe His Tyr Gln Asn
            115                 120                 125

Gly Lys Ser Leu Leu Xaa Leu Arg Arg Arg Ala Ala Gly Arg Val Ala
    130                 135                 140

Leu Phe Asp Gly
145

<210> SEQ ID NO 7
<211> LENGTH: 142
<212> TYPE: PRT
<213> ORGANISM: Artificial sequence
<220> FEATURE:
<223> OTHER INFORMATION: Synthetic Consensus sequence
<220> FEATURE:
<221> NAME/KEY: MISC_FEATURE
<222> LOCATION: (5)..(5)
<223> OTHER INFORMATION: Xaa may be any amino acid, preferably Ile or
      Val
```

```
<220> FEATURE:
<221> NAME/KEY: MISC_FEATURE
<222> LOCATION: (13)..(13)
<223> OTHER INFORMATION: Xaa may be any amino acid, preferably Gly or
      Ser
<220> FEATURE:
<221> NAME/KEY: MISC_FEATURE
<222> LOCATION: (72)..(72)
<223> OTHER INFORMATION: Xaa may be any amino acid, preferably Pro, Leu
      or Ser
<220> FEATURE:
<221> NAME/KEY: MISC_FEATURE
<222> LOCATION: (98)..(98)
<223> OTHER INFORMATION: Xaa may be any amino acid, preferably Gly or
      Asp
<220> FEATURE:
<221> NAME/KEY: MISC_FEATURE
<222> LOCATION: (128)..(128)
<223> OTHER INFORMATION: Xaa may be any amino acid, preferably Gly or
      Cys

<400> SEQUENCE: 7

Ser Asp Asn Gly Xaa Lys Phe Thr Ala Ala Phe Glu Xaa Phe Arg Gly
1               5                   10                  15

Thr Ala Tyr Arg Ala Thr Lys Asn Glu Lys Tyr Leu Thr Ile Gly Tyr
            20                  25                  30

Gly His Tyr Gly Ala Asp Val Lys Glu Gly Gln Lys Ile Thr Glu Gly
        35                  40                  45

Gln Gly Leu Leu Leu Leu His Lys Asp Met Val Lys Ala Val Ala Ala
    50                  55                  60

Val Asp Ala Val Ala His Pro Xaa Leu Asn Gln Ser Gln Phe Asp Ala
65                  70                  75                  80

Met Cys Asp Leu Val Tyr Asn Ala Gly Val Gly Val Ile Ala Ala Ser
                85                  90                  95

Thr Xaa Thr Gly Gln Ala Leu Arg Lys Gly Asp Val Ala Thr Leu Arg
            100                 105                 110

Asn Lys Leu Thr Gln Phe His Tyr Gln Asn Gly Lys Ser Leu Leu Xaa
        115                 120                 125

Leu Arg Arg Arg Ala Ala Gly Arg Val Ala Leu Phe Asp Gly
    130                 135                 140

<210> SEQ ID NO 8
<211> LENGTH: 156
<212> TYPE: PRT
<213> ORGANISM: Artificial sequence
<220> FEATURE:
<223> OTHER INFORMATION: Synthetic Consensus sequence
<220> FEATURE:
<221> NAME/KEY: MISC_FEATURE
<222> LOCATION: (5)..(5)
<223> OTHER INFORMATION: Xaa may be any amino acid, preferably Ile or
      Val
<220> FEATURE:
<221> NAME/KEY: MISC_FEATURE
<222> LOCATION: (13)..(13)
<223> OTHER INFORMATION: Xaa may be any amino acid, preferably Gly or
      Ser
<220> FEATURE:
<221> NAME/KEY: MISC_FEATURE
<222> LOCATION: (72)..(72)
<223> OTHER INFORMATION: Xaa may be any amino acid, preferably Pro, Leu
      or Ser
<220> FEATURE:
<221> NAME/KEY: MISC_FEATURE
<222> LOCATION: (98)..(98)
<223> OTHER INFORMATION: Xaa may be any amino acid, preferably Gly or
      Asp
<220> FEATURE:
<221> NAME/KEY: MISC_FEATURE
```

<222> LOCATION: (128)..(128)
<223> OTHER INFORMATION: Xaa may be any amino acid, preferably Gly or
      Cys
<220> FEATURE:
<221> NAME/KEY: MISC_FEATURE
<222> LOCATION: (150)..(150)
<223> OTHER INFORMATION: Xaa may be any amino acid, preferably Ala or
      Val

<400> SEQUENCE: 8

```
Ser Asp Asn Gly Xaa Lys Phe Thr Ala Ala Phe Glu Xaa Phe Arg Gly
1               5                   10                  15

Thr Ala Tyr Arg Ala Thr Lys Asn Glu Lys Tyr Leu Thr Ile Gly Tyr
            20                  25                  30

Gly His Tyr Gly Ala Asp Val Lys Glu Gly Gln Lys Ile Thr Glu Gly
        35                  40                  45

Gln Gly Leu Leu Leu Leu His Lys Asp Met Val Lys Ala Val Ala Ala
    50                  55                  60

Val Asp Ala Val Ala His Pro Xaa Leu Asn Gln Ser Gln Phe Asp Ala
65                  70                  75                  80

Met Cys Asp Leu Val Tyr Asn Ala Gly Val Gly Val Ile Ala Ala Ser
                85                  90                  95

Thr Xaa Thr Gly Gln Ala Leu Arg Lys Gly Asp Val Ala Thr Leu Arg
            100                 105                 110

Asn Lys Leu Thr Gln Phe His Tyr Gln Asn Gly Lys Ser Leu Leu Xaa
        115                 120                 125

Leu Arg Arg Arg Ala Ala Gly Arg Val Ala Leu Phe Asp Gly Met Leu
    130                 135                 140

Trp Gln Gln Ala Glu Xaa Ile Gly Arg Gly Ala Lys
145                 150                 155
```

<210> SEQ ID NO 9
<211> LENGTH: 162
<212> TYPE: PRT
<213> ORGANISM: Artificial Sequence
<220> FEATURE:
<223> OTHER INFORMATION: Synthetic Consensus sequence
<220> FEATURE:
<221> NAME/KEY: MISC_FEATURE
<222> LOCATION: (1)..(1)
<223> OTHER INFORMATION: Xaa may be absent or any amino acid, in
      particular Met
<220> FEATURE:
<221> NAME/KEY: MISC_FEATURE
<222> LOCATION: (11)..(11)
<223> OTHER INFORMATION: Xaa may be any amino acid, preferably Ile or
      Val
<220> FEATURE:
<221> NAME/KEY: MISC_FEATURE
<222> LOCATION: (19)..(19)
<223> OTHER INFORMATION: Xaa may be any amino acid, preferably Gly or
      Ser
<220> FEATURE:
<221> NAME/KEY: MISC_FEATURE
<222> LOCATION: (78)..(78)
<223> OTHER INFORMATION: Xaa may be any amino acid, preferably Pro, Leu
      or Ser
<220> FEATURE:
<221> NAME/KEY: MISC_FEATURE
<222> LOCATION: (104)..(104)
<223> OTHER INFORMATION: Xaa may be any amino acid, preferably Gly or
      Asp
<220> FEATURE:
<221> NAME/KEY: MISC_FEATURE
<222> LOCATION: (134)..(134)
<223> OTHER INFORMATION: Xaa may be any amino acid, preferably Gly or
      Cys
<220> FEATURE:

```
<221> NAME/KEY: MISC_FEATURE
<222> LOCATION: (156)..(156)
<223> OTHER INFORMATION: Xaa may be any amino acid, preferably Ala or
      Val

<400> SEQUENCE: 9

Xaa Ser Asn Arg Asn Ile Ser Asp Asn Gly Xaa Lys Phe Thr Ala Ala
1               5                   10                  15

Phe Glu Xaa Phe Arg Gly Thr Ala Tyr Arg Ala Thr Lys Asn Glu Lys
            20                  25                  30

Tyr Leu Thr Ile Gly Tyr Gly His Tyr Gly Ala Asp Val Lys Glu Gly
        35                  40                  45

Gln Lys Ile Thr Glu Gly Gln Gly Leu Leu Leu His Lys Asp Met
50                  55                  60

Val Lys Ala Val Ala Ala Val Asp Ala Val Ala His Pro Xaa Leu Asn
65                  70                  75                  80

Gln Ser Gln Phe Asp Ala Met Cys Asp Leu Val Tyr Asn Ala Gly Val
                85                  90                  95

Gly Val Ile Ala Ala Ser Thr Xaa Thr Gly Gln Ala Leu Arg Lys Gly
                100                 105                 110

Asp Val Ala Thr Leu Arg Asn Lys Leu Thr Gln Phe His Tyr Gln Asn
            115                 120                 125

Gly Lys Ser Leu Leu Xaa Leu Arg Arg Arg Ala Ala Gly Arg Val Ala
    130                 135                 140

Leu Phe Asp Gly Met Leu Trp Gln Gln Ala Glu Xaa Ile Gly Arg Gly
145                 150                 155                 160

Ala Lys

<210> SEQ ID NO 10
<211> LENGTH: 126
<212> TYPE: PRT
<213> ORGANISM: Artificial sequence
<220> FEATURE:
<223> OTHER INFORMATION: Synthetic Consensus Sequence
<220> FEATURE:
<221> NAME/KEY: MISC_FEATURE
<222> LOCATION: (2)..(2)
<223> OTHER INFORMATION: Xaa can be any amino acid, preferably Asp or
      Asn
<220> FEATURE:
<221> NAME/KEY: MISC_FEATURE
<222> LOCATION: (5)..(5)
<223> OTHER INFORMATION: Xaa can be any amino acid, preferably Leu, Ile
      or Val
<220> FEATURE:
<221> NAME/KEY: MISC_FEATURE
<222> LOCATION: (6)..(6)
<223> OTHER INFORMATION: Xaa can be any amino acid, preferably His or
      Lys
<220> FEATURE:
<221> NAME/KEY: MISC_FEATURE
<222> LOCATION: (13)..(13)
<223> OTHER INFORMATION: Xaa can be any amino acid, preferably Gly, Val
      or Ser
<220> FEATURE:
<221> NAME/KEY: MISC_FEATURE
<222> LOCATION: (15)..(15)
<223> OTHER INFORMATION: Xaa can be any amino acid, preferably Arg or
      Gln
<220> FEATURE:
<221> NAME/KEY: MISC_FEATURE
<222> LOCATION: (20)..(20)
<223> OTHER INFORMATION: Xaa can be any amino acid, preferably Lys or
      Arg
<220> FEATURE:
<221> NAME/KEY: MISC_FEATURE
<222> LOCATION: (23)..(23)
```

```
<223> OTHER INFORMATION: Xaa can be any amino acid, preferably Lys or
      Pro
<220> FEATURE:
<221> NAME/KEY: MISC_FEATURE
<222> LOCATION: (24)..(24)
<223> OTHER INFORMATION: Xaa can be any amino acid, preferably Ser or
      Asn
<220> FEATURE:
<221> NAME/KEY: MISC_FEATURE
<222> LOCATION: (28)..(28)
<223> OTHER INFORMATION: Xaa can be any amino acid, preferably Leu or
      Phe
<220> FEATURE:
<221> NAME/KEY: MISC_FEATURE
<222> LOCATION: (32)..(32)
<223> OTHER INFORMATION: Xaa can be any amino acid, preferably Tyr or
      Phe
<220> FEATURE:
<221> NAME/KEY: MISC_FEATURE
<222> LOCATION: (34)..(34)
<223> OTHER INFORMATION: Xaa can be any amino acid, preferably His or
      Ser
<220> FEATURE:
<221> NAME/KEY: MISC_FEATURE
<222> LOCATION: (37)..(37)
<223> OTHER INFORMATION: Xaa can be any amino acid, preferably Ala or
      Pro
<220> FEATURE:
<221> NAME/KEY: MISC_FEATURE
<222> LOCATION: (38)..(38)
<223> OTHER INFORMATION: Xaa can be any amino acid, preferably Asp or
      His
<220> FEATURE:
<221> NAME/KEY: MISC_FEATURE
<222> LOCATION: (40)..(40)
<223> OTHER INFORMATION: Xaa can be any amino acid, preferably Lys or
      Tyr
<220> FEATURE:
<221> NAME/KEY: MISC_FEATURE
<222> LOCATION: (49)..(49)
<223> OTHER INFORMATION: Xaa can be any amino acid, preferably Gln or
      Arg
<220> FEATURE:
<221> NAME/KEY: MISC_FEATURE
<222> LOCATION: (55)..(55)
<223> OTHER INFORMATION: Xaa can be any amino acid, preferably His or
      Asn
<220> FEATURE:
<221> NAME/KEY: MISC_FEATURE
<222> LOCATION: (56)..(56)
<223> OTHER INFORMATION: Xaa can be any amino acid, preferably Lys or
      Arg
<220> FEATURE:
<221> NAME/KEY: MISC_FEATURE
<222> LOCATION: (59)..(59)
<223> OTHER INFORMATION: Xaa can be any amino acid, preferably Val, Ser
      or Ala
<220> FEATURE:
<221> NAME/KEY: MISC_FEATURE
<222> LOCATION: (72)..(72)
<223> OTHER INFORMATION: Xaa can be any amino acid, preferably Pro, Leu,
      Thr or Ser
<220> FEATURE:
<221> NAME/KEY: MISC_FEATURE
<222> LOCATION: (81)..(81)
<223> OTHER INFORMATION: Xaa can be any amino acid, preferably Met or
      Val
<220> FEATURE:
<221> NAME/KEY: MISC_FEATURE
<222> LOCATION: (90)..(90)
<223> OTHER INFORMATION: Xaa can be any amino acid, preferably Val, Pro
      or Ala
<220> FEATURE:
<221> NAME/KEY: MISC_FEATURE
<222> LOCATION: (95)..(95)
<223> OTHER INFORMATION: Xaa can be any amino acid, preferably Ala or
      Val
<220> FEATURE:
<221> NAME/KEY: MISC_FEATURE
```

```
<222> LOCATION: (98)..(98)
<223> OTHER INFORMATION: Xaa can be any amino acid, preferably Gly or
      Asp
<220> FEATURE:
<221> NAME/KEY: MISC_FEATURE
<222> LOCATION: (108)..(108)
<223> OTHER INFORMATION: Xaa can be any amino acid, preferably Val, Ile
      or Ala
<220> FEATURE:
<221> NAME/KEY: MISC_FEATURE
<222> LOCATION: (109)..(109)
<223> OTHER INFORMATION: Xaa can be any amino acid, preferably Ala or
      Ser
<220> FEATURE:
<221> NAME/KEY: MISC_FEATURE
<222> LOCATION: (113)..(113)
<223> OTHER INFORMATION: Xaa can be any amino acid, preferably Asn or
      Ser
<220> FEATURE:
<221> NAME/KEY: MISC_FEATURE
<222> LOCATION: (116)..(116)
<223> OTHER INFORMATION: Xaa can be any amino acid, preferably Ser or
      Thr

<400> SEQUENCE: 10

Ser Xaa Asn Gly Xaa Xaa Phe Thr Ala Ala Phe Glu Xaa Phe Xaa Gly
1               5                   10                  15

Thr Ala Tyr Xaa Ala Thr Xaa Xaa Glu Lys Tyr Xaa Thr Ile Gly Xaa
            20                  25                  30

Gly Xaa Tyr Gly Xaa Xaa Val Xaa Glu Gly Gln Lys Ile Thr Glu Gly
        35                  40                  45

Xaa Gly Leu Leu Leu Leu Xaa Xaa Asp Met Xaa Lys Ala Val Ala Ala
    50                  55                  60

Val Asp Ala Val Ala His Pro Xaa Leu Asn Gln Ser Gln Phe Asp Ala
65                  70                  75                  80

Xaa Cys Asp Leu Val Tyr Asn Ala Gly Xaa Gly Val Ile Ala Xaa Ser
                85                  90                  95

Thr Xaa Thr Gly Gln Ala Leu Arg Lys Gly Asp Xaa Xaa Thr Leu Arg
        100                 105                 110

Xaa Lys Leu Xaa Gln Phe His Tyr Gln Asn Gly Lys Ser Leu
    115                 120                 125

<210> SEQ ID NO 11
<211> LENGTH: 162
<212> TYPE: PRT
<213> ORGANISM: Salmonella phage wksl3

<400> SEQUENCE: 11

Met Ser Asn Arg Asn Ile Ser Asn Asn Gly Ile Lys Phe Thr Ala Ala
1               5                   10                  15

Phe Glu Gly Phe Arg Gly Thr Ala Tyr Lys Ala Thr Lys Ser Glu Lys
            20                  25                  30

Tyr Leu Thr Ile Gly Tyr Gly His Tyr Gly Ala Asp Val Lys Glu Gly
        35                  40                  45

Gln Lys Ile Thr Glu Gly Gln Gly Leu Leu Leu Leu His Lys Asp Met
    50                  55                  60

Ala Lys Ala Val Ala Ala Val Asp Ala Val Ala His Pro Ser Leu Asn
65                  70                  75                  80

Gln Ser Gln Phe Asp Ala Met Cys Asp Leu Val Tyr Asn Ala Gly Ala
                85                  90                  95

Gly Val Ile Ala Ala Ser Thr Gly Thr Gly Gln Ala Leu Arg Lys Gly
            100                 105                 110
```

Asp Val Ala Thr Leu Arg Asn Lys Leu Ser Gln Phe His Tyr Gln Asn
            115                 120                 125

Gly Lys Ser Leu Pro Trp Met Arg Arg Ala Ala Gly Arg Val Ala
130                 135                 140

Leu Phe Asp Gly Met Pro Trp Gln Gln Ala Glu Ala Ile Gly Arg Glu
145                 150                 155                 160

Ala Lys

<210> SEQ ID NO 12
<211> LENGTH: 162
<212> TYPE: PRT
<213> ORGANISM: Artificial sequence
<220> FEATURE:
<223> OTHER INFORMATION: Synthetic polypeptide (A0A0K1Y7J0;
      UniProtKB/TrEMBL)

<400> SEQUENCE: 12

Met Ser Asn Arg Asn Ile Ser Asn Asn Gly Ile Lys Phe Thr Ala Ala
1               5                   10                  15

Phe Glu Gly Phe Arg Gly Thr Ala Tyr Arg Ala Thr Lys Asn Glu Lys
            20                  25                  30

Tyr Leu Thr Ile Gly Tyr Gly His Tyr Gly Ala Asp Val Lys Glu Gly
        35                  40                  45

Gln Lys Ile Thr Glu Gly Gln Gly Leu Leu Leu His Lys Asp Met
    50                  55                  60

Ala Lys Ala Val Ala Ala Val Asp Ala Val Ala His Pro Ser Leu Asn
65                  70                  75                  80

Gln Ser Gln Phe Asp Ala Val Cys Asp Leu Val Tyr Asn Ala Gly Ala
                85                  90                  95

Gly Val Ile Ala Ala Ser Thr Gly Thr Gly Gln Ala Leu Arg Lys Gly
            100                 105                 110

Asp Val Ala Thr Leu Arg Asn Lys Leu Thr Gln Phe His Tyr Gln Asn
            115                 120                 125

Gly Lys Ser Leu Leu Gly Leu Arg Arg Ala Ala Gly Arg Val Ala
    130                 135                 140

Leu Phe Asp Gly Met Leu Trp Gln Gln Ala Glu Ala Ile Gly Arg Gly
145                 150                 155                 160

Ala Lys

<210> SEQ ID NO 13
<211> LENGTH: 162
<212> TYPE: PRT
<213> ORGANISM: Salmonella phage SS3e

<400> SEQUENCE: 13

Met Ser Asn Arg Asn Ile Ser Asn Asn Gly Ile Lys Phe Thr Ala Ala
1               5                   10                  15

Phe Glu Gly Phe Arg Gly Thr Ala Tyr Arg Ala Thr Lys Asn Glu Lys
            20                  25                  30

Tyr Leu Thr Ile Gly Tyr Gly His Tyr Gly Ala Asp Val Lys Glu Gly
        35                  40                  45

Gln Lys Ile Thr Glu Gly Gln Gly Leu Leu Leu His Lys Asp Met
    50                  55                  60

Ala Lys Ala Val Ala Ala Val Asp Ala Val Ala His Pro Ser Leu Asn
65                  70                  75                  80

Gln Ser Gln Phe Asp Ala Met Cys Asp Leu Val Tyr Asn Ala Gly Ala
                85                  90                  95

Gly Val Ile Ala Ala Ser Thr Gly Thr Gly Gln Ala Leu Arg Lys Gly
                100                 105                 110

Asp Val Ala Thr Leu Arg Asn Lys Leu Ser Gln Phe His Tyr Gln Asn
            115                 120                 125

Gly Lys Ser Leu Leu Gly Leu Arg Arg Arg Ala Ala Gly Arg Val Ala
    130                 135                 140

Leu Phe Asp Gly Met Leu Trp Gln Gln Ala Glu Ala Ile Gly Arg Glu
145                 150                 155                 160

Ala Lys

<210> SEQ ID NO 14
<211> LENGTH: 160
<212> TYPE: PRT
<213> ORGANISM: Salmonella phage vB_SenS_AG11

<400> SEQUENCE: 14

Met Arg Asn Ile Ser Asn Asn Gly Ile Lys Phe Thr Ala Ala Phe Glu
1               5                   10                  15

Gly Phe Arg Gly Thr Ala Tyr Arg Ala Thr Lys Asn Glu Lys Tyr Leu
            20                  25                  30

Thr Ile Gly Tyr Gly His Tyr Gly Ala Asp Val Lys Glu Gly Gln Lys
        35                  40                  45

Ile Thr Glu Gly Gln Gly Leu Leu Leu His Lys Asp Met Ala Lys
    50                  55                  60

Ala Val Ala Ala Val Asp Ala Val Ala His Pro Ser Leu Asn Gln Ser
65                  70                  75                  80

Gln Phe Asp Ala Met Cys Asp Leu Val Tyr Asn Ala Gly Ala Gly Val
                85                  90                  95

Ile Ala Ala Ser Thr Gly Thr Gly Gln Ala Leu Arg Lys Gly Asp Val
                100                 105                 110

Ala Thr Leu Arg Ser Lys Leu Thr Gln Phe His Tyr Gln Asn Gly Lys
            115                 120                 125

Ser Leu Leu Gly Leu Arg Arg Arg Ala Ala Gly Arg Val Ala Leu Phe
    130                 135                 140

Asp Gly Met Leu Trp Gln Gln Ala Glu Ala Ile Gly Arg Glu Ala Lys
145                 150                 155                 160

<210> SEQ ID NO 15
<211> LENGTH: 162
<212> TYPE: PRT
<213> ORGANISM: Salmonella phage BPS11Q3

<400> SEQUENCE: 15

Met Ser Asn Arg Asn Ile Ser Asn Asn Gly Ile Lys Phe Thr Ala Ala
1               5                   10                  15

Phe Glu Gly Phe Arg Gly Thr Ala Tyr Lys Ala Thr Lys Asn Glu Lys
            20                  25                  30

Tyr Phe Thr Ile Gly Tyr Gly His Tyr Gly Ala Asp Val Lys Glu Gly
        35                  40                  45

Gln Lys Ile Thr Glu Gly Gln Gly Leu Leu Leu His Lys Asp Met
    50                  55                  60

Ala Lys Ala Val Ala Ala Val Asp Ala Val Ala His Pro Thr Leu Asn
65                  70                  75                  80

Gln Ser Gln Phe Asp Ala Met Cys Asp Leu Val Tyr Asn Ala Gly Ala
                85                  90                  95

```
Gly Val Ile Ala Ala Ser Thr Gly Thr Gly Gln Ala Leu Arg Lys Gly
            100                 105                 110

Asp Val Ala Thr Leu Arg Asn Lys Leu Thr Gln Phe His Tyr Gln Asn
        115                 120                 125

Gly Lys Ser Leu Leu Gly Leu Arg Arg Arg Ala Ala Gly Arg Val Ala
    130                 135                 140

Leu Phe Asp Gly Met Leu Trp Gln Gln Ala Glu Ala Ile Gly Arg Gly
145                 150                 155                 160

Ala Lys

<210> SEQ ID NO 16
<211> LENGTH: 162
<212> TYPE: PRT
<213> ORGANISM: Salmonella enterica

<400> SEQUENCE: 16

Met Ser Asn Arg Asn Ile Ser Asp Asn Gly Leu His Phe Thr Ala Ala
1               5                   10                  15

Phe Glu Gly Phe Arg Gly Thr Ala Tyr Lys Ala Thr Lys Asn Glu Lys
            20                  25                  30

Tyr Leu Thr Ile Gly Tyr Gly His Tyr Gly Ala Asp Val Lys Glu Gly
        35                  40                  45

Gln Lys Ile Thr Glu Gly Gln Gly Leu Leu Leu His Lys Asp Met
    50                  55                  60

Ala Lys Ala Val Ala Ala Val Asp Ala Val Ala His Pro Ser Leu Asn
65                  70                  75                  80

Gln Ser Gln Phe Asp Ala Met Cys Asp Leu Val Tyr Asn Ala Gly Ala
                85                  90                  95

Gly Val Ile Ala Ala Ser Thr Gly Thr Gly Gln Ala Leu Arg Lys Gly
            100                 105                 110

Asp Val Ala Thr Leu Arg Asn Lys Leu Thr Gln Phe His Tyr Gln Asn
        115                 120                 125

Gly Lys Ser Leu Leu Gly Leu Arg Arg Arg Ala Ala Gly Arg Val Ala
    130                 135                 140

Leu Phe Asp Gly Met Leu Trp Gln Gln Ala Glu Ala Ile Gly Arg Glu
145                 150                 155                 160

Ala Lys

<210> SEQ ID NO 17
<211> LENGTH: 162
<212> TYPE: PRT
<213> ORGANISM: Salmonella enterica

<400> SEQUENCE: 17

Met Thr Asn Arg Asn Ile Ser Asp Asn Gly Leu His Phe Thr Ala Ala
1               5                   10                  15

Phe Glu Gly Phe Arg Gly Thr Ala Tyr Lys Ala Thr Lys Asn Glu Lys
            20                  25                  30

Tyr Leu Thr Ile Gly Tyr Gly His Tyr Gly Ala Asp Val Lys Glu Gly
        35                  40                  45

Gln Lys Ile Thr Glu Gly Gln Gly Leu Leu Leu His Lys Asp Met
    50                  55                  60

Ala Lys Ala Val Ala Ala Val Asp Ala Val Ala His Pro Ser Leu Asn
65                  70                  75                  80

Gln Ser Gln Phe Asp Ala Met Cys Asp Leu Val Tyr Asn Ala Gly Ala
                85                  90                  95
```

```
Gly Val Ile Ala Ala Ser Thr Gly Thr Gly Gln Ala Leu Arg Lys Gly
                100                 105                 110

Asp Val Ala Thr Leu Arg Asn Lys Leu Thr Gln Phe His Tyr Gln Asn
            115                 120                 125

Gly Lys Ser Leu Leu Gly Leu Arg Arg Arg Ala Ala Gly Arg Val Ala
        130                 135                 140

Leu Phe Asp Gly Met Leu Trp Gln Gln Ala Glu Ala Ile Gly Arg Glu
145                 150                 155                 160

Ala Lys

<210> SEQ ID NO 18
<211> LENGTH: 162
<212> TYPE: PRT
<213> ORGANISM: Salmonella phage SE2

<400> SEQUENCE: 18

Met Ser Asn Arg Asn Ile Ser Asp Asn Gly Leu His Phe Thr Ala Ala
1               5                   10                  15

Phe Glu Gly Phe Arg Gly Thr Ala Tyr Lys Ala Thr Lys Asn Glu Lys
                20                  25                  30

Tyr Leu Thr Ile Gly Tyr Gly His Tyr Gly Ala Asp Val Lys Glu Gly
            35                  40                  45

Gln Lys Ile Thr Glu Gly Gln Gly Leu Leu Leu His Lys Asp Met
        50                  55                  60

Ala Lys Ala Val Ala Ala Val Asp Ala Val Ala His Pro Thr Leu Asn
65                  70                  75                  80

Gln Ser Gln Phe Asp Ala Met Cys Asp Leu Val Tyr Asn Ala Gly Ala
                85                  90                  95

Gly Val Ile Ala Ala Ser Thr Gly Thr Gly Gln Ala Leu Arg Lys Gly
                100                 105                 110

Asp Val Ala Thr Leu Arg Asn Lys Leu Thr Gln Phe His Tyr Gln Asn
            115                 120                 125

Gly Lys Ser Leu Leu Gly Leu Arg Arg Arg Ala Ala Gly Arg Val Ala
        130                 135                 140

Leu Phe Asp Gly Met Leu Trp Gln Gln Ala Glu Ala Ile Gly Arg Gly
145                 150                 155                 160

Ala Lys

<210> SEQ ID NO 19
<211> LENGTH: 162
<212> TYPE: PRT
<213> ORGANISM: Salmonella phage ST4

<400> SEQUENCE: 19

Met Ser Asn Arg Asn Ile Ser Asn Asn Gly Ile Lys Phe Thr Ala Ala
1               5                   10                  15

Phe Glu Gly Phe Arg Gly Thr Ala Tyr Lys Ala Thr Lys Asn Glu Lys
                20                  25                  30

Tyr Phe Thr Ile Gly Tyr Gly His Tyr Gly Ala Asp Val Lys Glu Gly
            35                  40                  45

Gln Lys Ile Thr Glu Gly Gln Gly Leu Leu Leu His Lys Asp Met
        50                  55                  60

Ser Lys Ala Val Ala Ala Val Asp Ala Val Ala His Pro Ser Leu Asn
65                  70                  75                  80

Gln Ser Gln Phe Asp Ala Val Cys Asp Leu Val Tyr Asn Ala Gly Pro
```

```
                    85                  90                  95

Gly Val Ile Ala Ala Ser Thr Gly Thr Gly Gln Ala Leu Arg Lys Gly
                   100                 105                 110

Asp Val Ala Thr Leu Arg Asn Lys Leu Thr Gln Phe His Tyr Gln Asn
                   115                 120                 125

Gly Lys Ser Leu Leu Gly Leu Arg Arg Arg Ala Ala Gly Arg Val Ala
            130                 135                 140

Leu Phe Asp Gly Met Leu Trp Gln Gln Ala Glu Ala Ile Gly Arg Glu
145                 150                 155                 160

Ala Lys

<210> SEQ ID NO 20
<211> LENGTH: 160
<212> TYPE: PRT
<213> ORGANISM: Salmonella enterica

<400> SEQUENCE: 20

Met Arg Asn Ile Ser Asn Asn Gly Ile Lys Phe Thr Ala Ala Phe Glu
1               5                   10                  15

Gly Phe Arg Gly Thr Ala Tyr Arg Ala Thr Lys Asn Glu Lys Tyr Leu
                20                  25                  30

Thr Ile Gly Tyr Gly His Tyr Gly Ala Asp Val Lys Glu Gly Gln Lys
            35                  40                  45

Ile Thr Glu Gly Gln Gly Leu Leu Leu Asn Arg Asp Met Ala Lys
        50                  55                  60

Ala Val Ala Ala Val Asp Ala Val Ala His Pro Ser Leu Asn Gln Ser
65                  70                  75                  80

Gln Phe Asp Ala Val Cys Asp Leu Val Tyr Asn Ala Gly Ala Gly Val
                85                  90                  95

Ile Ala Ala Ser Thr Gly Thr Gly Gln Ala Leu Arg Lys Gly Asp Val
                   100                 105                 110

Ala Thr Leu Arg Asn Lys Leu Thr Gln Phe His Tyr Gln Asn Gly Lys
                   115                 120                 125

Ser Leu Leu Gly Leu Arg Arg Arg Ala Ala Gly Arg Val Ala Leu Phe
            130                 135                 140

Asp Gly Met Leu Trp Gln Gln Ala Glu Ala Ile Gly Arg Glu Ala Lys
145                 150                 155                 160

<210> SEQ ID NO 21
<211> LENGTH: 162
<212> TYPE: PRT
<213> ORGANISM: Salmonella phage FSL SP-101

<400> SEQUENCE: 21

Met Ser Asn Arg Asn Ile Ser Asp Asn Gly Leu Lys Phe Thr Ala Ala
1               5                   10                  15

Phe Glu Gly Phe Arg Gly Thr Ala Tyr Lys Ala Thr Lys Asn Glu Lys
                20                  25                  30

Tyr Leu Thr Ile Gly Phe Gly His Tyr Gly Ala Asp Val Lys Glu Gly
            35                  40                  45

Gln Lys Ile Thr Glu Gly Arg Gly Leu Leu Leu His Lys Asp Met
        50                  55                  60

Ala Lys Ala Val Ala Ala Val Asp Ala Val Ala His Pro Ser Leu Asn
65                  70                  75                  80

Gln Ser Gln Phe Asp Ala Val Cys Asp Leu Val Tyr Asn Ala Gly Ala
                85                  90                  95
```

```
Gly Val Ile Ala Ala Ser Thr Gly Thr Gly Gln Ala Leu Arg Lys Gly
            100                 105                 110

Asp Ile Ala Thr Leu Arg Asn Lys Leu Thr Gln Phe His Tyr Gln Asn
            115                 120                 125

Gly Lys Ser Leu Leu Gly Leu Arg Arg Arg Ala Ala Gly Arg Val Ala
        130                 135                 140

Leu Phe Asp Gly Met Leu Trp Gln Gln Ala Glu Ala Val Gly Arg Ala
145                 150                 155                 160

Ala Lys

<210> SEQ ID NO 22
<211> LENGTH: 162
<212> TYPE: PRT
<213> ORGANISM: Salmonella phage vB_SenS-Ent2

<400> SEQUENCE: 22

Met Ser Asn Arg Asn Ile Ser Asn Asn Gly Leu Lys Phe Thr Ala Ala
1               5                   10                  15

Phe Glu Gly Phe Gln Gly Thr Ala Tyr Arg Ala Thr Lys Asn Glu Lys
            20                  25                  30

Tyr Phe Thr Ile Gly Tyr Gly His Tyr Gly Ala Asp Val Lys Glu Gly
        35                  40                  45

Gln Lys Ile Thr Glu Gly Gln Gly Leu Leu Leu His Lys Asp Met
    50                  55                  60

Ala Lys Ala Val Ala Val Asp Ala Val Ala His Pro Ser Leu Asn
65                  70                  75                  80

Gln Ser Gln Phe Asp Ala Val Cys Asp Leu Val Tyr Asn Ala Gly Ala
                85                  90                  95

Gly Val Ile Ala Ala Ser Thr Gly Thr Gly Gln Ala Leu Arg Lys Gly
            100                 105                 110

Asp Val Ala Thr Leu Arg Asn Lys Leu Thr Gln Phe His Tyr Gln Asn
            115                 120                 125

Gly Lys Ser Leu Leu Gly Leu Arg Arg Arg Ala Ala Gly Arg Val Ala
        130                 135                 140

Leu Phe Asp Gly Met Leu Trp Gln Gln Ala Glu Ala Val Gly Arg Glu
145                 150                 155                 160

Ala Lys

<210> SEQ ID NO 23
<211> LENGTH: 162
<212> TYPE: PRT
<213> ORGANISM: Salmonella phage SETP3

<400> SEQUENCE: 23

Met Ser Asn Arg Asn Ile Ser Asn Asn Gly Ile Lys Phe Thr Ala Ala
1               5                   10                  15

Phe Glu Gly Phe Arg Gly Thr Ala Tyr Lys Ala Thr Lys Asn Glu Lys
            20                  25                  30

Tyr Phe Thr Ile Gly Tyr Gly His Tyr Gly Ala Asp Val Lys Glu Gly
        35                  40                  45

Gln Lys Ile Thr Glu Gly Gln Gly Leu Leu Leu His Lys Asp Met
    50                  55                  60

Ala Lys Ala Val Ala Val Asp Ala Val Ala His Pro Ser Leu Asn
65                  70                  75                  80

Gln Ser Gln Phe Asp Ala Val Cys Asp Leu Val Tyr Asn Ala Gly Ala
```

```
                    85                  90                  95
Gly Val Ile Ala Ala Ser Thr Gly Thr Gly Gln Ala Leu Arg Lys Gly
                100                 105                 110

Asp Ala Ser Thr Leu Arg Asn Lys Leu Thr Gln Phe His Tyr Gln Asn
            115                 120                 125

Gly Lys Ser Leu Leu Gly Leu Arg Arg Arg Ala Ala Gly Arg Val Ala
        130                 135                 140

Leu Phe Asp Gly Met Leu Trp Gln Gln Ala Glu Ala Val Gly Arg Ala
145                 150                 155                 160

Ala Lys

<210> SEQ ID NO 24
<211> LENGTH: 162
<212> TYPE: PRT
<213> ORGANISM: Salmonella phage Jersey

<400> SEQUENCE: 24

Met Ser Asn Arg Asn Ile Ser Asp Asn Gly Leu His Phe Thr Ala Ala
1               5                   10                  15

Phe Glu Gly Phe Arg Gly Thr Ala Tyr Lys Ala Thr Lys Ser Glu Lys
            20                  25                  30

Tyr Leu Thr Ile Gly Tyr Gly His Tyr Gly Ala Asp Val Lys Glu Gly
        35                  40                  45

Gln Lys Ile Thr Glu Gly Arg Gly Leu Leu Leu His Lys Asp Met
    50                  55                  60

Ser Lys Ala Val Ala Val Asp Ala Val Ala His Pro Ser Leu Asn
65                  70                  75                  80

Gln Ser Gln Phe Asp Ala Val Cys Asp Leu Val Tyr Asn Ala Gly Ala
                85                  90                  95

Gly Val Ile Ala Ala Ser Thr Gly Thr Gly Gln Ala Leu Arg Lys Gly
                100                 105                 110

Asp Val Ala Thr Leu Arg Asn Lys Leu Ser Gln Phe His Tyr Gln Asn
            115                 120                 125

Gly Lys Ser Leu Leu Gly Leu Arg Arg Arg Ala Val Gly Arg Val Ala
        130                 135                 140

Leu Phe Asp Gly Met Leu Trp Gln Gln Ala Glu Ala Val Gly Arg Ala
145                 150                 155                 160

Thr Lys

<210> SEQ ID NO 25
<211> LENGTH: 160
<212> TYPE: PRT
<213> ORGANISM: Salmonella phage SETP13

<400> SEQUENCE: 25

Met Arg Asn Ile Ser Asn Asn Gly Ile Lys Phe Thr Ala Ala Phe Glu
1               5                   10                  15

Gly Phe Arg Gly Thr Ala Tyr Arg Ala Thr Lys Asn Glu Lys Tyr Leu
            20                  25                  30

Thr Ile Gly Tyr Gly Ser Tyr Gly Pro His Val Lys Glu Gly Gln Lys
        35                  40                  45

Ile Thr Glu Gly Gln Gly Leu Leu Leu His Lys Asp Met Ala Lys
    50                  55                  60

Ala Val Ala Ala Val Asp Ala Val Ala His Pro Ser Leu Asn Gln Ser
65                  70                  75                  80
```

```
Gln Phe Asp Ala Val Cys Asp Leu Val Tyr Asn Ala Gly Ala Gly Val
                85                  90                  95

Ile Ala Ala Ser Thr Gly Thr Gly Gln Ala Leu Arg Lys Gly Asp Val
            100                 105                 110

Ala Thr Leu Arg Asn Lys Leu Thr Gln Phe His Tyr Gln Asn Gly Lys
        115                 120                 125

Ser Leu Leu Gly Leu Arg Arg Arg Ala Ala Gly Arg Val Ala Leu Phe
    130                 135                 140

Asp Gly Met Leu Trp Gln Gln Ala Glu Ala Ile Ser Arg Gly Ala Lys
145                 150                 155                 160

<210> SEQ ID NO 26
<211> LENGTH: 160
<212> TYPE: PRT
<213> ORGANISM: Salmonella phage SETP7

<400> SEQUENCE: 26

Met Arg Asn Ile Ser Asn Asn Gly Ile Lys Phe Thr Ala Ala Phe Glu
1               5                   10                  15

Gly Phe Arg Gly Thr Ala Tyr Arg Ala Thr Lys Asn Glu Lys Tyr Leu
            20                  25                  30

Thr Ile Gly Tyr Gly Ser Tyr Gly Pro His Val Lys Glu Gly Gln Lys
        35                  40                  45

Ile Thr Glu Gly Gln Gly Leu Leu Leu His Lys Asp Met Ala Lys
    50                  55                  60

Ala Val Ala Ala Val Asp Ala Val Ala His Pro Ser Leu Asn Gln Ser
65                  70                  75                  80

Gln Phe Asp Ala Val Cys Asp Leu Val Tyr Asn Ala Gly Ala Gly Val
                85                  90                  95

Ile Ala Ala Ser Thr Gly Thr Gly Gln Ala Leu Arg Lys Gly Asp Val
            100                 105                 110

Ala Thr Leu Arg Asn Lys Leu Thr Gln Phe His Tyr Gln Asn Gly Lys
        115                 120                 125

Ser Leu Leu Gly Leu Arg Arg Arg Ala Ala Gly Arg Val Ala Leu Phe
    130                 135                 140

Asp Gly Met Leu Trp Gln Gln Ala Glu Ala Ile Gly Arg Gly Ala Lys
145                 150                 155                 160

<210> SEQ ID NO 27
<211> LENGTH: 160
<212> TYPE: PRT
<213> ORGANISM: Salmonella phage STP03

<400> SEQUENCE: 27

Met Arg Asn Ile Ser Asn Asn Gly Ile Lys Phe Thr Ala Ala Phe Glu
1               5                   10                  15

Val Phe Arg Gly Thr Ala Tyr Arg Ala Thr Lys Asn Glu Lys Tyr Leu
            20                  25                  30

Thr Ile Gly Tyr Gly His Tyr Gly Ala Asp Val Lys Glu Gly Gln Lys
        35                  40                  45

Ile Thr Glu Gly Gln Gly Leu Leu Leu Leu Asn Arg Asp Met Ala Lys
    50                  55                  60

Ala Val Ala Ala Val Asp Ala Val Ala His Pro Ser Leu Asn Gln Ser
65                  70                  75                  80

Gln Phe Asp Ala Val Cys Asp Leu Val Tyr Asn Ala Gly Ala Gly Val
                85                  90                  95
```

Ile Ala Ala Ser Thr Gly Thr Gly Gln Ala Leu Arg Lys Gly Asp Ala
        100                 105                 110

Ser Thr Leu Arg Asn Lys Leu Thr Gln Phe His Tyr Gln Asn Gly Lys
    115                 120                 125

Ser Leu Leu Gly Leu Arg Arg Arg Ala Ala Gly Arg Val Ala Leu Phe
    130                 135                 140

Asp Gly Met Leu Trp Gln Gln Ala Glu Ala Val Gly Arg Ala Ala Lys
145                 150                 155                 160

<210> SEQ ID NO 28
<211> LENGTH: 162
<212> TYPE: PRT
<213> ORGANISM: Salmonella phage Ent1

<400> SEQUENCE: 28

Met Ser Asn Arg Asn Ile Ser Asn Asn Gly Leu Lys Phe Thr Ala Ala
1               5                   10                  15

Phe Glu Gly Phe Arg Gly Thr Ala Tyr Lys Ala Thr Lys Asn Glu Lys
            20                  25                  30

Tyr Leu Thr Ile Gly Tyr Gly Ser Tyr Gly Pro His Val Lys Glu Gly
        35                  40                  45

Gln Lys Ile Thr Glu Gly Gln Gly Leu Leu Leu Leu His Lys Asp Met
    50                  55                  60

Ala Lys Ala Val Ala Ala Val Asp Ala Val Ala His Pro Ser Leu Asn
65                  70                  75                  80

Gln Ser Gln Phe Asp Ala Val Cys Asp Leu Val Tyr Asn Ala Gly Ala
                85                  90                  95

Gly Val Ile Ala Ala Ser Thr Gly Thr Gly Gln Ala Leu Arg Lys Gly
            100                 105                 110

Asp Val Ala Thr Leu Arg Asn Lys Leu Thr Gln Phe His Tyr Gln Asn
        115                 120                 125

Gly Lys Ser Leu Leu Gly Leu Arg Arg Arg Ala Ala Gly Arg Val Ala
    130                 135                 140

Leu Phe Asp Gly Met Leu Trp Gln Gln Ala Glu Ala Ile Gly Arg Gly
145                 150                 155                 160

Ala Lys

<210> SEQ ID NO 29
<211> LENGTH: 162
<212> TYPE: PRT
<213> ORGANISM: Salmonella phage LPSE1

<400> SEQUENCE: 29

Met Ser Asn Arg Asn Ile Ser Asp Asn Gly Leu His Phe Thr Ala Ala
1               5                   10                  15

Phe Glu Gly Phe Arg Gly Thr Ala Tyr Arg Ala Thr Pro Ser Glu Lys
            20                  25                  30

Tyr Phe Thr Ile Gly Tyr Gly His Tyr Gly Ala Asp Val Lys Glu Gly
        35                  40                  45

Gln Lys Ile Thr Glu Gly Gln Gly Leu Leu Leu Leu His Lys Asp Met
    50                  55                  60

Ala Lys Ala Val Ala Ala Val Asp Ala Val Ala His Pro Ser Leu Asn
65                  70                  75                  80

Gln Ser Gln Phe Asp Ala Val Cys Asp Leu Val Tyr Asn Ala Gly Ala
                85                  90                  95

Gly Val Ile Ala Val Ser Thr Gly Thr Gly Gln Ala Leu Arg Lys Gly

```
                    100                 105                 110

Asp Ala Ser Thr Leu Arg Asn Lys Leu Thr Gln Phe His Tyr Gln Asn
            115                 120                 125

Gly Lys Ser Leu Leu Gly Leu Arg Arg Arg Ala Ala Gly Arg Val Ala
        130                 135                 140

Leu Phe Asp Gly Met Leu Trp Gln Gln Ala Glu Ala Val Gly Arg Asp
145                 150                 155                 160

Ala Lys

<210> SEQ ID NO 30
<211> LENGTH: 162
<212> TYPE: PRT
<213> ORGANISM: Salmonella phage MA12

<400> SEQUENCE: 30

Met Ser Asn Arg Asn Ile Ser Asn Asn Gly Ile Lys Phe Thr Ala Ala
1               5                   10                  15

Phe Glu Gly Phe Arg Gly Thr Ala Tyr Lys Ala Thr Lys Asn Glu Lys
            20                  25                  30

Tyr Phe Thr Ile Gly Tyr Gly Ser Tyr Gly Pro His Val Lys Glu Gly
        35                  40                  45

Gln Lys Ile Thr Glu Gly Gln Gly Leu Leu Leu His Lys Asp Met
    50                  55                  60

Ala Lys Ala Val Ala Ala Val Asp Ala Val Ala His Pro Ser Leu Asn
65                  70                  75                  80

Gln Ser Gln Phe Asp Ala Val Cys Asp Leu Val Tyr Asn Ala Gly Ala
                85                  90                  95

Gly Val Ile Ala Ala Ser Thr Gly Thr Gly Gln Ala Leu Arg Lys Gly
            100                 105                 110

Asp Ala Ser Thr Leu Arg Asn Lys Leu Thr Gln Phe His Tyr Gln Asn
        115                 120                 125

Gly Lys Ser Leu Leu Gly Leu Arg Arg Arg Ala Ala Gly Arg Val Ala
    130                 135                 140

Leu Phe Asp Gly Met Leu Trp Gln Gln Ala Glu Ala Ile Gly Arg Glu
145                 150                 155                 160

Ala Lys

<210> SEQ ID NO 31
<211> LENGTH: 162
<212> TYPE: PRT
<213> ORGANISM: Salmonella phage vB_SenS-Ent3

<400> SEQUENCE: 31

Met Ser Asn Arg Asn Ile Ser Asn Asn Gly Leu Lys Phe Thr Ala Ala
1               5                   10                  15

Phe Glu Gly Phe Gln Gly Thr Ala Tyr Lys Ala Thr Lys Asn Glu Lys
            20                  25                  30

Tyr Leu Thr Ile Gly Tyr Gly Ser Tyr Gly Pro His Val Tyr Glu Gly
        35                  40                  45

Gln Lys Ile Thr Glu Gly Gln Gly Leu Leu Leu His Lys Asp Met
    50                  55                  60

Ala Lys Ala Val Ala Ala Val Asp Ala Val Ala His Pro Ser Leu Asn
65                  70                  75                  80

Gln Ser Gln Phe Asp Ala Val Cys Asp Leu Val Tyr Asn Ala Gly Ala
                85                  90                  95
```

Gly Val Ile Ala Ala Ser Thr Gly Thr Gly Gln Ala Leu Arg Lys Gly
            100                 105                 110

Asp Val Ala Thr Leu Arg Asn Lys Leu Thr Gln Phe His Tyr Gln Asn
        115                 120                 125

Gly Lys Ser Leu Leu Gly Leu Arg Arg Arg Ala Ala Gly Arg Val Ala
    130                 135                 140

Leu Phe Asp Gly Met Leu Trp Gln Gln Ala Glu Ala Val Gly Arg Glu
145                 150                 155                 160

Ala Lys

<210> SEQ ID NO 32
<211> LENGTH: 132
<212> TYPE: PRT
<213> ORGANISM: Salmonella phage phi68

<400> SEQUENCE: 32

Met Ser Asn Arg Asn Ile Ser Asp Asn Gly Ile Lys Phe Thr Ala Ala
1               5                   10                  15

Phe Glu Gly Phe Arg Gly Thr Ala Tyr Arg Ala Thr Lys Asn Glu Lys
            20                  25                  30

Tyr Leu Thr Ile Gly Tyr Gly His Tyr Gly Ala Asp Val Lys Glu Gly
        35                  40                  45

Gln Lys Ile Thr Glu Gly Gln Gly Leu Leu Leu His Lys Asp Met
    50                  55                  60

Val Lys Ala Val Ala Ala Val Asp Ala Val Ala His Pro Pro Leu Asn
65                  70                  75                  80

Gln Ser Gln Phe Asp Ala Met Cys Asp Leu Val Tyr Asn Ala Gly Val
            85                  90                  95

Gly Val Ile Ala Ala Ser Thr Gly Thr Gly Gln Ala Leu Arg Lys Gly
            100                 105                 110

Asp Val Ala Thr Leu Arg Asn Lys Leu Thr Gln Phe His Tyr Gln Asn
        115                 120                 125

Gly Lys Ser Leu
    130

<210> SEQ ID NO 33
<211> LENGTH: 148
<212> TYPE: PRT
<213> ORGANISM: Salmonella phage phi68

<400> SEQUENCE: 33

Met Ser Asn Arg Asn Ile Ser Asp Asn Gly Ile Lys Phe Thr Ala Ala
1               5                   10                  15

Phe Glu Gly Phe Arg Gly Thr Ala Tyr Arg Ala Thr Lys Asn Glu Lys
            20                  25                  30

Tyr Leu Thr Ile Gly Tyr Gly His Tyr Gly Ala Asp Val Lys Glu Gly
        35                  40                  45

Gln Lys Ile Thr Glu Gly Gln Gly Leu Leu Leu His Lys Asp Met
    50                  55                  60

Val Lys Ala Val Ala Ala Val Asp Ala Val Ala His Pro Pro Leu Asn
65                  70                  75                  80

Gln Ser Gln Phe Asp Ala Met Cys Asp Leu Val Tyr Asn Ala Gly Val
            85                  90                  95

Gly Val Ile Ala Ala Ser Thr Gly Thr Gly Gln Ala Leu Arg Lys Gly
            100                 105                 110

Asp Val Ala Thr Leu Arg Asn Lys Leu Thr Gln Phe His Tyr Gln Asn

```
            115                 120                 125
Gly Lys Ser Leu Leu Gly Leu Arg Arg Arg Ala Ala Gly Arg Val Ala
    130                 135                 140
Leu Phe Asp Gly
145
```

<210> SEQ ID NO 34
<211> LENGTH: 156
<212> TYPE: PRT
<213> ORGANISM: Salmonella phage phi68

<400> SEQUENCE: 34

```
Ser Asp Asn Gly Ile Lys Phe Thr Ala Ala Phe Glu Gly Phe Arg Gly
1               5                  10                  15
Thr Ala Tyr Arg Ala Thr Lys Asn Glu Lys Tyr Leu Thr Ile Gly Tyr
            20                  25                  30
Gly His Tyr Gly Ala Asp Val Lys Glu Gly Gln Lys Ile Thr Glu Gly
        35                  40                  45
Gln Gly Leu Leu Leu His Lys Asp Met Val Lys Ala Val Ala Ala
    50                  55                  60
Val Asp Ala Val Ala His Pro Pro Leu Asn Gln Ser Gln Phe Asp Ala
65                  70                  75                  80
Met Cys Asp Leu Val Tyr Asn Ala Gly Val Gly Val Ile Ala Ala Ser
                85                  90                  95
Thr Gly Thr Gly Gln Ala Leu Arg Lys Gly Asp Val Ala Thr Leu Arg
            100                 105                 110
Asn Lys Leu Thr Gln Phe His Tyr Gln Asn Gly Lys Ser Leu Leu Gly
        115                 120                 125
Leu Arg Arg Arg Ala Ala Gly Arg Val Ala Leu Phe Asp Gly Met Leu
    130                 135                 140
Trp Gln Gln Ala Glu Ala Ile Gly Arg Gly Ala Lys
145                 150                 155
```

<210> SEQ ID NO 35
<211> LENGTH: 161
<212> TYPE: PRT
<213> ORGANISM: Artificial sequence
<220> FEATURE:
<223> OTHER INFORMATION: Synthetic Lys68 (P78L) w/o Met

<400> SEQUENCE: 35

```
Ser Asn Arg Asn Ile Ser Asp Asn Gly Ile Lys Phe Thr Ala Ala Phe
1               5                  10                  15
Glu Gly Phe Arg Gly Thr Ala Tyr Arg Ala Thr Lys Asn Glu Lys Tyr
            20                  25                  30
Leu Thr Ile Gly Tyr Gly His Tyr Gly Ala Asp Val Lys Glu Gly Gln
        35                  40                  45
Lys Ile Thr Glu Gly Gln Gly Leu Leu Leu His Lys Asp Met Val
    50                  55                  60
Lys Ala Val Ala Ala Val Asp Ala Val Ala His Pro Leu Leu Asn Gln
65                  70                  75                  80
Ser Gln Phe Asp Ala Met Cys Asp Leu Val Tyr Asn Ala Gly Val Gly
                85                  90                  95
Val Ile Ala Ala Ser Thr Gly Thr Gly Gln Ala Leu Arg Lys Gly Asp
            100                 105                 110
Val Ala Thr Leu Arg Asn Lys Leu Thr Gln Phe His Tyr Gln Asn Gly
        115                 120                 125
```

```
Lys Ser Leu Leu Gly Leu Arg Arg Arg Ala Ala Gly Arg Val Ala Leu
        130                 135                 140

Phe Asp Gly Met Leu Trp Gln Gln Ala Glu Ala Ile Gly Arg Gly Ala
145                 150                 155                 160

Lys

<210> SEQ ID NO 36
<211> LENGTH: 161
<212> TYPE: PRT
<213> ORGANISM: Artificial sequence
<220> FEATURE:
<223> OTHER INFORMATION: Synthetic Lys68 (P78L,G104D,A156V) w/o Met

<400> SEQUENCE: 36

Ser Asn Arg Asn Ile Ser Asp Asn Gly Ile Lys Phe Thr Ala Ala Phe
1               5                   10                  15

Glu Gly Phe Arg Gly Thr Ala Tyr Arg Ala Thr Lys Asn Glu Lys Tyr
            20                  25                  30

Leu Thr Ile Gly Tyr Gly His Tyr Gly Ala Asp Val Lys Glu Gly Gln
        35                  40                  45

Lys Ile Thr Glu Gly Gln Gly Leu Leu Leu Leu His Lys Asp Met Val
50                  55                  60

Lys Ala Val Ala Ala Val Asp Ala Val Ala His Pro Leu Leu Asn Gln
65                  70                  75                  80

Ser Gln Phe Asp Ala Met Cys Asp Leu Val Tyr Asn Ala Gly Val Gly
            85                  90                  95

Val Ile Ala Ala Ser Thr Asp Thr Gly Gln Ala Leu Arg Lys Gly Asp
            100                 105                 110

Val Ala Thr Leu Arg Asn Lys Leu Thr Gln Phe His Tyr Gln Asn Gly
        115                 120                 125

Lys Ser Leu Leu Gly Leu Arg Arg Arg Ala Ala Gly Arg Val Ala Leu
        130                 135                 140

Phe Asp Gly Met Leu Trp Gln Gln Ala Glu Val Ile Gly Arg Gly Ala
145                 150                 155                 160

Lys

<210> SEQ ID NO 37
<211> LENGTH: 161
<212> TYPE: PRT
<213> ORGANISM: Artificial sequence
<220> FEATURE:
<223> OTHER INFORMATION: Synthetic Lys68 (P78S) w/o Met

<400> SEQUENCE: 37

Ser Asn Arg Asn Ile Ser Asp Asn Gly Ile Lys Phe Thr Ala Ala Phe
1               5                   10                  15

Glu Gly Phe Arg Gly Thr Ala Tyr Arg Ala Thr Lys Asn Glu Lys Tyr
            20                  25                  30

Leu Thr Ile Gly Tyr Gly His Tyr Gly Ala Asp Val Lys Glu Gly Gln
        35                  40                  45

Lys Ile Thr Glu Gly Gln Gly Leu Leu Leu Leu His Lys Asp Met Val
50                  55                  60

Lys Ala Val Ala Ala Val Asp Ala Val Ala His Pro Ser Leu Asn Gln
65                  70                  75                  80

Ser Gln Phe Asp Ala Met Cys Asp Leu Val Tyr Asn Ala Gly Val Gly
            85                  90                  95
```

```
Val Ile Ala Ala Ser Thr Gly Thr Gly Gln Ala Leu Arg Lys Gly Asp
            100                 105                 110

Val Ala Thr Leu Arg Asn Lys Leu Thr Gln Phe His Tyr Gln Asn Gly
            115                 120                 125

Lys Ser Leu Leu Gly Leu Arg Arg Arg Ala Ala Gly Arg Val Ala Leu
            130                 135                 140

Phe Asp Gly Met Leu Trp Gln Gln Ala Glu Ala Ile Gly Arg Gly Ala
145                 150                 155                 160

Lys

<210> SEQ ID NO 38
<211> LENGTH: 161
<212> TYPE: PRT
<213> ORGANISM: Artificial sequence
<220> FEATURE:
<223> OTHER INFORMATION: Synthetic Lys68 (G19S, P78S) w/o Met

<400> SEQUENCE: 38

Ser Asn Arg Asn Ile Ser Asp Asn Gly Ile Lys Phe Thr Ala Ala Phe
1               5                   10                  15

Glu Ser Phe Arg Gly Thr Ala Tyr Arg Ala Thr Lys Asn Glu Lys Tyr
            20                  25                  30

Leu Thr Ile Gly Tyr Gly His Tyr Gly Ala Asp Val Lys Glu Gly Gln
            35                  40                  45

Lys Ile Thr Glu Gly Gln Gly Leu Leu Leu His Lys Asp Met Val
            50                  55                  60

Lys Ala Val Ala Ala Val Asp Ala Val Ala His Pro Ser Leu Asn Gln
65                  70                  75                  80

Ser Gln Phe Asp Ala Met Cys Asp Leu Val Tyr Asn Ala Gly Val Gly
            85                  90                  95

Val Ile Ala Ala Ser Thr Gly Thr Gly Gln Ala Leu Arg Lys Gly Asp
            100                 105                 110

Val Ala Thr Leu Arg Asn Lys Leu Thr Gln Phe His Tyr Gln Asn Gly
            115                 120                 125

Lys Ser Leu Leu Gly Leu Arg Arg Arg Ala Ala Gly Arg Val Ala Leu
            130                 135                 140

Phe Asp Gly Met Leu Trp Gln Gln Ala Glu Ala Ile Gly Arg Gly Ala
145                 150                 155                 160

Lys

<210> SEQ ID NO 39
<211> LENGTH: 161
<212> TYPE: PRT
<213> ORGANISM: Artificial sequence
<220> FEATURE:
<223> OTHER INFORMATION: Synthetic Lys68 (I11V, P78S) w/o Met

<400> SEQUENCE: 39

Ser Asn Arg Asn Ile Ser Asp Asn Gly Val Lys Phe Thr Ala Ala Phe
1               5                   10                  15

Glu Gly Phe Arg Gly Thr Ala Tyr Arg Ala Thr Lys Asn Glu Lys Tyr
            20                  25                  30

Leu Thr Ile Gly Tyr Gly His Tyr Gly Ala Asp Val Lys Glu Gly Gln
            35                  40                  45

Lys Ile Thr Glu Gly Gln Gly Leu Leu Leu His Lys Asp Met Val
            50                  55                  60

Lys Ala Val Ala Ala Val Asp Ala Val Ala His Pro Ser Leu Asn Gln
```

```
                65                  70                  75                  80
Ser Gln Phe Asp Ala Met Cys Asp Leu Val Tyr Asn Ala Gly Val Gly
                    85                  90                  95

Val Ile Ala Ala Ser Thr Gly Thr Gly Gln Ala Leu Arg Lys Gly Asp
                100                 105                 110

Val Ala Thr Leu Arg Asn Lys Leu Thr Gln Phe His Tyr Gln Asn Gly
                115                 120                 125

Lys Ser Leu Leu Gly Leu Arg Arg Ala Ala Gly Arg Val Ala Leu
                130                 135                 140

Phe Asp Gly Met Leu Trp Gln Gln Ala Glu Ala Ile Gly Arg Gly Ala
145                 150                 155                 160

Lys

<210> SEQ ID NO 40
<211> LENGTH: 161
<212> TYPE: PRT
<213> ORGANISM: Artificial sequence
<220> FEATURE:
<223> OTHER INFORMATION: Synthetic Lys68 (P78S, G134C) w/o Met

<400> SEQUENCE: 40

Ser Asn Arg Asn Ile Ser Asp Asn Gly Ile Lys Phe Thr Ala Ala Phe
1               5                   10                  15

Glu Gly Phe Arg Gly Thr Ala Tyr Arg Ala Thr Lys Asn Glu Lys Tyr
                20                  25                  30

Leu Thr Ile Gly Tyr Gly His Tyr Gly Ala Asp Val Lys Glu Gly Gln
                35                  40                  45

Lys Ile Thr Glu Gly Gln Gly Leu Leu Leu Leu His Lys Asp Met Val
                50                  55                  60

Lys Ala Val Ala Ala Val Asp Ala Val Ala His Pro Ser Leu Asn Gln
65                  70                  75                  80

Ser Gln Phe Asp Ala Met Cys Asp Leu Val Tyr Asn Ala Gly Val Gly
                    85                  90                  95

Val Ile Ala Ala Ser Thr Gly Thr Gly Gln Ala Leu Arg Lys Gly Asp
                100                 105                 110

Val Ala Thr Leu Arg Asn Lys Leu Thr Gln Phe His Tyr Gln Asn Gly
                115                 120                 125

Lys Ser Leu Leu Cys Leu Arg Arg Ala Ala Gly Arg Val Ala Leu
                130                 135                 140

Phe Asp Gly Met Leu Trp Gln Gln Ala Glu Ala Ile Gly Arg Gly Ala
145                 150                 155                 160

Lys

<210> SEQ ID NO 41
<211> LENGTH: 6
<212> TYPE: PRT
<213> ORGANISM: Artificial sequence
<220> FEATURE:
<223> OTHER INFORMATION: Synthetic peptide

<400> SEQUENCE: 41

Lys Arg Lys Lys Arg Lys
1               5

<210> SEQ ID NO 42
<211> LENGTH: 5
<212> TYPE: PRT
<213> ORGANISM: Artificial sequence
```

```
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 42

Lys Arg Xaa Lys Arg
1               5

<210> SEQ ID NO 43
<211> LENGTH: 5
<212> TYPE: PRT
<213> ORGANISM: Artificial sequence
<220> FEATURE:
<223> OTHER INFORMATION: Synthetic peptide

<400> SEQUENCE: 43

Lys Arg Ser Lys Arg
1               5

<210> SEQ ID NO 44
<211> LENGTH: 5
<212> TYPE: PRT
<213> ORGANISM: Artificial sequence
<220> FEATURE:
<223> OTHER INFORMATION: Synthetic peptide

<400> SEQUENCE: 44

Lys Arg Gly Ser Gly
1               5

<210> SEQ ID NO 45
<211> LENGTH: 9
<212> TYPE: PRT
<213> ORGANISM: Artificial sequence
<220> FEATURE:
<223> OTHER INFORMATION: Synthetic peptide

<400> SEQUENCE: 45

Lys Arg Lys Lys Arg Lys Lys Arg Lys
1               5

<210> SEQ ID NO 46
<211> LENGTH: 9
<212> TYPE: PRT
<213> ORGANISM: Artificial sequence
<220> FEATURE:
<223> OTHER INFORMATION: Synthetic peptide

<400> SEQUENCE: 46

Arg Arg Arg Arg Arg Arg Arg Arg
1               5

<210> SEQ ID NO 47
<211> LENGTH: 8
<212> TYPE: PRT
<213> ORGANISM: Artificial sequence
<220> FEATURE:
<223> OTHER INFORMATION: Synthetic peptide

<400> SEQUENCE: 47

Lys Lys Lys Lys Lys Lys Lys
1               5

<210> SEQ ID NO 48
```

```
<211> LENGTH: 10
<212> TYPE: PRT
<213> ORGANISM: Artificial sequence
<220> FEATURE:
<223> OTHER INFORMATION: Synthetic peptide

<400> SEQUENCE: 48

Lys Arg Lys Lys Arg Lys Lys Arg Lys Lys
1               5                   10

<210> SEQ ID NO 49
<211> LENGTH: 12
<212> TYPE: PRT
<213> ORGANISM: Artificial sequence
<220> FEATURE:
<223> OTHER INFORMATION: Synthetic peptide

<400> SEQUENCE: 49

Lys Arg Lys Lys Arg Lys Lys Arg Lys Lys Arg Lys
1               5                   10

<210> SEQ ID NO 50
<211> LENGTH: 14
<212> TYPE: PRT
<213> ORGANISM: Artificial sequence
<220> FEATURE:
<223> OTHER INFORMATION: Synthetic peptide

<400> SEQUENCE: 50

Lys Arg Lys Lys Arg Lys Lys Arg Lys Lys Arg Lys Lys Arg
1               5                   10

<210> SEQ ID NO 51
<211> LENGTH: 16
<212> TYPE: PRT
<213> ORGANISM: Artificial sequence
<220> FEATURE:
<223> OTHER INFORMATION: Synthetic peptide

<400> SEQUENCE: 51

Lys Lys Lys Lys Lys Lys Lys Lys Lys Lys Lys Lys Lys Lys Lys Lys
1               5                   10                  15

<210> SEQ ID NO 52
<211> LENGTH: 18
<212> TYPE: PRT
<213> ORGANISM: Artificial sequence
<220> FEATURE:
<223> OTHER INFORMATION: Synthetic peptide

<400> SEQUENCE: 52

Lys Arg Lys Lys Arg Lys Lys Arg Lys Lys Arg Lys Lys Arg Lys Lys
1               5                   10                  15

Arg Lys

<210> SEQ ID NO 53
<211> LENGTH: 19
<212> TYPE: PRT
<213> ORGANISM: Artificial sequence
<220> FEATURE:
<223> OTHER INFORMATION: Synthetic peptide

<400> SEQUENCE: 53

Lys Arg Lys Lys Arg Lys Lys Arg Lys Lys Arg Lys Lys Arg Lys Lys
1               5                   10                  15

Arg Lys Lys
```

<210> SEQ ID NO 54
<211> LENGTH: 19
<212> TYPE: PRT
<213> ORGANISM: Artificial sequence
<220> FEATURE:
<223> OTHER INFORMATION: Synthetic peptide

<400> SEQUENCE: 54

Arg Arg Arg Arg Arg Arg Arg Arg Arg Arg Arg Arg Arg Arg Arg Arg
1               5                   10                  15

Arg Arg Arg

<210> SEQ ID NO 55
<211> LENGTH: 19
<212> TYPE: PRT
<213> ORGANISM: Artificial sequence
<220> FEATURE:
<223> OTHER INFORMATION: Synthetic peptide

<400> SEQUENCE: 55

Lys Lys Lys Lys Lys Lys Lys Lys Lys Lys Lys Lys Lys Lys Lys Lys
1               5                   10                  15

Lys Lys Lys

<210> SEQ ID NO 56
<211> LENGTH: 20
<212> TYPE: PRT
<213> ORGANISM: Artificial sequence
<220> FEATURE:
<223> OTHER INFORMATION: Synthetic peptide

<400> SEQUENCE: 56

Lys Arg Lys Lys Arg Lys Lys Arg Lys Arg Ser Lys Arg Lys Lys Arg
1               5                   10                  15

Lys Lys Arg Lys
            20

<210> SEQ ID NO 57
<211> LENGTH: 21
<212> TYPE: PRT
<213> ORGANISM: Artificial sequence
<220> FEATURE:
<223> OTHER INFORMATION: Synthetic peptide

<400> SEQUENCE: 57

Lys Arg Lys Lys Arg Lys Lys Arg Lys Arg Ser Lys Arg Lys Lys Arg
1               5                   10                  15

Lys Lys Arg Lys Lys
            20

<210> SEQ ID NO 58
<211> LENGTH: 21
<212> TYPE: PRT
<213> ORGANISM: Artificial sequence
<220> FEATURE:
<223> OTHER INFORMATION: Synthetic peptide

<400> SEQUENCE: 58

Lys Arg Lys Lys Arg Lys Lys Arg Lys Lys Arg Lys Lys Arg Lys Lys
1               5                   10                  15

Arg Lys Lys Arg Lys
            20

```
<210> SEQ ID NO 59
<211> LENGTH: 22
<212> TYPE: PRT
<213> ORGANISM: Artificial sequence
<220> FEATURE:
<223> OTHER INFORMATION: Synthetic peptide

<400> SEQUENCE: 59

Lys Arg Lys Lys Arg Lys Lys Arg Lys Arg Gly Ser Gly Lys Arg Lys
1               5                   10                  15

Lys Arg Lys Lys Arg Lys
            20

<210> SEQ ID NO 60
<211> LENGTH: 24
<212> TYPE: PRT
<213> ORGANISM: Artificial sequence
<220> FEATURE:
<223> OTHER INFORMATION: Synthetic peptide

<400> SEQUENCE: 60

Lys Arg Lys Lys Arg Lys Lys Arg Lys Arg Gly Ser Gly Ser Gly Lys
1               5                   10                  15

Arg Lys Lys Arg Lys Lys Arg Lys
            20

<210> SEQ ID NO 61
<211> LENGTH: 25
<212> TYPE: PRT
<213> ORGANISM: Artificial sequence
<220> FEATURE:
<223> OTHER INFORMATION: Synthetic peptide

<400> SEQUENCE: 61

Lys Arg Lys Lys Arg Lys Lys Arg Lys Lys Arg Lys Lys Arg Lys Lys
1               5                   10                  15

Arg Lys Lys Arg Lys Lys Arg Lys Lys
            20                  25

<210> SEQ ID NO 62
<211> LENGTH: 31
<212> TYPE: PRT
<213> ORGANISM: Artificial sequence
<220> FEATURE:
<223> OTHER INFORMATION: Synthetic peptide

<400> SEQUENCE: 62

Lys Arg Lys Lys Arg Lys Lys Arg Lys Arg Ser Lys Arg Lys Lys Arg
1               5                   10                  15

Lys Lys Arg Lys Arg Ser Lys Arg Lys Lys Arg Lys Lys Arg Lys
            20                  25                  30

<210> SEQ ID NO 63
<211> LENGTH: 38
<212> TYPE: PRT
<213> ORGANISM: Artificial sequence
<220> FEATURE:
<223> OTHER INFORMATION: Synthetic peptide

<400> SEQUENCE: 63

Lys Arg Lys Lys Arg Lys Lys Arg Lys Arg Gly Ser Gly Ser Gly Lys
1               5                   10                  15

Arg Lys Lys Arg Lys Lys Arg Lys Gly Ser Gly Ser Gly Lys Arg Lys
            20                  25                  30
```

Lys Arg Lys Lys Arg Lys
          35

<210> SEQ ID NO 64
<211> LENGTH: 39
<212> TYPE: PRT
<213> ORGANISM: Artificial sequence
<220> FEATURE:
<223> OTHER INFORMATION: Synthetic peptide

<400> SEQUENCE: 64

Lys Arg Lys Lys Arg Lys Lys Arg Lys Lys Arg Lys Lys Arg Lys Lys
1               5                   10                  15

Arg Lys Lys Arg Lys Lys Arg Lys Lys Arg Lys Lys Arg Lys Lys Arg
            20                  25                  30

Lys Lys Arg Lys Lys Arg Lys
          35

<210> SEQ ID NO 65
<211> LENGTH: 42
<212> TYPE: PRT
<213> ORGANISM: Artificial sequence
<220> FEATURE:
<223> OTHER INFORMATION: Synthetic peptide

<400> SEQUENCE: 65

Lys Arg Lys Lys Arg Lys Lys Arg Lys Arg Ser Lys Arg Lys Lys Arg
1               5                   10                  15

Lys Lys Arg Lys Arg Ser Lys Arg Lys Lys Arg Lys Lys Arg Lys Arg
            20                  25                  30

Ser Lys Arg Lys Lys Arg Lys Lys Arg Lys
          35                  40

<210> SEQ ID NO 66
<211> LENGTH: 37
<212> TYPE: PRT
<213> ORGANISM: Homo sapiens

<400> SEQUENCE: 66

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
          35

<210> SEQ ID NO 67
<211> LENGTH: 29
<212> TYPE: PRT
<213> ORGANISM: unknown
<220> FEATURE:
<223> OTHER INFORMATION: SMAP-29 sheep

<400> SEQUENCE: 67

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly
            20                  25

<210> SEQ ID NO 68
<211> LENGTH: 13
<212> TYPE: PRT

```
<213> ORGANISM: unknown
<220> FEATURE:
<223> OTHER INFORMATION: Indolicidine bovine

<400> SEQUENCE: 68

Ile Leu Pro Trp Lys Trp Pro Trp Trp Pro Trp Arg Arg
1               5                   10

<210> SEQ ID NO 69
<211> LENGTH: 18
<212> TYPE: PRT
<213> ORGANISM: unknown
<220> FEATURE:
<223> OTHER INFORMATION: Protegrin Porcine

<400> SEQUENCE: 69

Arg Gly Gly Arg Leu Cys Tyr Cys Arg Arg Arg Phe Cys Val Cys Val
1               5                   10                  15

Gly Arg

<210> SEQ ID NO 70
<211> LENGTH: 31
<212> TYPE: PRT
<213> ORGANISM: unknown
<220> FEATURE:
<223> OTHER INFORMATION: Cecropin P1 Mammal (pig)

<400> SEQUENCE: 70

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 71
<211> LENGTH: 23
<212> TYPE: PRT
<213> ORGANISM: unknown
<220> FEATURE:
<223> OTHER INFORMATION: Magainin frog

<400> SEQUENCE: 71

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 72
<211> LENGTH: 25
<212> TYPE: PRT
<213> ORGANISM: unknown
<220> FEATURE:
<223> OTHER INFORMATION: Pleurocidin fish

<400> SEQUENCE: 72

Gly Trp Gly Ser Phe Phe Lys Lys Ala Ala His Val Gly Lys His Val
1               5                   10                  15

Gly Lys Ala Ala Leu Thr His Tyr Leu
            20                  25

<210> SEQ ID NO 73
<211> LENGTH: 36
<212> TYPE: PRT
<213> ORGANISM: Aedes aegypti

<400> SEQUENCE: 73
```

```
Gly Gly Leu Lys Lys Leu Gly Lys Lys Leu Glu Gly Ala Gly Lys Arg
1               5                   10                  15

Val Phe Asn Ala Ala Glu Lys Ala Leu Pro Val Val Ala Gly Ala Lys
            20                  25                  30

Ala Leu Arg Lys
        35
```

<210> SEQ ID NO 74
<211> LENGTH: 40
<212> TYPE: PRT
<213> ORGANISM: Drosophila melanogaster

<400> SEQUENCE: 74

```
Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Pro Gln Gln Ala Ala
            20                  25                  30

Asn Val Ala Ala Thr Ala Arg Gly
        35                  40
```

<210> SEQ ID NO 75
<211> LENGTH: 21
<212> TYPE: PRT
<213> ORGANISM: unknown
<220> FEATURE:
<223> OTHER INFORMATION: Buforin II vertebrate

<400> SEQUENCE: 75

```
Thr Arg Ser Ser Arg Ala Gly Leu Gln Phe Pro Val Gly Arg Val His
1               5                   10                  15

Arg Leu Leu Arg Lys
            20
```

<210> SEQ ID NO 76
<211> LENGTH: 39
<212> TYPE: PRT
<213> ORGANISM: unknown
<220> FEATURE:
<223> OTHER INFORMATION: Sarcotoxin IA Fly

<400> SEQUENCE: 76

```
Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg
        35
```

<210> SEQ ID NO 77
<211> LENGTH: 17
<212> TYPE: PRT
<213> ORGANISM: Apis mellifera

<400> SEQUENCE: 77

```
Ala Asn Arg Pro Val Tyr Ile Pro Pro Pro Arg Pro Pro His Pro Arg
1               5                   10                  15

Leu
```

<210> SEQ ID NO 78
<211> LENGTH: 24
<212> TYPE: PRT

```
<213> ORGANISM: unknown
<220> FEATURE:
<223> OTHER INFORMATION: Ascaphine 5 Frog

<400> SEQUENCE: 78

Gly Ile Lys Asp Trp Ile Lys Gly Ala Ala Lys Lys Leu Ile Lys Thr
1               5                   10                  15

Val Ala Ser His Ile Ala Asn Gln
            20

<210> SEQ ID NO 79
<211> LENGTH: 22
<212> TYPE: PRT
<213> ORGANISM: unknown
<220> FEATURE:
<223> OTHER INFORMATION: Nigrocine 2 Frog

<400> SEQUENCE: 79

Gly Leu Leu Ser Lys Val Leu Gly Val Gly Lys Lys Val Leu Cys Gly
1               5                   10                  15

Val Ser Gly Leu Val Cys
            20

<210> SEQ ID NO 80
<211> LENGTH: 24
<212> TYPE: PRT
<213> ORGANISM: unknown
<220> FEATURE:
<223> OTHER INFORMATION: Pseudin 1 Rana Frog

<400> SEQUENCE: 80

Gly Leu Asn Thr Leu Lys Lys Val Phe Gln Gly Leu His Glu Ala Ile
1               5                   10                  15

Lys Leu Ile Asn Asn His Val Gln
            20

<210> SEQ ID NO 81
<211> LENGTH: 18
<212> TYPE: PRT
<213> ORGANISM: unknown
<220> FEATURE:
<223> OTHER INFORMATION: Ranalexin Frog

<400> SEQUENCE: 81

Phe Leu Gly Gly Leu Ile Val Pro Ala Met Ile Cys Ala Val Thr Lys
1               5                   10                  15

Lys Cys

<210> SEQ ID NO 82
<211> LENGTH: 26
<212> TYPE: PRT
<213> ORGANISM: unknown
<220> FEATURE:
<223> OTHER INFORMATION: Melittin bee

<400> SEQUENCE: 82

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 83
<211> LENGTH: 25
<212> TYPE: PRT
```

```
<213> ORGANISM: unknown
<220> FEATURE:
<223> OTHER INFORMATION: Lycotoxin 1 Spider

<400> SEQUENCE: 83

Ile Trp Leu Thr Ala Leu Lys Phe Leu Gly Lys His Ala Ala Lys Lys
1               5                   10                  15

Leu Ala Lys Gln Gln Leu Ser Lys Leu
            20                  25

<210> SEQ ID NO 84
<211> LENGTH: 19
<212> TYPE: PRT
<213> ORGANISM: unknown
<220> FEATURE:
<223> OTHER INFORMATION: Parasin 1 Fish

<400> SEQUENCE: 84

Lys Gly Arg Gly Lys Gln Gly Gly Lys Val Arg Ala Lys Ala Lys Thr
1               5                   10                  15

Arg Ser Ser

<210> SEQ ID NO 85
<211> LENGTH: 39
<212> TYPE: PRT
<213> ORGANISM: unknown
<220> FEATURE:
<223> OTHER INFORMATION: Buforin I Toad

<400> SEQUENCE: 85

Ala Gly Arg Gly Lys Gln Gly Gly Lys Val Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Asn Tyr
        35

<210> SEQ ID NO 86
<211> LENGTH: 34
<212> TYPE: PRT
<213> ORGANISM: unknown
<220> FEATURE:
<223> OTHER INFORMATION: Dermaseptin 1 Frog

<400> SEQUENCE: 86

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Gly
            20                  25                  30

Thr Gln

<210> SEQ ID NO 87
<211> LENGTH: 12
<212> TYPE: PRT
<213> ORGANISM: unknown
<220> FEATURE:
<223> OTHER INFORMATION: Bactenecin 1 Cow

<400> SEQUENCE: 87

Arg Leu Cys Arg Ile Val Val Ile Arg Val Cys Arg
1               5                   10

<210> SEQ ID NO 88
```

```
<211> LENGTH: 21
<212> TYPE: PRT
<213> ORGANISM: unknown
<220> FEATURE:
<223> OTHER INFORMATION: Thanatin Insect

<400> SEQUENCE: 88

Gly Ser Lys Lys Pro Val Pro Ile Ile Tyr Cys Asn Arg Arg Thr Gly
1               5                   10                  15

Lys Cys Gln Arg Met
            20

<210> SEQ ID NO 89
<211> LENGTH: 19
<212> TYPE: PRT
<213> ORGANISM: unknown
<220> FEATURE:
<223> OTHER INFORMATION: Brevinin 1T Rana frogs

<400> SEQUENCE: 89

Val Asn Pro Ile Ile Leu Gly Val Leu Pro Lys Val Cys Leu Ile Thr
1               5                   10                  15

Lys Lys Cys

<210> SEQ ID NO 90
<211> LENGTH: 26
<212> TYPE: PRT
<213> ORGANISM: unknown
<220> FEATURE:
<223> OTHER INFORMATION: Ranateurin 1 Rana frog

<400> SEQUENCE: 90

Ser Met Leu Ser Val Leu Lys Asn Leu Gly Lys Val Gly Leu Gly Phe
1               5                   10                  15

Val Ala Cys Lys Ile Asn Ile Lys Gln Cys
            20                  25

<210> SEQ ID NO 91
<211> LENGTH: 46
<212> TYPE: PRT
<213> ORGANISM: unknown
<220> FEATURE:
<223> OTHER INFORMATION: Esculentin 1 Rana frogs

<400> SEQUENCE: 91

Gly Ile Phe Ser Lys Leu Gly Arg Lys Lys Ile Lys Asn Leu Leu Ile
1               5                   10                  15

Ser Gly Leu Lys Asn Val Gly Lys Glu Val Gly Met Asp Val Val Arg
            20                  25                  30

Thr Gly Ile Lys Ile Ala Gly Cys Lys Ile Lys Gly Glu Cys
        35                  40                  45

<210> SEQ ID NO 92
<211> LENGTH: 17
<212> TYPE: PRT
<213> ORGANISM: Limulus polyphemus

<400> SEQUENCE: 92

Arg Trp Cys Phe Arg Val Cys Tyr Arg Gly Ile Cys Tyr Arg Lys Cys
1               5                   10                  15

Arg

<210> SEQ ID NO 93
```

```
<211> LENGTH: 25
<212> TYPE: PRT
<213> ORGANISM: unknown
<220> FEATURE:
<223> OTHER INFORMATION: Androctonin Scorpion

<400> SEQUENCE: 93

Arg Ser Val Cys Arg Gln Ile Lys Ile Cys Arg Arg Arg Gly Gly Cys
1               5                   10                  15

Tyr Tyr Lys Cys Thr Asn Arg Pro Tyr
            20                  25

<210> SEQ ID NO 94
<211> LENGTH: 30
<212> TYPE: PRT
<213> ORGANISM: Homo sapiens

<400> SEQUENCE: 94

Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 95
<211> LENGTH: 38
<212> TYPE: PRT
<213> ORGANISM: unknown
<220> FEATURE:
<223> OTHER INFORMATION: beta-defensin cow

<400> SEQUENCE: 95

Asn Pro Val Ser Cys Val Arg Asn Lys Gly Ile Cys Val Pro Ile Arg
1               5                   10                  15

Cys Pro Gly Ser Met Lys Gln Ile Gly Thr Cys Val Gly Arg Ala Val
            20                  25                  30

Lys Cys Cys Arg Lys Lys
        35

<210> SEQ ID NO 96
<211> LENGTH: 18
<212> TYPE: PRT
<213> ORGANISM: unknown
<220> FEATURE:
<223> OTHER INFORMATION: theta-defensin monkey

<400> SEQUENCE: 96

Gly Phe Cys Arg Cys Leu Cys Arg Arg Gly Val Cys Arg Cys Ile Cys
1               5                   10                  15

Thr Arg

<210> SEQ ID NO 97
<211> LENGTH: 40
<212> TYPE: PRT
<213> ORGANISM: unknown
<220> FEATURE:
<223> OTHER INFORMATION: defensin (sapecin A) insect

<400> SEQUENCE: 97

Ala Thr Cys Asp Leu Leu Ser Gly Thr Gly Ile Asn His Ser Ala Cys
1               5                   10                  15

Ala Ala His Cys Leu Leu Arg Gly Asn Arg Gly Gly Tyr Cys Asn Gly
            20                  25                  30

Lys Ala Val Cys Val Cys Arg Asn
```

<210> SEQ ID NO 98
<211> LENGTH: 46
<212> TYPE: PRT
<213> ORGANISM: unknown
<220> FEATURE:
<223> OTHER INFORMATION: Thionin (crambin) plant

<400> SEQUENCE: 98

Thr Thr Cys Cys Pro Ser Ile Val Ala Arg Ser Asn Phe Asn Val Cys
1               5                   10                  15

Arg Ile Pro Gly Thr Pro Glu Ala Ile Cys Ala Thr Tyr Thr Gly Cys
                20                  25                  30

Ile Ile Ile Pro Gly Ala Thr Cys Pro Gly Asp Tyr Ala Asn
            35                  40                  45

<210> SEQ ID NO 99
<211> LENGTH: 50
<212> TYPE: PRT
<213> ORGANISM: unknown
<220> FEATURE:
<223> OTHER INFORMATION: defensin from radish

<400> SEQUENCE: 99

Gln Lys Leu Cys Gln Arg Pro Ser Gly Thr Trp Ser Gly Val Cys Gly
1               5                   10                  15

Asn Asn Asn Ala Cys Lys Asn Gln Cys Ile Arg Leu Glu Lys Ala Arg
                20                  25                  30

His Gly Ser Cys Asn Tyr Val Phe Pro Ala His Cys Ile Cys Tyr Phe
            35                  40                  45

Pro Cys
    50

<210> SEQ ID NO 100
<211> LENGTH: 44
<212> TYPE: PRT
<213> ORGANISM: Drosophila melanogaster

<400> SEQUENCE: 100

Asp Cys Leu Ser Gly Arg Tyr Lys Gly Pro Cys Ala Val Trp Asp Asn
1               5                   10                  15

Glu Thr Cys Arg Arg Val Cys Lys Glu Gly Arg Ser Ser Gly His
                20                  25                  30

Cys Ser Pro Ser Leu Lys Cys Trp Cys Glu Gly Cys
            35                  40

<210> SEQ ID NO 101
<211> LENGTH: 25
<212> TYPE: PRT
<213> ORGANISM: Homo sapiens

<400> SEQUENCE: 101

Asp Thr His Phe Pro Ile Cys Ile Phe Cys Cys Gly Cys Cys His Arg
1               5                   10                  15

Ser Lys Cys Gly Met Cys Cys Lys Thr
                20                  25

<210> SEQ ID NO 102
<211> LENGTH: 44
<212> TYPE: PRT
<213> ORGANISM: unknown

```
<220> FEATURE:
<223> OTHER INFORMATION: Bac 5 Cow

<400> SEQUENCE: 102

Arg Phe Arg Pro Pro Ile Arg Arg Pro Pro Ile Arg Pro Pro Phe Tyr
1               5                   10                  15

Pro Pro Phe Arg Pro Pro Ile Arg Pro Pro Ile Phe Pro Pro Ile Arg
                20                  25                  30

Pro Pro Phe Arg Pro Pro Leu Gly Arg Pro Phe Pro
                35                  40

<210> SEQ ID NO 103
<211> LENGTH: 39
<212> TYPE: PRT
<213> ORGANISM: unknown
<220> FEATURE:
<223> OTHER INFORMATION: PR-39 Pig

<400> SEQUENCE: 103

Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro
                20                  25                  30

Arg Phe Pro Pro Arg Phe Pro
                35

<210> SEQ ID NO 104
<211> LENGTH: 20
<212> TYPE: PRT
<213> ORGANISM: unknown
<220> FEATURE:
<223> OTHER INFORMATION: Pyrrhocoricin Insect

<400> SEQUENCE: 104

Val Asp Lys Gly Ser Tyr Leu Pro Arg Pro Thr Pro Pro Arg Pro Ile
1               5                   10                  15

Tyr Asn Arg Asn
                20

<210> SEQ ID NO 105
<211> LENGTH: 24
<212> TYPE: PRT
<213> ORGANISM: Homo sapiens

<400> SEQUENCE: 105

Asp Ser His Ala Lys Arg His His Gly Tyr Lys Arg Lys Phe His Glu
1               5                   10                  15

Lys His His Ser His Arg Gly Tyr
                20

<210> SEQ ID NO 106
<211> LENGTH: 19
<212> TYPE: PRT
<213> ORGANISM: Unknown
<220> FEATURE:
<223> OTHER INFORMATION: ECP19

<400> SEQUENCE: 106

Arg Pro Pro Gln Phe Thr Arg Ala Gln Trp Phe Ala Ile Gln His Ile
1               5                   10                  15

Ser Leu Asn
```

-continued

```
<210> SEQ ID NO 107
<211> LENGTH: 23
<212> TYPE: PRT
<213> ORGANISM: Unknown
<220> FEATURE:
<223> OTHER INFORMATION: MSI-594

<400> SEQUENCE: 107

Gly Ile Gly Lys Phe Leu Lys Lys Ala Lys Lys Gly Ile Gly Ala Val
1               5                   10                  15

Leu Lys Val Leu Thr Thr Gly
            20

<210> SEQ ID NO 108
<211> LENGTH: 35
<212> TYPE: PRT
<213> ORGANISM: Unknown
<220> FEATURE:
<223> OTHER INFORMATION: TL-ColM

<400> SEQUENCE: 108

Met Glu Thr Leu Thr Val His Ala Pro Ser Pro Ser Thr Asn Leu Pro
1               5                   10                  15

Ser Tyr Gly Asn Gly Ala Phe Ser Leu Ser Ala Pro His Val Pro Gly
            20                  25                  30

Ala Gly Pro
        35

<210> SEQ ID NO 109
<211> LENGTH: 18
<212> TYPE: PRT
<213> ORGANISM: Unknown
<220> FEATURE:
<223> OTHER INFORMATION: SBO

<400> SEQUENCE: 109

Lys Leu Lys Lys Ile Ala Gln Lys Ile Lys Asn Phe Phe Ala Lys Leu
1               5                   10                  15

Val Ala

<210> SEQ ID NO 110
<211> LENGTH: 34
<212> TYPE: PRT
<213> ORGANISM: Limulus polyphemus

<400> SEQUENCE: 110

Gly Phe Lys Leu Lys Gly Met Ala Arg Ile Ser Cys Leu Pro Asn Gly
1               5                   10                  15

Gln Trp Ser Asn Phe Pro Pro Lys Cys Ile Arg Glu Cys Ala Met Val
            20                  25                  30

Ser Ser

<210> SEQ ID NO 111
<211> LENGTH: 18
<212> TYPE: PRT
<213> ORGANISM: Artificial sequence
<220> FEATURE:
<223> OTHER INFORMATION: Synthetic peptide

<400> SEQUENCE: 111

Gly Phe Phe Ile Pro Ala Val Ile Leu Pro Ser Ile Ala Phe Leu Ile
1               5                   10                  15

Val Pro
```

<210> SEQ ID NO 112
<211> LENGTH: 5
<212> TYPE: PRT
<213> ORGANISM: Artificial sequence
<220> FEATURE:
<223> OTHER INFORMATION: Synthetic peptide

<400> SEQUENCE: 112

Phe Phe Val Ala Pro
1               5

<210> SEQ ID NO 113
<211> LENGTH: 13
<212> TYPE: PRT
<213> ORGANISM: unknown
<220> FEATURE:
<223> OTHER INFORMATION: alpha4-helix of T4 lysozyme

<400> SEQUENCE: 113

Pro Asn Arg Ala Lys Arg Val Ile Thr Thr Phe Arg Thr
1               5                   10

<210> SEQ ID NO 114
<211> LENGTH: 27
<212> TYPE: PRT
<213> ORGANISM: Artificial sequence
<220> FEATURE:
<223> OTHER INFORMATION: Synthetic peptide

<400> SEQUENCE: 114

Lys Arg Trp Val Lys Arg Val Lys Arg Val Lys Arg Trp Val Lys Arg
1               5                   10                  15

Val Val Arg Val Val Lys Arg Trp Val Lys Arg
            20                  25

<210> SEQ ID NO 115
<211> LENGTH: 25
<212> TYPE: PRT
<213> ORGANISM: Artificial Sequence
<220> FEATURE:
<223> OTHER INFORMATION: Synthetic peptide; MW2

<400> SEQUENCE: 115

Gly Lys Pro Gly Trp Leu Ile Lys Val Ala Leu Lys Phe Lys Lys Leu
1               5                   10                  15

Ile Arg Arg Pro Leu Lys Arg Leu Ala
            20                  25

<210> SEQ ID NO 116
<211> LENGTH: 4
<212> TYPE: PRT
<213> ORGANISM: Artificial sequence
<220> FEATURE:
<223> OTHER INFORMATION: Synthetic linker

<400> SEQUENCE: 116

Gly Ala Gly Ala
1

<210> SEQ ID NO 117
<211> LENGTH: 8
<212> TYPE: PRT
<213> ORGANISM: Artificial sequence
<220> FEATURE:
<223> OTHER INFORMATION: Synthetic linker

```
<400> SEQUENCE: 117

Gly Ala Gly Ala Gly Ala Gly Ala
1               5

<210> SEQ ID NO 118
<211> LENGTH: 12
<212> TYPE: PRT
<213> ORGANISM: Artificial sequence
<220> FEATURE:
<223> OTHER INFORMATION: Synthetic linker

<400> SEQUENCE: 118

Gly Ala Gly Ala Gly Ala Gly Ala Gly Ala Gly Ala
1               5                   10

<210> SEQ ID NO 119
<211> LENGTH: 6
<212> TYPE: PRT
<213> ORGANISM: Artificial sequence
<220> FEATURE:
<223> OTHER INFORMATION: Synthetic peptide (His-Tag (6x))

<400> SEQUENCE: 119

His His His His His His
1               5

<210> SEQ ID NO 120
<211> LENGTH: 161
<212> TYPE: PRT
<213> ORGANISM: Salmonella phage phi68

<400> SEQUENCE: 120

Ser Asn Arg Asn Ile Ser Asp Asn Gly Ile Lys Phe Thr Ala Ala Phe
1               5                   10                  15

Glu Gly Phe Arg Gly Thr Ala Tyr Arg Ala Thr Lys Asn Glu Lys Tyr
            20                  25                  30

Leu Thr Ile Gly Tyr Gly His Tyr Gly Ala Asp Val Lys Glu Gly Gln
        35                  40                  45

Lys Ile Thr Glu Gly Gln Gly Leu Leu Leu His Lys Asp Met Val
    50                  55                  60

Lys Ala Val Ala Ala Val Asp Ala Val Ala His Pro Pro Leu Asn Gln
65                  70                  75                  80

Ser Gln Phe Asp Ala Met Cys Asp Leu Val Tyr Asn Ala Gly Val Gly
                85                  90                  95

Val Ile Ala Ala Ser Thr Gly Thr Gly Gln Ala Leu Arg Lys Gly Asp
            100                 105                 110

Val Ala Thr Leu Arg Asn Lys Leu Thr Gln Phe His Tyr Gln Asn Gly
        115                 120                 125

Lys Ser Leu Leu Gly Leu Arg Arg Arg Ala Gly Arg Val Ala Leu
    130                 135                 140

Phe Asp Gly Met Leu Trp Gln Gln Ala Glu Ala Ile Gly Arg Gly Ala
145                 150                 155                 160

Lys
```

ENDOLYSIN VARIANT

This application is a national phase application under 35 U.S.C. § 371 of International Application No. PCT/IB2017/053099, filed May 26, 2017, which claims benefit of priority to International Application No. PCT/TH2016/000048, filed May 27, 2016, the entire contents of each of which are hereby incorporated by reference.

BACKGROUND OF THE INVENTION

I. Field of the Invention

The present invention relates to the field of antimicrobial enzymes. In particular, the present invention relates to a polypeptide comprising an amino acid sequence exhibiting at least 90% sequence identity with the sequence of SEQ ID NO:1, with the proviso that the polypeptide does neither comprise the sequence according to SEQ ID NO:2, nor the sequence according to SEQ ID NO:3, nor the sequence according to SEQ ID NO:4. The present invention relates also to nucleic acids encoding an inventive polypeptide, vectors or bacteriophages comprising an inventive nucleic acid as well as host cells comprising an inventive polypeptide, nucleic acid, vector, and/or bacteriophage. Similarly, the present invention relates to compositions comprising a polypeptide, nucleic acid, vector, bacteriophage, and/or host cell according to the present invention.

II. Description of Related Art

Endolysins are peptidoglycan hydrolases encoded by bacteriophages (or bacterial viruses). They are synthesized during late gene expression in the lytic cycle of phage multiplication and mediate the release of progeny virions from infected cells through degradation of the bacterial peptidoglycan. In terms of enzymatic activity they are usually either ß(1,4)-glycosylases (lysozymes), transglycosylases, amidases or endopeptidases. Antimicrobial application of endolysins was already suggested in 1991 by Gasson (GB2243611). Although the killing capacity of endolysins has been known for a long time, the use of these enzymes as antibacterials was ignored due to the success and dominance of antibiotics. Only after the appearance of multiple antibiotic resistant bacteria this simple concept of combating human pathogens with endolysins received interest. A compelling need to develop totally new classes of antibacterial agents emerged and endolysins used as 'enzybiotics'—a hybrid term of 'enzymes' and 'antibiotics'—perfectly met this need. In 2001, Fischetti and coworkers demonstrated for the first time the therapeutic potential of bacteriophage C1 endolysin towards group A streptococci (Nelson et al., 2001). Since then many publications have established endolysins as an attractive and complementary alternative to control bacterial infections, particularly by Gram positive bacteria. Subsequently different endolysins against other Gram positive pathogens such as *Streptococcus pneumoniae* (Loeffler et al., 2001), *Bacillus anthracis* (Schuch et al., 2002), *S. agalactiae* (Cheng et al., 2005) and *Staphylococcus aureus* (Rashel et al, 2007) have proven their efficacy as enzybiotics. Nowadays, the most important challenge of endolysin therapy lies in the insensitivity of Gram-negative bacteria towards the exogenous action of endolysins, since the outer membrane shields the access of endolysins from the peptidoglycan. In 2014, Oliveira et al. (PLoS One, 2014 Oct. 7; 9(10):e108376) published a report about a thermostable *Salmonella* phage endolysin, Lys68, with broad bactericidal properties against Gram-negative pathogens in presence of weak acids.

Gram-negative bacteria possess an outer membrane, with its characteristic asymmetric bilayer as a hallmark. The outer membrane bilayer consists of an inner monolayer containing phospholipids (primarily phosphatidyl ethanolamine) and an outer monolayer that is mainly composed of a single glycolipid, lipopolysaccharide (LPS). There is an immense diversity of LPS structures in the bacterial kingdom and the LPS structure may be modified in response to prevailing environmental conditions. The stability of the LPS layer and interaction between different LPS molecules is mainly achieved by the electrostatic interaction of divalent ions (Mg2+, Ca2+) with the anionic components of the LPS molecule (phosphate groups in the lipid A and the inner core and carboxyl groups of KDO). Furthermore, the dense and ordered packing of the hydrophobic moiety of lipid A, favored by the absence of unsaturated fatty acids, forms a rigid structure with high viscosity. This makes it less permeable for lipophilic molecules and confers additional stability to the outer membrane (OM).

In contrast to Gram-negative bacteria, Gram-positive bacteria do not possess an outer membrane. The cytoplasmic membrane is surrounded by an up to 25 nm thick layer of peptidoglycan (which is only up to 5 nm for Gram-negative bacteria) which forms the cell wall. Main purpose of the cell wall of Gram-positives is to maintain bacterial shape and to counteract the internal bacterial cell pressure. Peptidoglycan, or murein, is a polymer consisting of sugars and amino acids. The sugar component consists of alternating residues of β-(1,4) linked N-acetylglucosamine and N-acetylmuramic acid residues compose the sugar components. A peptide chain of three to five amino acids is attached to the N-acetylmuramic acid. The peptide chain can be cross-linked to the peptide chain of another strand forming a 3D mesh-like layer. The peptide chain may contain D- and L-amino acid residues and the composition may vary for different bacteria.

Meanwhile, new strategies have emerged to utilize also endolysins originating from phages infecting Gram-negative bacterial species to control infections caused by Gram-negative bacteria. For this purpose, endolysins of Gram negative bacteria are fused with, e.g. cationic, amphipathic, hydrophobic or antimicrobial peptides. This type of fusion protein allows overcoming previous problems with the outer membrane of Gram-negative bacteria.

However, despite the advances in the art regarding antibacterial agents, there is still a need in the art for further improvement in the design of such antibacterial agents, in particular due to the increasing resistance to conventional antibiotics.

This problem is solved by the subject-matter as set forth below and in the appended claims.

SUMMARY OF THE INVENTION

In a first aspect the present invention relates to a polypeptide comprising an amino acid sequence exhibiting at least 90%, preferably at least 95%, more preferably at least 97% sequence identity with the sequence of SEQ ID NO:1, wherein SEQ ID NO:1 is characterized by X5 may be any amino acid, preferably I or V,
X13 may be any amino acid, preferably G or S,
X72 may be any amino acid, preferably P, L or S,
X98 may be any amino acid, preferably G or D, with the proviso that the polypeptide does neither comprise the sequence according to SEQ ID NO:2, nor the sequence according to SEQ ID NO:3, nor the sequence according to SEQ ID NO:4.

The inventor of the present invention has surprisingly found that removal of N-terminal and in particular C-terminal portions of the enzyme Lys68 according to SEQ ID NO:2 still yields active enzyme. Moreover, a significant number of mutations can be introduced without loss of activity. In parallel, such mutations can be suited to increase thermal stability, thereby making the enzyme more apt for industrial use.

In a preferred embodiment, the inventive polypeptide comprises an amino acid sequence exhibiting at least 86% sequence identity with the sequence of SEQ ID NO: 5, wherein SEQ ID NO: 5 is characterized by X1 may be absent or any amino acid, in particular M,
X11 may be any amino acid, preferably I or V,
X19 may be any amino acid, preferably G or S,
X78 may be any amino acid, preferably P, L or S,
X104 may be any amino acid, preferably G or D;

with the proviso that the polypeptide does neither comprise the sequence according to SEQ ID NO:2, nor the sequence according to SEQ ID NO:3, nor the sequence according to SEQ ID NO:4.

In another preferred embodiment the inventive polypeptide comprises an amino acid sequence exhibiting at least 80% sequence identity with the sequence of SEQ ID NO: 6, wherein SEQ ID NO: 6 is characterized by X1 may be absent or any amino acid, in particular M,
X11 may be any amino acid, preferably I or V,
X19 may be any amino acid, preferably G or S,
X78 may be any amino acid, preferably P, L or S,
X104 may be any amino acid, preferably G or D,
X134 may be any amino acid, preferably G or C;

with the proviso that the polypeptide does neither comprise the sequence according to SEQ ID NO:2, nor the sequence according to SEQ ID NO:3, nor the sequence according to SEQ ID NO:4.

In a further preferred embodiment, the polypeptide according to the present invention comprises an amino acid sequence exhibiting at least about 80% sequence identity with the sequence of SEQ ID NO:7, wherein SEQ ID NO:7 is characterized by X5 may be any amino acid, preferably I or V,
X13 may be any amino acid, preferably G or S,
X72 may be any amino acid, preferably P, L or S,
X98 may be any amino acid, preferably G or D,
X128 may be any amino acid, preferably G or C, with the proviso that the polypeptide does neither comprise the sequence according to SEQ ID NO:2, nor the sequence according to SEQ ID NO:3, nor the sequence according to SEQ ID NO:4.

In a further preferred embodiment, the polypeptide according to the present invention comprises an amino acid sequence exhibiting at least about 80% sequence identity with the sequence of SEQ ID NO:8, wherein SEQ ID NO:8 is characterized by X5 may be any amino acid, preferably I or V,
X13 may be any amino acid, preferably G or S,
X72 may be any amino acid, preferably P, L or S,
X98 may be any amino acid, preferably G or D,
X128 may be any amino acid, preferably G or C; and
X150 may be any amino acid, preferably A or V;

with the proviso that the polypeptide does neither comprise the sequence according to SEQ ID NO:2, nor the sequence according to SEQ ID NO:3, nor the sequence according to SEQ ID NO:4.

In a particularly preferred embodiment, the polypeptide according to the present invention comprises an amino acid sequence exhibiting at least about 80% sequence identity with the sequence of SEQ ID NO: 9, wherein SEQ ID NO: 9 is characterized by X1 may be absent or any amino acid, in particular M,
X11 may be any amino acid, preferably I or V,
X19 may be any amino acid, preferably G or S,
X78 may be any amino acid, preferably P, L or S,
X104 may be any amino acid, preferably G or D,
X134 may be any amino acid, preferably G or C; and
X156 may be any amino acid, preferably A or V;

with the proviso that the polypeptide does neither comprise the sequence according to SEQ ID NO:2, nor the sequence according to SEQ ID NO:3, nor the sequence according to SEQ ID NO:4.

In a further aspect, the present invention relates to a polypeptide comprising an amino acid sequence exhibiting at least 90% sequence identity with the sequence of SEQ ID NO: 10, wherein SEQ ID NO: 10 is characterized by X2 may be any amino acid, preferably D or N,
X5 may be any amino acid, preferably L, I or V,
X6 may be any amino acid, preferably H or K,
X13 may be any amino acid, preferably G, V or S,
X15 may be any amino acid, preferably R or Q,
X20 may be any amino acid, preferably K or R,
X23 may be any amino acid, preferably K or P,
X24 may be any amino acid, preferably S or N,
X28 may be any amino acid, preferably L or F,
X32 may be any amino acid, preferably Y or F,
X34 may be any amino acid, preferably H or S,
X37 may be any amino acid, preferably A or P,
X38 may be any amino acid, preferably D or H,
X40 may be any amino acid, preferably K or Y,
X49 may be any amino acid, preferably Q or R,
X55 may be any amino acid, preferably H or N,
X56 may be any amino acid, preferably K or R,
X59 may be any amino acid, preferably V, S or A,
X72 may be any amino acid, preferably P, L, T or S,
X81 may be any amino acid, preferably M or V,
X90 may be any amino acid, preferably V, P or A,
X95 may be any amino acid, preferably A or V,
X98 may be any amino acid, preferably G or D,
X108 may be any amino acid, preferably V, I or A,
X109 may be any amino acid, preferably A or S,
X113 may be any amino acid, preferably N or S,
X116 may be any amino acid, preferably S or T;

with the proviso that the polypeptide does neither comprise the sequence according to SEQ ID NO:2, nor the sequence according to SEQ ID NO:3, nor the sequence according to SEQ ID NO:4, nor consists of any of the following sequences: SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, and SEQ ID NO:31.

The inventive polypeptide may comprise additional amino acid sequence elements. For example the inventive polypeptide may additionally comprise at least one amino acid sequence selected from the group consisting of amphipathic peptides, cationic peptides, hydrophobic peptides, naturally occurring antimicrobial peptides, sushi peptides and defensins. Such further peptide can enhance the antibacterial activity of the inventive polypeptide.

In further aspects, the present invention relates to nucleic acids encoding an inventive polypeptide, vectors or bacteriophages comprising an inventive nucleic acid as well as host cells comprising an inventive polypeptide, nucleic acid, vector, and/or bacteriophage.

Finally, the present invention relates in a further aspect also to compositions comprising a polypeptide, nucleic acid, vector, bacteriophage, and/or host cell according to the present invention.

DESCRIPTION OF ILLUSTRATIVE EMBODIMENTS

I. Definitions

The term "polypeptide" as used herein refers in particular to a polymer of amino acid residues linked by peptide bonds in a specific sequence. The amino acid residues of a polypeptide may be modified by e.g. covalent attachments of various groups such as carbohydrates and phosphate. Other substances may be more loosely associated with the polypeptide, such as heme or lipid, giving rise to conjugated polypeptides which are also comprised by the term "polypeptide" as used herein. The term as used herein is intended to encompass also proteins. Thus, the term "polypeptide" also encompasses for example complexes of two or more amino acid polymer chains. The term "polypeptide" does encompass embodiments of polypeptides which exhibit optionally modifications typically used in the art, e.g. biotinylation, acetylation, pegylation, chemical changes of the amino-, SH- or carboxyl-groups (e.g. protecting groups) etc. As will become apparent from the description below, the polypeptide according to the invention may be an artificially engineered polypeptide, which does not exist in this form in nature. Such polypeptide may for example exhibit artificial mutations vis-à-vis a naturally occurring polypeptide or may comprise heterologous sequences, or may be a fragment of a naturally occurring polypeptide, which fragment does not occur in this form in nature. Furthermore, the polypeptide according to the present invention may be a fusion protein, i.e. represent the linkage of at least two amino acid sequences which do not occur in this combination in nature. The term "polypeptide" as used herein is not limited to a specific length of the amino acid polymer chain, but typically the polypeptide will exhibit a length of more than about 125 amino acids. Usually, but not necessarily, a typical polypeptide of the present invention will not exceed about 1000 amino acids in length. The inventive polypeptide may for instance be at most about 750 amino acids long, at most about 500 amino acids long or at most about 300 amino acids long. A possible length range for the inventive polypeptide, without being limited thereto, may thus for example be about 200 to about 750 amino acids, or about 225 to about 600 amino acids, or about 250 to about 350 amino acids.

The term "% sequence identity" is generally understood in the art. Two sequences to be compared are aligned to give a maximum correlation between the sequences. This may include inserting "gaps" in either one or both sequences, to enhance the degree of alignment. A % identity may then be determined over the whole length of each of the sequences being compared (so-called global alignment), that is particularly suitable for sequences of the same or similar length, or over shorter, defined lengths (so-called local alignment), that is more suitable for sequences of unequal length. In the above context, an amino acid sequence having a "sequence identity" of at least, for example, 95% to a query amino acid sequence, is intended to mean that the sequence of the subject amino acid sequence is identical to the query sequence except that the subject amino acid sequence may include up to five amino acid alterations per each 100 amino acids of the query amino acid sequence. In other words, to obtain an amino acid sequence having a sequence of at least 95% identity to a query amino acid sequence, up to 5% (5 of 100) of the amino acid residues in the subject sequence may be inserted or substituted with another amino acid or deleted. Methods for comparing the identity and homology of two or more sequences are well known in the art. The percentage to which two sequences are identical can for example be determined by using a mathematical algorithm. A preferred, but not limiting, example of a mathematical algorithm which can be used is the algorithm of Karlin et a/. (1993), PNAS USA, 90:5873-5877. Such an algorithm is integrated in the BLAST family of programs, e.g. BLAST or NBLAST program (see also Altschul et al., 1990, J. Mol. Biol. 215, 403-410 or Altschul et al. (1997), Nucleic Acids Res, 25:3389-3402), accessible through the home page of the NCBI at world wide web site ncbi.nlm.nih.gov) and FASTA (Pearson (1990), Methods Enzymol. 83, 63-98; Pearson and Lipman (1988), Proc. Natl. Acad. Sci. U. S. A 85, 2444-2448.). Sequences which are identical to other sequences to a certain extent can be identified by these programs. Furthermore, programs available in the Wisconsin Sequence Analysis Package, version 9.1 (Devereux et al, 1984, Nucleic Acids Res., 387-395), for example the programs BESTFIT and GAP, may be used to determine the % identity between two polypeptide sequences. BESTFIT uses the "local homology" algorithm of (Smith and Waterman (1981), J. Mol. Biol. 147, 195-197.) and finds the best single region of similarity between two sequences. If herein reference is made to an amino acid sequence sharing a particular degree of sequence identity to a reference sequence, then said difference in sequence is preferably due to conservative amino acid substitutions. Preferably, such sequence retains the activity of the reference sequence, albeit maybe at a slower (or even faster) rate. In addition, if reference is made herein to a sequence sharing "at least" at certain percentage of sequence identity, then 100% sequence identity are preferably not encompassed.

As used herein, the term "cationic peptide" refers preferably to a peptide having positively charged amino acid residues. Preferably a cationic peptide has a pKa-value of 9.0 or greater. Typically, at least four of the amino acid residues of the cationic peptide can be positively charged, for example, lysine or arginine. "Positively charged" refers to the side chains of the amino acid residues which have a net positive charge at about physiological conditions. The term "cationic peptide" as used herein refers also to polycationic peptides, but also includes cationic peptides which comprise for example less than 20%, preferably less than 10% positively charged amino acid residues.

The term "polycationic peptide", as used herein, refers preferably to a peptide composed of mostly positively charged amino acid residues, in particular lysine and/or arginine residues. A peptide is composed of mostly positively charged amino acid residues if at least about 20, 30, 40, 50, 60, 70, 75, 80, 85, 90, 95 or about 100% of the amino acid residues are positively charged amino acid residues, in particular lysine and/or arginine residues. The amino acid residues being not positively charged amino acid residues can be neutrally charged amino acid residues and/or negatively charged amino acid residues and/or hydrophobic amino acid residues. Preferably the amino acid residues being not positively charged amino acid residues are neutrally charged amino acid residues, in particular serine and/or glycine.

The term, "antimicrobial peptide" (AMP), as used herein, refers preferably to any naturally occurring peptide that has microbicidal and/or microbistatic activity on for example bacteria, viruses, fungi, yeasts, *mycoplasma* and protozoa. Thus, the term "antimicrobial peptide" as used herein refers in particular to any peptide having anti-bacterial, anti-fungal, anti-mycotic, anti-parasitic, anti-protozoal, anti-viral, anti-infectious, anti-infective and/or germicidal, algicidal, amoebicidal, microbicidal, bactericidal, fungicidal, parasiticidal, protozoacidal, protozoicidal properties. Preferred are anti-bacterial peptides. The antimicrobial peptide may be a member of the RNase A super family, a defensin, cathelicidin, granulysin, histatin, psoriasin, dermicidine or hepcidin. The antimicrobial peptide may be naturally occurring in insects, fish, plants, arachnids, vertebrates or mammals. Preferably the antimicrobial peptide may be naturally occurring in insects, fish, plants, arachnids, vertebrates or mammals. Preferably the antimicrobial peptide may be naturally occurring in radish, silk moth, wolf spider, frog, preferably in *Xenopus laevis, Rana* frogs, more preferably in *Rana catesbeiana*, toad, preferably Asian toad *Bufo bufo gargarizans*, fly, preferably in *Drosophila*, more preferably in *Drosophila melanogaster*, in *Aedes aegypti*, in honey bee, bumblebee, preferably in *Bombus pascuorum*, flesh fly, preferably in *Sarcophaga peregrine*, scorpion, horseshoe crab, catfish, preferably in *Parasilurus asotus*, cow, pig, sheep, porcine, bovine, monkey and human. As used herein, an "antimicrobial peptide" (AMP) may in particular be a peptide which is not a cationic peptide, polycationic peptide, amphipathic peptide, sushi peptide, defensins, and hydrophobic peptide, but nevertheless exhibits antimicrobial activity.

The term "sushi peptide", as used herein, refers to complement control proteins (CCP) having short consensus repeats. The sushi module of sushi peptides functions as a protein-protein interaction domain in many different proteins. Peptides containing a Sushi domain have been shown to have antimicrobial activities. Preferably, sushi peptides are naturally occurring peptides.

The term "amphipathic peptide", as used herein, refers to synthetic peptides having both hydrophilic and hydrophobic functional groups. Preferably, the term "amphipathic peptide" as used herein refers to a peptide having a defined arrangement of hydrophilic and hydrophobic groups e.g. amphipathic peptides may be e.g. alpha helical, having predominantly non polar side chains along one side of the helix and polar residues along the rest of its surface.

The term "hydrophobic group", as used herein, refers preferably to chemical groups such as amino acid side chains which are substantially water insoluble, but soluble in an oil phase, with the solubility in the oil phase being higher than that in water or in an aqueous phase. In water, amino acid residues having a hydrophobic side chain interact with one another to generate a non-aqueous environment. Examples of amino acid residues with hydrophobic side chains are valine, isoleucine, leucine, methionine, phenylalanine, tryptophan, cysteine, alanine, tyrosine, and proline residues.

The term "hydrophobic peptide", as used herein, refers to a hydrophobic peptide, which is preferably composed of mostly amino acid residues with hydrophobic groups. Such peptide is preferably composed of mostly hydrophobic amino acid residues, i.e. at least about 20, 30, 40, 50, 60, 70, 75, 80, 85, 90, 95 or at least about 100% of the amino acid residues are hydrophobic amino acid residues. The amino acid residues being not hydrophobic are preferably neutral and preferably not hydrophilic.

The term "comprising", as used herein, shall not be construed as being limited to the meaning "consisting of" (i.e. excluding the presence of additional other matter). Rather, "comprising" implies that optionally additional matter may be present. The term "comprising" encompasses as particularly envisioned embodiments falling within its scope "consisting of" (i.e. excluding the presence of additional other matter) and "comprising but not consisting of" (i.e. requiring the presence of additional other matter), with the former being more preferred.

The use of the word "a" or "an", when used herein, may mean "one," but it is also consistent with the meaning of "one or more," "at least one," and "one or more than one."

II. Polypeptides

As already mentioned, the present invention relates to a polypeptide comprising an amino acid sequence exhibiting at least 90%, preferably at least 95%, more preferably at least 97% sequence identity with the sequence of SEQ ID NO:1, wherein SEQ ID NO:1 is characterized by
X5 of SEQ ID NO:1 may be any amino acid, preferably I or V,
X13 of SEQ ID NO:1 may be any amino acid, preferably G or S,
X72 of SEQ ID NO:1 may be any amino acid, preferably P, L or S,
X98 of SEQ ID NO:1 may be any amino acid, preferably G or D;
with the proviso that the polypeptide does neither comprise the sequence according to SEQ ID NO:2, nor the sequence according to SEQ ID NO:3, nor the sequence according to SEQ ID NO:4.

A person skilled in the art will understand, that when herein reference is made to a sequence, here for example SEQ ID NO:1, and specific residues are referred to with "X", followed by a number, then this is intended to refer to the respective residue position in said sequence. "X5" for example refers to the "X" residue at position 5 of SEQ ID NO:1, counted from the N-terminus of SEQ ID NO:1. Said position need not necessarily reflect the actual position in the polypeptide, which may comprise additional sequence elements, e.g. at its N-terminus. The same applies of course when the same terminology is used for other sequences disclosed herein.

In some embodiments of the invention, at least one of the following four conditions applies for the inventive polypeptide comprising an amino acid sequence exhibiting at least 90% sequence identity with the sequence of SEQ ID NO:1:
i) X5 of SEQ ID NO:1 is I or V, preferably V,
ii) X13 of SEQ ID NO:1 is G or S, preferably S,
iii) X72 of SEQ ID NO:1 is P, L or S, preferably L or S, more preferably S, and/or
iv) X98 of SEQ ID NO:1 is G or D, preferably D.
That "at least one" of these conditions applies includes that, e.g., one, two, three or all four conditions may apply. In some embodiments of the invention, all four conditions apply, i.e. the following applies for the inventive polypeptide comprising an amino acid sequence exhibiting at least 90% sequence identity with the sequence of SEQ ID NO:1:
X5 of SEQ ID NO:1 is I or V, preferably V,
X13 of SEQ ID NO:1 is G or S, preferably S, X72 of SEQ ID NO:1 is P, L or S, preferably L or S, more preferably S, and X98 of SEQ ID NO:1 is G or D, preferably D.

In some embodiments of the invention, at least one of the following four conditions applies for the inventive polypeptide comprising an amino acid sequence exhibiting at least 90% sequence identity with the sequence of SEQ ID NO:1:
  i) X5 of SEQ ID NO:1 is not I,
  ii) X13 of SEQ ID NO:1 is not G,
  iii) X72 of SEQ ID NO:1 is not P, and/or
  iv) X98 of SEQ ID NO:1 is not G.

That "at least one" of these conditions applies includes that, e.g., one, two, three or all four conditions may apply.

In some embodiments of the invention, at least one of the following four conditions applies for the inventive polypeptide comprising an amino acid sequence exhibiting at least 90% sequence identity with the sequence of SEQ ID NO:1:
  i) X5 of SEQ ID NO:1 is V,
  ii) X13 of SEQ ID NO:1 is S,
  iii) X72 of SEQ ID NO:1 is L or S, preferably S, and/or
  iv) X98 of SEQ ID NO:1 is D.

As before, that "at least one" of these conditions applies includes that, e.g., one, two, three or all four conditions may apply. Hence, in some embodiments of the invention all four conditions apply, i.e. the following applies for the inventive polypeptide comprising an amino acid sequence exhibiting at least 90% sequence identity with the sequence of SEQ ID NO:1:

X5 of SEQ ID NO:1 is V,
X13 of SEQ ID NO:1 is S,
X72 of SEQ ID NO:1 is L or S, preferably S, and
X98 of SEQ ID NO:1 is D.

If only one condition applies, it is particularly preferred if this means that X72 of SEQ ID NO:1 is L or S, preferably S. Aside of the situations, where only one of these condition applies (i.e. X5 of SEQ ID NO:1 is V, X13 of SEQ ID NO:1 is S, X72 of SEQ ID NO:1 is L or S, preferably S, or X98 of SEQ ID NO:1 is D), particularly preferred combinations are i) wherein X72 of SEQ ID NO:1 is L and X98 of SEQ ID NO:1 is D, ii) X13 of SEQ ID NO:1 is S and X72 of SEQ ID NO:1 is S, and/or iii) X5 of SEQ ID NO:1 is V and X72 of SEQ ID NO:1 is S.

In particularly preferred embodiments of the invention, the polypeptide comprising an amino acid sequence exhibiting at least 90% sequence identity with the sequence of SEQ ID NO:1 does not exhibit the inactivating mutation E18A described in Oliveira et al. (PLoS One, 2014 Oct. 7; 9(10):e108376) (see SEQ ID NO:4). While an inactivated enzyme may also have utility in various technical applications (e.g. as matching negative control), the active enzymes are still more preferred by the inventor. The polypeptide comprising an amino acid sequence exhibiting at least 90% sequence identity with the sequence of SEQ ID NO:1 does thus preferably not comprise an alanine residue at said position, i.e. does not comprise an amino acid sequence which deviates (inter alia) with a E12A mutation from SEQ ID NO:1. More preferably, the polypeptide comprising an amino acid sequence exhibiting at least 90% sequence identity with the sequence of SEQ ID NO:1 does retain the original glutamate residue (E) at said position, i.e. retains E12 of SEQ ID NO:1 and does not deviate from SEQ ID NO:1 at said position.

The amino acid sequence exhibiting at least 90% sequence identity with the sequence of SEQ ID NO:1 may deviate from SEQ ID NO:1 for example at position 29, i.e. the threonine residue may be replaced by any other amino acid, e.g. an alanine residue. Preferably, deviations from SEQ ID NO:1 are due to conservative amino acid substitutions.

As mentioned above, the present invention relates to a polypeptide comprising an amino acid sequence exhibiting at least about 90% sequence identity with the sequence of SEQ ID NO:1. In more preferred embodiments said amino acid sequence deviates less than 10% from SEQ ID NO: 1. For example, the polypeptide according to the invention may comprise an amino acid sequence exhibiting at least about 95%, at least about 96%, at least about 97%, at least about 98%, at least about 99%, at least about 99.5% or even 100% sequence identity with the sequence of SEQ ID NO:1. In cases where the inventive polypeptide comprises an amino acid sequence exhibiting 100% sequence identity with the sequence of SEQ ID NO:1, the inventive polypeptide comprises the sequence of SEQ ID NO:1. Such embodiment is particularly contemplated by the inventor.

In a further embodiment of the present invention, the polypeptide comprising an amino acid sequence exhibiting at least about 90% sequence identity with the sequence of SEQ ID NO:1 is a polypeptide, which comprises an amino acid sequence exhibiting at least about 86% sequence identity with the sequence of SEQ ID NO: 5, wherein SEQ ID NO: 5 is characterized by X1 of SEQ ID NO: 5 may be absent or any amino acid, in particular M, X11 of SEQ ID NO: 5 may be any amino acid, preferably I or V, X19 of SEQ ID NO: 5 may be any amino acid, preferably G or S, X78 of SEQ ID NO: 5 may be any amino acid, preferably P, L or S, and X104 of SEQ ID NO: 5 may be any amino acid, preferably G or D.

It is understood that for such polypeptide still the general proviso of the present application for polypeptides applies, i.e. that such polypeptide does neither comprise the sequence according to SEQ ID NO:2, nor the sequence according to SEQ ID NO:3, nor the sequence according to SEQ ID NO:4.

In some embodiments of the invention, at least one of the following five conditions applies for the inventive polypeptide comprising an amino acid sequence exhibiting at least 86% sequence identity with the sequence of SEQ ID NO: 5:
  i) X1 of SEQ ID NO: 5 is absent or M, preferably M,
  ii) X11 of SEQ ID NO: 5 is I or V, preferably V,
  iii) X19 of SEQ ID NO: 5 is G or S, preferably S,
  iv) X78 of SEQ ID NO: 5 is P, L or S, preferably L or S, and/or more preferably S,
  v) X104 of SEQ ID NO: 5 is G or D, preferably D.

That "at least one" of these conditions applies includes that, e.g., one, two, three, four or all five conditions may apply. In some embodiments of the invention, all five conditions apply, i.e. the following applies for the inventive polypeptide comprising an amino acid sequence exhibiting at least 86% sequence identity with the sequence of SEQ ID NO: 5:
  i) X1 of SEQ ID NO: 5 is absent or M, preferably M,
  ii) X11 of SEQ ID NO: 5 is I or V, preferably V,
  iii) X19 of SEQ ID NO: 5 is G or S, preferably S,
  iv) X78 of SEQ ID NO: 5 is P, L or S, preferably L or S, more preferably S, and
  v) X104 of SEQ ID NO: 5 is G or D, preferably D.

In some embodiments of the invention, at least one of the following five conditions applies for the inventive polypeptide comprising an amino acid sequence exhibiting at least 86% sequence identity with the sequence of SEQ ID NO: 5:
i) X1 of SEQ ID NO: 5 is absent,
ii) X11 of SEQ ID NO: 5 is not I,
iii) X19 of SEQ ID NO: 5 is not G,
iv) X78 of SEQ ID NO: 5 is not P, and/or
v) X104 of SEQ ID NO: 5 is not G.

That "at least one" of these conditions applies includes that, e.g., one, two, three, four or all five conditions may apply.

In some embodiments of the invention, at least one of the following five conditions applies for the inventive polypeptide comprising an amino acid sequence exhibiting at least 86% sequence identity with the sequence of SEQ ID NO: 5:
i) X1 of SEQ ID NO: 5 is M,
ii) X11 of SEQ ID NO: 5 is V,
iii) X19 of SEQ ID NO: 5 is S,
iv) X78 of SEQ ID NO: 5 is L or S, preferably S, and/or
v) X104 of SEQ ID NO: 5 is D.

As before, that "at least one" of these conditions applies includes that, e.g., one, two, three, four or all five conditions may apply. Hence, in some embodiments of the invention all five conditions apply, i.e. the following applies for the inventive polypeptide comprising an amino acid sequence exhibiting at least 86% sequence identity with the sequence of SEQ ID NO: 5:
i) X1 of SEQ ID NO: 5 is M,
ii) X11 of SEQ ID NO: 5 is V,
iii) X19 of SEQ ID NO: 5 is S,
iv) X78 of SEQ ID NO: 5 is L or S, preferably S, and
v) X104 of SEQ ID NO: 5 is D.

If only one condition applies, it is particularly preferred if this means that X78 of SEQ ID NO: 5 is L or S, preferably S. Aside of the situations, where only one of these condition applies (i.e. X1 of SEQ ID NO: 5 is M, X11 of SEQ ID NO: 5 is V, X19 of SEQ ID NO: 5 is S, X78 of SEQ ID NO: 5 is L or S, preferably S, or X104 of SEQ ID NO: 5 is D), particularly preferred combinations are wherein at least i) X78 of SEQ ID NO: 5 is L and X104 of SEQ ID NO: 5 is D, ii) X19 of SEQ ID NO: 5 is S and X78 of SEQ ID NO: 5 is S, and/or iii) X11 of SEQ ID NO: 5 is V and X78 of SEQ ID NO: 5 is S.

If the inventive polypeptide comprises one or more amino acid residues N-terminal of the amino acid sequence exhibiting at least 86% sequence identity with the sequence of SEQ ID NO: 5, then it is preferred that X1 of SEQ ID NO: 5 is not M, i.e. absent or any other amino acid. In the alternative constellation, i.e. where the inventive polypeptide does not comprise one or more amino acid residues N-terminal of the amino acid sequence exhibiting at least 86% sequence identity with the sequence of SEQ ID NO: 5, it is preferred if X1 of SEQ ID NO: 5 is M, in particular if the polypeptide is to be expressed by recombinant means.

In particularly preferred embodiments of the invention, the polypeptide comprising an amino acid sequence exhibiting at least 86% sequence identity with the sequence of SEQ ID NO: 5 does again not exhibit the inactivating mutation E18A described in Oliveira et al. (PLoS One, 2014 Oct. 7; 9(10):e108376) (see SEQ ID NO:4). The polypeptide comprising an amino acid sequence exhibiting at least 86% sequence identity with the sequence of SEQ ID NO: 5 does thus preferably not comprise an alanine residue at said position, i.e. does not comprise an amino acid sequence which deviates (inter alia) with a E18A mutation from SEQ ID NO: 5. More preferably, the polypeptide comprising an amino acid sequence exhibiting at least 86% sequence identity with the sequence of SEQ ID NO: 5 does retain the original glutamate residue (E) at said position, i.e. retains E18 of SEQ ID NO: 5 and does not deviate from SEQ ID NO: 5 at said position.

The amino acid sequence exhibiting at least 86% sequence identity with the sequence of SEQ ID NO: 5 may deviate from SEQ ID NO: 5 for example at position 35, i.e. the threonine residue may be replaced by any other amino acid, e.g. an alanine residue. Another preferred region in which the polypeptide may deviate from the sequence of SEQ ID NO: 5 are for example residues 1 to 6 of SEQ ID NO: 5. Preferably, deviations from SEQ ID NO: 5 are due to conservative amino acid substitutions.

As mentioned above, the present invention relates to a polypeptide comprising an amino acid sequence exhibiting at least about 86% sequence identity with the sequence of SEQ ID NO: 5. In more preferred embodiments said amino acid sequence deviates less than 14% from SEQ ID NO: 5. For example, the polypeptide according to the invention may comprise an amino acid sequence exhibiting at least about 90%, at least about 95%, at least about 96%, at least about 97%, at least about 98%, at least about 99%, at least about 99.5% or even 100% sequence identity with the sequence of SEQ ID NO: 5. In cases where the inventive polypeptide comprises an amino acid sequence exhibiting 100% sequence identity with the sequence of SEQ ID NO: 5, the inventive polypeptide comprises the sequence of SEQ ID NO: 5. Such embodiment is particularly contemplated by the inventor.

In a further embodiment of the present invention, the polypeptide comprising an amino acid sequence exhibiting at least about 90% sequence identity with the sequence of SEQ ID NO:1 is a polypeptide, which comprises an amino acid sequence exhibiting at least about 80% sequence identity with the sequence of SEQ ID NO: 6, wherein SEQ ID NO: 6 is characterized by
X1 of SEQ ID NO: 6 may be absent or any amino acid, in particular M,
X11 of SEQ ID NO: 6 may be any amino acid, preferably I or V,
X19 of SEQ ID NO: 6 may be any amino acid, preferably G or S,
X78 of SEQ ID NO: 6 may be any amino acid, preferably P, L or S,
X104 of SEQ ID NO: 6 may be any amino acid, preferably G or D, and
X134 of SEQ ID NO: 6 may be any amino acid, preferably G or C.

It is again understood that for such polypeptide still the general proviso of the present application for polypeptides applies, i.e. that such polypeptide does neither comprise the sequence according to SEQ ID NO:2, nor the sequence according to SEQ ID NO:3, nor the sequence according to SEQ ID NO:4.

In some embodiments of the invention, at least one of the following six conditions applies for the inventive polypeptide comprising an amino acid sequence exhibiting at least 80% sequence identity with the sequence of SEQ ID NO: 6:
i) X1 of SEQ ID NO: 6 is absent or M, preferably M,
ii) X11 of SEQ ID NO: 6 is I or V, preferably V,
iii) X19 of SEQ ID NO: 6 is G or S, preferably S,
iv) X78 of SEQ ID NO: 6 is P, L or S, preferably L or S, more preferably S,
v) X104 of SEQ ID NO: 6 is G or D, preferably D, and/or
vi) X134 of SEQ ID NO: 6 is G or C, preferably C.

That "at least one" of these conditions applies includes that, e.g., one, two, three, four, five, or all six conditions may apply. In some embodiments of the invention, all six conditions apply, i.e. the following applies for the inventive polypeptide comprising an amino acid sequence exhibiting at least 80% sequence identity with the sequence of SEQ ID NO: 6:
  i) X1 of SEQ ID NO: 6 is absent or M, preferably M,
  ii) X11 of SEQ ID NO: 6 is I or V, preferably V,
  iii) X19 of SEQ ID NO: 6 is G or S, preferably S,
  iv) X78 of SEQ ID NO: 6 is P, L or S, preferably L or S, more preferably S,
  v) X104 of SEQ ID NO: 6 is G or D, preferably D, and
  vi) X134 of SEQ ID NO: 6 is G or C, preferably C.

In some embodiments of the invention, at least one of the following six conditions applies for the inventive polypeptide comprising an amino acid sequence exhibiting at least 80% sequence identity with the sequence of SEQ ID NO: 6:
  i) X1 of SEQ ID NO: 6 is absent,
  ii) X11 of SEQ ID NO: 6 is not I,
  iii) X19 of SEQ ID NO: 6 is not G,
  iv) X78 of SEQ ID NO: 6 is not P,
  v) X104 of SEQ ID NO: 6 is not G, and/or
  vi) X134 of SEQ ID NO: 6 is not G.
That "at least one" of these conditions applies includes that, e.g., one, two, three, four, five or all six conditions may apply.

In some embodiments of the invention, at least one of the following six conditions applies for the inventive polypeptide comprising an amino acid sequence exhibiting at least 80% sequence identity with the sequence of SEQ ID NO: 6:
  i) X1 of SEQ ID NO: 6 is M,
  ii) X11 of SEQ ID NO: 6 is V,
  iii) X19 of SEQ ID NO: 6 is S,
  iv) X78 of SEQ ID NO: 6 is L or S, preferably S,
  v) X104 of SEQ ID NO: 6 is D, and/or
  vi) X134 of SEQ ID NO: 6 is C.
As before, that "at least one" of these conditions applies includes that, e.g., one, two, three, four, five or all six conditions may apply. Hence, in some embodiments of the invention all six conditions apply, i.e. the following applies for the inventive polypeptide comprising an amino acid sequence exhibiting at least 80% sequence identity with the sequence of SEQ ID NO: 6:
  i) X1 of SEQ ID NO: 6 is M,
  ii) X11 of SEQ ID NO: 6 is V,
  iii) X19 of SEQ ID NO: 6 is S,
  iv) X78 of SEQ ID NO: 6 is L or S, preferably S,
  v) X104 of SEQ ID NO: 6 is D, and
  vi) X134 of SEQ ID NO: 6 is C.
If only one condition applies, it is particularly preferred if this means that X78 of SEQ ID NO: 6 is L or S, preferably S. Aside of the situations, where only one of these condition applies (i.e. X1 of SEQ ID NO: 6 is M, X11 of SEQ ID NO: 6 is V, X19 of SEQ ID NO: 6 is S, X78 of SEQ ID NO: 6 is L or S, preferably S, X104 of SEQ ID NO: 6 is D or X134 of SEQ ID NO: 6 is C), particularly preferred combinations are wherein at least i) X78 of SEQ ID NO: 6 is L and X104 of SEQ ID NO: 6 is D, ii) X19 of SEQ ID NO: 6 is S and X78 of SEQ ID NO: 6 is S, iii) X11 of SEQ ID NO: 6 is V and X78 of SEQ ID NO: 6 is S, and/or iv) X78 of SEQ ID NO: 6 is S and X134 of SEQ ID NO: 6 is C.

If the inventive polypeptide comprises one or more amino acid residues N-terminal of the amino acid sequence exhibiting at least 80% sequence identity with the sequence of SEQ ID NO: 6, then it is preferred that X1 of SEQ ID NO: 6 is not M, i.e. absent or any other amino acid. In the alternative constellation, i.e. where the inventive polypeptide does not comprise one or more amino acid residues N-terminal of the amino acid sequence exhibiting at least 80% sequence identity with the sequence of SEQ ID NO: 6, it is preferred if X1 of SEQ ID NO: 6 is M, in particular if the polypeptide is to be expressed by recombinant means.

In particularly preferred embodiments of the invention, the polypeptide comprising an amino acid sequence exhibiting at least 80% sequence identity with the sequence of SEQ ID NO: 6 does again not exhibit the inactivating mutation E18A described in Oliveira et al. (PLoS One, 2014 Oct. 7; 9(10):e108376) (see SEQ ID NO:4). The polypeptide comprising an amino acid sequence exhibiting at least 80% sequence identity with the sequence of SEQ ID NO: 6 does thus preferably not comprise an alanine residue at said position, i.e. does not comprise an amino acid sequence which deviates (inter alia) with a E18A mutation from SEQ ID NO: 6. More preferably, the polypeptide comprising an amino acid sequence exhibiting at least 80% sequence identity with the sequence of SEQ ID NO: 6 does retain the original glutamate residue (E) at said position, i.e. retains E18 of SEQ ID NO: 6 and does not deviate from SEQ ID NO: 6 at said position.

The amino acid sequence exhibiting at least 80% sequence identity with the sequence of SEQ ID NO: 6 may deviate from SEQ ID NO: 6 for example at position 35, i.e. the threonine residue may be replaced by any other amino acid, e.g. an alanine residue. Other preferred regions in which the polypeptide may deviate from the sequence of SEQ ID NO: 6 are for example residues 1 to 6 of SEQ ID NO: 6 and/or residues 133 to 148 of SEQ ID NO: 6. Preferably, deviations from SEQ ID NO: 6 are due to conservative amino acid substitutions.

As mentioned above, the present invention relates to a polypeptide comprising an amino acid sequence exhibiting at least about 80% sequence identity with the sequence of SEQ ID NO: 6. In more preferred embodiments said amino acid sequence deviates less than 20% from SEQ ID NO: 6. For example, the polypeptide according to the invention may comprise an amino acid sequence exhibiting at least about 85%, at least about 90%, at least about 95%, at least about 96%, at least about 97%, at least about 98%, at least about 99%, at least about 99.5% or even 100% sequence identity with the sequence of SEQ ID NO: 6. In cases where the inventive polypeptide comprises an amino acid sequence exhibiting 100% sequence identity with the sequence of SEQ ID NO: 6, the inventive polypeptide comprises the sequence of SEQ ID NO: 6. Such embodiment is particularly contemplated by the inventor.

In a further embodiment of the present invention, the polypeptide comprising an amino acid sequence exhibiting at least about 90% sequence identity with the sequence of SEQ ID NO:1 is a polypeptide, which comprises an amino acid sequence exhibiting at least about 80% sequence identity with the sequence of SEQ ID NO:7, wherein SEQ ID NO:7 is characterized by
  X5 of SEQ ID NO:7 may be any amino acid, preferably I or V,
  X13 of SEQ ID NO:7 may be any amino acid, preferably G or S,
  X72 of SEQ ID NO:7 may be any amino acid, preferably P, L or S,
  X98 of SEQ ID NO:7 may be any amino acid, preferably G or D, and
  X128 of SEQ ID NO:7 may be any amino acid, preferably G or C.
It is again understood that for such polypeptide still the general proviso of the present application for polypeptides applies, i.e. that such polypeptide does neither comprise the sequence according to SEQ ID NO:2, nor the sequence according to SEQ ID NO:3, nor the sequence according to SEQ ID NO:4.

In some embodiments of the invention, at least one of the following five conditions applies for the inventive polypeptide comprising an amino acid sequence exhibiting at least 80% sequence identity with the sequence of SEQ ID NO:7:
i) X5 of SEQ ID NO:7 is I or V, preferably V,
ii) X13 of SEQ ID NO:7 is G or S, preferably S,
iii) X72 of SEQ ID NO:7 is P, L or S, preferably L or S, more preferably S,
iv) X98 of SEQ ID NO:7 is G or D, preferably D, and/or
v) X128 of SEQ ID NO:7 is G or C, preferably C.

That "at least one" of these conditions applies includes that, e.g., one, two, three, four or all five conditions may apply. In some embodiments of the invention, all five conditions apply, i.e. the following applies for the inventive polypeptide comprising an amino acid sequence exhibiting at least 80% sequence identity with the sequence of SEQ ID NO:7:
i) X5 of SEQ ID NO:7 is I or V, preferably V,
ii) X13 of SEQ ID NO:7 is G or S, preferably S,
iii) X72 of SEQ ID NO:7 is P, L or S, preferably L or S, more preferably S,
iv) X98 of SEQ ID NO:7 is G or D, preferably D, and
v) X128 of SEQ ID NO:7 is G or C, preferably C.

In some embodiments of the invention, at least one of the following five conditions applies for the inventive polypeptide comprising an amino acid sequence exhibiting at least 80% sequence identity with the sequence of SEQ ID NO:7:
i) X5 of SEQ ID NO:7 is not I,
ii) X13 of SEQ ID NO:7 is not G,
iii) X72 of SEQ ID NO:7 is not P,
iv) X98 of SEQ ID NO:7 is not G, and/or
v) X128 of SEQ ID NO:7 is not G.

That "at least one" of these conditions applies includes that, e.g., one, two, three, four or all five conditions may apply.

In some embodiments of the invention, at least one of the following five conditions applies for the inventive polypeptide comprising an amino acid sequence exhibiting at least 80% sequence identity with the sequence of SEQ ID NO:7:
i) X5 of SEQ ID NO:7 is V,
ii) X13 of SEQ ID NO:7 is S,
iii) X72 of SEQ ID NO:7 is L or S, preferably S,
iv) X98 of SEQ ID NO:7 is D, and/or
v) X128 of SEQ NO:7 is C.

As before, that "at least one" of these conditions applies includes that, e.g., one, two, three, four or all five conditions may apply. Hence, in some embodiments of the invention all five conditions apply, i.e. the following applies for the inventive polypeptide comprising an amino acid sequence exhibiting at least 80% sequence identity with the sequence of SEQ ID NO:7:
i) X5 of SEQ ID NO:7 is V,
ii) X13 of SEQ ID NO:7 is S,
iii) X72 of SEQ ID NO:7 is L or S, preferably S,
iv) X98 of SEQ ID NO:7 is D, and
v) X128 of SEQ NO:7 is C.

If only one condition applies, it is particularly preferred if this means that X72 of SEQ ID NO:7 is L or S, preferably S. Aside of the situations, where only one of these condition applies (i.e. X5 of SEQ ID NO:7 is V, X13 of SEQ ID NO:7 is S, X72 of SEQ ID NO:7 is L or S, preferably S, X98 of SEQ ID NO:7 is D or X128 of SEQ ID NO:7 is C), particularly preferred combinations are wherein at least i) X72 of SEQ ID NO:7 is L and X98 of SEQ ID NO:7 is D, ii) X13 of SEQ ID NO:7 is S and X72 of SEQ ID NO:7 is S, iii) X5 of SEQ ID NO:7 is V and X72 of SEQ ID NO:7 is S, and/or iv) X72 of SEQ ID NO:7 is S and X128 of SEQ ID NO:7 is C.

In particularly preferred embodiments of the invention, the polypeptide comprising an amino acid sequence exhibiting at least 80% sequence identity with the sequence of SEQ ID NO:7 does again not exhibit the inactivating mutation E18A described in Oliveira et al. (PLoS One, 2014 Oct. 7; 9(10):e108376) (see SEQ ID NO:4). The polypeptide comprising an amino acid sequence exhibiting at least 80% sequence identity with the sequence of SEQ ID NO:7 does thus preferably not comprise an alanine residue at said position, i.e. does not comprise an amino acid sequence which deviates (inter alia) with a E12A mutation from SEQ ID NO:7. More preferably, the polypeptide comprising an amino acid sequence exhibiting at least 80% sequence identity with the sequence of SEQ ID NO:7 does retain the original glutamate residue (E) at said position, i.e. retains E12 of SEQ ID NO:7 and does not deviate from SEQ ID NO:7 at said position.

The amino acid sequence exhibiting at least 80% sequence identity with the sequence of SEQ ID NO:7 may deviate from SEQ ID NO:7 for example at position 29, i.e. the threonine residue may be replaced by any other amino acid, e.g. an alanine residue. Other preferred regions in which the polypeptide may deviate from the sequence of SEQ ID NO:7 are for example residues 127 to 142 of SEQ ID NO:7. Preferably, deviations from SEQ ID NO:7 are due to conservative amino acid substitutions.

As mentioned above, the present invention relates to a polypeptide comprising an amino acid sequence exhibiting at least about 80% sequence identity with the sequence of SEQ ID NO:7. In more preferred embodiments said amino acid sequence deviates less than 20% from SEQ ID NO:7. For example, the polypeptide according to the invention may comprise an amino acid sequence exhibiting at least about 85%, at least about 90%, at least about 95%, at least about 96%, at least about 97%, at least about 98%, at least about 99%, at least about 99.5% or even 100% sequence identity with the sequence of SEQ ID NO:7. In cases where the inventive polypeptide comprises an amino acid sequence exhibiting 100% sequence identity with the sequence of SEQ ID NO:7, the inventive polypeptide comprises the sequence of SEQ ID NO:7. Such embodiment is particularly contemplated by the inventor.

In a further embodiment of the present invention, the polypeptide comprising an amino acid sequence exhibiting at least about 90% sequence identity with the sequence of SEQ ID NO:1 is a polypeptide, which comprises an amino acid sequence exhibiting at least about 80% sequence identity with the sequence of SEQ ID NO:8, wherein SEQ ID NO:8 is characterized by
X5 of SEQ ID NO:8 may be any amino acid, preferably I or V,
X13 of SEQ ID NO:8 may be any amino acid, preferably G or S,
X72 of SEQ ID NO:8 may be any amino acid, preferably P, L or S,
X98 of SEQ ID NO:8 may be any amino acid, preferably G or D,
X128 of SEQ ID NO:8 may be any amino acid, preferably G or C, and
X150 of SEQ ID NO:8 may be any amino acid, preferably A or V.

It is again understood that for such polypeptide still the general proviso of the present application for polypeptides applies, i.e. that such polypeptide does neither comprise the sequence according to SEQ ID NO:2, nor the sequence according to SEQ ID NO:3, nor the sequence according to SEQ ID NO:4.

In some embodiments of the invention, at least one of the following six conditions applies for the inventive polypeptide comprising an amino acid sequence exhibiting at least 80% sequence identity with the sequence of SEQ ID NO:8:
  i) X5 of SEQ ID NO:8 is I or V, preferably V,
  ii) X13 of SEQ ID NO:8 is G or S, preferably S,
  iii) X72 of SEQ ID NO:8 is P, L or S, preferably L or S, more preferably S,
  iv) X98 of SEQ ID NO:8 is G or D, preferably D,
  v) X128 of SEQ ID NO:8 is G or C, preferably C, and/or
  vi) X150 of SEQ ID NO:8 is A or V, preferably V.

That "at least one" of these conditions applies includes that, e.g., one, two, three, four, five or all six conditions may apply. In some embodiments of the invention, all six conditions apply, i.e. the following applies for the inventive polypeptide comprising an amino acid sequence exhibiting at least 80% sequence identity with the sequence of SEQ ID NO:8:
  i) X5 of SEQ ID NO:8 is I or V, preferably V,
  ii) X13 of SEQ ID NO:8 is G or S, preferably S,
  iii) X72 of SEQ ID NO:8 is P, L or S, preferably L or S, more preferably S,
  iv) X98 of SEQ ID NO:8 is G or D, preferably D,
  v) X128 of SEQ ID NO:8 is G or C, preferably C, and
  vi) X150 of SEQ ID NO:8 is A or V, preferably V.

In some embodiments of the invention, at least one of the following six conditions applies for the inventive polypeptide comprising an amino acid sequence exhibiting at least 80% sequence identity with the sequence of SEQ ID NO:8:
  i) X5 of SEQ ID NO:8 is not I,
  ii) X13 of SEQ ID NO:8 is not G,
  iii) X72 of SEQ ID NO:8 is not P,
  iv) X98 of SEQ ID NO:8 is not G,
  v) X128 of SEQ ID NO:8 is not G, and/or
  vi) X150 of SEQ ID NO:8 is not A.

That "at least one" of these conditions applies includes that, e.g., one, two, three, four, five or all six conditions may apply.

In some embodiments of the invention, at least one of the following six conditions applies for the inventive polypeptide comprising an amino acid sequence exhibiting at least 80% sequence identity with the sequence of SEQ ID NO:8:
  i) X5 of SEQ ID NO:8 is V,
  ii) X13 of SEQ ID NO:8 is S,
  iii) X72 of SEQ ID NO:8 is L or S, preferably S,
  iv) X98 of SEQ ID NO:8 is D,
  v) X128 of SEQ ID NO:8 is C, and/or
  vi) X150 of SEQ ID NO:8 is V.

As before, that "at least one" of these conditions applies includes that, e.g., one, two, three, four, five or all six conditions may apply. Hence, in some embodiments of the invention all six conditions apply, i.e. the following applies for the inventive polypeptide comprising an amino acid sequence exhibiting at least 80% sequence identity with the sequence of SEQ ID NO:8:
  i) X5 of SEQ ID NO:8 is V,
  ii) X13 of SEQ ID NO:8 is S,
  iii) X72 of SEQ ID NO:8 is L or S, preferably S,
  iv) X98 of SEQ ID NO:8 is D,
  v) X128 of SEQ NO:8 is C, and
  vi) X150 of SEQ ID NO:8 is V.

If only one condition applies, it is particularly preferred if this means that X72 of SEQ ID NO:8 is L or S, preferably S. Aside of the situations, where only one of these condition applies (i.e. X5 of SEQ ID NO:8 is V, X13 of SEQ ID NO:8 is S, X72 of SEQ ID NO:8 is L or S, preferably S, X98 of SEQ ID NO:8 is D or X128 of SEQ ID NO:8 is C, X150 of SEQ ID NO:8 is V), particularly preferred combinations are wherein at least i) X72 of SEQ ID NO:8 is L and X98 of SEQ ID NO:8 is D, ii) X13 of SEQ ID NO:8 is S and X72 of SEQ ID NO:8 is S, iii) X5 of SEQ ID NO:8 is V and X72 of SEQ ID NO:8 is S, iv) X72 of SEQ ID NO:8 is S and X128 of SEQ ID NO:8 is C, and/or v) X72 of SEQ ID NO:8 is L, X98 of SEQ ID NO:8 is D and X150 of SEQ ID NO:8 is V.

In particularly preferred embodiments of the invention, the polypeptide comprising an amino acid sequence exhibiting at least 80% sequence identity with the sequence of SEQ ID NO:8 does again not exhibit the inactivating mutation E18A described in Oliveira et al. (PLoS One, 2014 Oct. 7; 9(10):e108376) (see SEQ ID NO:4). The polypeptide comprising an amino acid sequence exhibiting at least 80% sequence identity with the sequence of SEQ ID NO:8 does thus preferably not comprise an alanine residue at said position, i.e. does not comprise an amino acid sequence which deviates (inter alia) with a E12A mutation from SEQ ID NO:8. More preferably, the polypeptide comprising an amino acid sequence exhibiting at least 80% sequence identity with the sequence of SEQ ID NO:8 does retain the original glutamate residue (E) at said position, i.e. retains E12 of SEQ ID NO:8 and does not deviate from SEQ ID NO:8 at said position.

The amino acid sequence exhibiting at least 80% sequence identity with the sequence of SEQ ID NO:8 may deviate from SEQ ID NO:8 for example at position 29, i.e. the threonine residue may be replaced by any other amino acid, e.g. an alanine residue. Other preferred regions in which the polypeptide may deviate from the sequence of SEQ ID NO:8 are for example residues 127 to 156 of SEQ ID NO:8. Preferably, deviations from SEQ ID NO:8 are due to conservative amino acid substitutions.

As mentioned above, the present invention relates to a polypeptide comprising an amino acid sequence exhibiting at least about 80% sequence identity with the sequence of SEQ ID NO:8. In more preferred embodiments said amino acid sequence deviates less than 20% from SEQ ID NO:8. For example, the polypeptide according to the invention may comprise an amino acid sequence exhibiting at least about 85%, at least about 90%, at least about 95%, at least about 96%, at least about 97%, at least about 98%, at least about 99%, at least about 99.5% or even 100% sequence identity with the sequence of SEQ ID NO:8. In cases where the inventive polypeptide comprises an amino acid sequence exhibiting 100% sequence identity with the sequence of SEQ ID NO:8, the inventive polypeptide comprises the sequence of SEQ ID NO:8. Such embodiment is particularly contemplated by the inventor.

In a further embodiment of the present invention, the polypeptide comprising an amino acid sequence exhibiting at least about 90% sequence identity with the sequence of SEQ ID NO:1 is a polypeptide, which comprises an amino acid sequence exhibiting at least about 80% sequence identity with the sequence of SEQ ID NO: 9, wherein SEQ ID NO: 9 is characterized by
  X1 of SEQ ID NO: 9 may be absent or any amino acid, in particular M,
  X11 of SEQ ID NO: 9 may be any amino acid, preferably I or V,
  X19 of SEQ ID NO: 9 may be any amino acid, preferably G or S, X78 of SEQ ID NO: 9 may be any amino acid, preferably P, L or S, X104 of SEQ ID NO: 9 may be any amino acid, preferably G or D, X134 of SEQ ID NO: 9 may be any amino acid, preferably G or C, and X156 of SEQ ID NO: 9 may be any amino acid, preferably A or V.

It is again understood that for such polypeptide still the general proviso of the present application for polypeptides applies, i.e. that such polypeptide does neither comprise the sequence according to SEQ ID NO:2, nor the sequence according to SEQ ID NO:3, nor the sequence according to SEQ ID NO:4.

In some embodiments of the invention, at least one of the following seven conditions applies for the inventive polypeptide comprising an amino acid sequence exhibiting at least 80% sequence identity with the sequence of SEQ ID NO: 9:
  i) X1 of SEQ ID NO: 9 is absent or M, preferably M,
  ii) X11 of SEQ ID NO: 9 is I or V, preferably V,
  iii) X19 of SEQ ID NO: 9 is G or S, preferably S,
  iv) X78 of SEQ ID NO: 9 is P, L or S, preferably L or S, more preferably S,
  v) X104 of SEQ ID NO: 9 is G or D, preferably D,
  vi) X134 of SEQ ID NO: 9 is G or C, preferably C, and/or
  vii) X156 of SEQ ID NO: 9 is A or V.

That "at least one" of these conditions applies includes that, e.g., one, two, three, four, five, six or all seven conditions may apply. In some embodiments of the invention, all seven conditions apply, i.e. the following applies for the inventive polypeptide comprising an amino acid sequence exhibiting at least 80% sequence identity with the sequence of SEQ ID NO: 9:
  i) X1 of SEQ ID NO: 9 is absent or M, preferably M,
  ii) X11 of SEQ ID NO: 9 is I or V, preferably V,
  iii) X19 of SEQ ID NO: 9 is G or S, preferably S,
  iv) X78 of SEQ ID NO: 9 is P, L or S, preferably L or S, more preferably S,
  v) X104 of SEQ ID NO: 9 is G or D, preferably D,
  vi) X134 of SEQ ID NO: 9 is G or C, preferably C, and
  vii) X156 of SEQ ID NO: 9 is A or V.

In some embodiments of the invention, at least one of the following seven conditions applies for the inventive polypeptide comprising an amino acid sequence exhibiting at least 80% sequence identity with the sequence of SEQ ID NO: 9:
  i) X1 of SEQ ID NO: 9 is absent,
  ii) X11 of SEQ ID NO: 9 is not I,
  iii) X19 of SEQ ID NO: 9 is not G,
  iv) X78 of SEQ ID NO: 9 is not P,
  v) X104 of SEQ ID NO: 9 is not G,
  vi) X134 of SEQ ID NO: 9 is not G, and/or
  vii) X156 of SEQ ID NO: 9 is not A.

That "at least one" of these conditions applies includes that, e.g., one, two, three, four, five, six or all seven conditions may apply.

In some embodiments of the invention, at least one of the following seven conditions applies for the inventive polypeptide comprising an amino acid sequence exhibiting at least 80% sequence identity with the sequence of SEQ ID NO: 9:
  i) X1 of SEQ ID NO: 9 is M,
  ii) X11 of SEQ ID NO: 9 is V,
  iii) X19 of SEQ ID NO: 9 is S,
  iv) X78 of SEQ ID NO: 9 is L or S, preferably S,
  v) X104 of SEQ NO: 9 is D,
  vi) X134 of SEQ ID NO: 9 is C, and/or
  vii) X156 of SEQ ID NO: 9 is V.

As before, that "at least one" of these conditions applies includes that, e.g., one, two, three, four, five, six or all seven conditions may apply. Hence, in some embodiments of the invention all seven conditions apply, i.e. the following applies for the inventive polypeptide comprising an amino acid sequence exhibiting at least 80% sequence identity with the sequence of SEQ ID NO: 9:
  i) X1 of SEQ ID NO: 9 is M,
  ii) X11 of SEQ ID NO: 9 is V,
  iii) X19 of SEQ ID NO: 9 is S,
  iv) X78 of SEQ ID NO: 9 is L or S, preferably S,
  v) X104 of SEQ NO: 9 is D,
  vi) X134 of SEQ ID NO: 9 is C and
  vii) X156 of SEQ ID NO: 9 is V.

If only one condition applies, it is particularly preferred if this means that X78 of SEQ ID NO: 9 is L or S, preferably S. Aside of the situations, where only one of these condition applies (i.e. X1 of SEQ ID NO: 9 is M, X11 of SEQ ID NO: 9 is V, X19 of SEQ ID NO: 9 is S, X78 of SEQ ID NO: 9 is L or S, preferably S, X104 of SEQ ID NO: 9 is D, X134 of SEQ ID NO: 9 is C, or X156 of SEQ ID NO: 9 is V), particularly preferred combinations are wherein at least i) X78 of SEQ ID NO: 9 is L and X104 of SEQ ID NO: 9 is D, ii) X19 of SEQ ID NO: 9 is S and X78 of SEQ ID NO: 9 is S, iii) X11 of SEQ ID NO: 9 is V and X78 of SEQ ID NO: 9 is S, iv) X78 of SEQ ID NO: 9 is S and X134 of SEQ ID NO: 9 is C, and/or v) X78 of SEQ ID NO: 9 is L, X104 of SEQ ID NO: 9 is D and X156 of SEQ ID NO: 9 is V.

If the inventive polypeptide comprises one or more amino acid residues N-terminal of the amino acid sequence exhibiting at least 80% sequence identity with the sequence of SEQ ID NO: 9, then it is preferred that X1 of SEQ ID NO: 9 is not M, i.e. absent or any other amino acid. In the alternative constellation, i.e. where the inventive polypeptide does not comprise one or more amino acid residues N-terminal of the amino acid sequence exhibiting at least 80% sequence identity with the sequence of SEQ ID NO: 9, it is preferred if X1 of SEQ ID NO: 9 is M, in particular if the polypeptide is to be expressed by recombinant means.

In particularly preferred embodiments of the invention, the polypeptide comprising an amino acid sequence exhibiting at least 80% sequence identity with the sequence of SEQ ID NO: 9 does again not exhibit the inactivating mutation E18A described in Oliveira et al. (PLoS One, 2014 Oct. 7; 9(10):e108376) (see SEQ ID NO:4). The polypeptide comprising an amino acid sequence exhibiting at least 80% sequence identity with the sequence of SEQ ID NO: 9 does thus preferably not comprise an alanine residue at said position, i.e. does not comprise an amino acid sequence which deviates (inter alia) with a E18A mutation from SEQ ID NO: 9. More preferably, the polypeptide comprising an amino acid sequence exhibiting at least 80% sequence identity with the sequence of SEQ ID NO: 9 does retain the original glutamate residue (E) at said position, i.e. retains E18 of SEQ ID NO: 9 and does not deviate from SEQ ID NO: 9 at said position.

The amino acid sequence exhibiting at least 80% sequence identity with the sequence of SEQ ID NO: 9 may deviate from SEQ ID NO: 9 for example at position 35, i.e. the threonine residue may be replaced by any other amino acid, e.g. an alanine residue. Other preferred regions in which the polypeptide may deviate from the sequence of SEQ ID NO: 9 are for example residues 1 to 6 of SEQ ID NO: 9 and/or residues 133 to 162 of SEQ ID NO: 9.

Preferably, deviations from SEQ ID NO: 9 are due to conservative amino acid substitutions.

As mentioned above, the present invention relates to a polypeptide comprising an amino acid sequence exhibiting at least about 80% sequence identity with the sequence of SEQ ID NO: 9. In more preferred embodiments said amino acid sequence deviates less than 20% from SEQ ID NO: 9. For example, the polypeptide according to the invention may comprise an amino acid sequence exhibiting at least about 85%, at least about 90%, at least about 95%, at least about 96%, at least about 97%, at least about 98%, at least about 99%, at least about 99.5% or even 100% sequence identity with the sequence of SEQ ID NO: 9. In cases where the inventive polypeptide comprises an amino acid sequence exhibiting 100% sequence identity with the sequence of SEQ ID NO: 9, the inventive polypeptide comprises the sequence of SEQ ID NO: 9. Such embodiment is particularly contemplated by the inventor.

The present invention relates to polypeptides exhibiting at least a certain level of sequence identity to a given fragment sequence of Lys68 enzyme. Possible mutations, which do not negatively impact function of the enzyme, can be derived for example from the sequences of highly similar enzymes of Lys67 enzyme such as AFO12350.1 (SEQ ID NO:11), A0A0K1Y7J0 (SEQ ID NO:12), YP_224045.1 (SEQ ID NO:13), AFO12459.1 (SEQ ID NO:14), YP_009322827.1 (SEQ ID NO:15), WP_076927521.1 (SEQ ID NO:16), WP_076917165.1 (SEQ ID NO:17), WP_016047076.1 (SEQ ID NO:18), AFO70790.1 (SEQ ID NO:19), WP_076915447.1 (SEQ ID NO:20), AGF87755.1 (SEQ ID NO:21), YP_009009975.1 (SEQ ID NO:22), YP_001110823.1 (SEQ ID NO:23), YP_008239773.1 (SEQ ID NO:24), YP_008767061.1 (SEQ ID NO:25), WP_034086662.1 (SEQ ID NO:26), APM00295.1 (SEQ ID NO:27), YP_007010505.1 (SEQ ID NO:28), APU02985.1 (SEQ ID NO:29), YP_009280144.1 (SEQ ID NO:30), and YP_009035189.1 (SEQ ID NO:31).

In this context, the present invention does also relate a polypeptide comprising an amino acid sequence exhibiting at least 90% sequence identity with the sequence of SEQ ID NO: 10, wherein SEQ ID NO: 10 is characterized by
X2 may be any amino acid, preferably D or N,
X5 may be any amino acid, preferably L, I or V,
X6 may be any amino acid, preferably H or K,
X13 may be any amino acid, preferably G, V or S,
X15 may be any amino acid, preferably R or Q,
X20 may be any amino acid, preferably K or R,
X23 may be any amino acid, preferably K or P,
X24 may be any amino acid, preferably S or N,
X28 may be any amino acid, preferably L or F,
X32 may be any amino acid, preferably Y or F,
X34 may be any amino acid, preferably H or S,
X37 may be any amino acid, preferably A or P,
X38 may be any amino acid, preferably D or H,
X40 may be any amino acid, preferably K or Y,
X49 may be any amino acid, preferably Q or R,
X55 may be any amino acid, preferably H or N,
X56 may be any amino acid, preferably K or R,
X59 may be any amino acid, preferably V, S or A,
X72 may be any amino acid, preferably P, L, T or S,
X81 may be any amino acid, preferably M or V,
X90 may be any amino acid, preferably V, P or A,
X95 may be any amino acid, preferably A or V,
X98 may be any amino acid, preferably G or D,
X108 may be any amino acid, preferably V, I or A,
X109 may be any amino acid, preferably A or S,
X113 may be any amino acid, preferably N or S,
X116 may be any amino acid, preferably S or T;
with the proviso that the polypeptide does neither comprise the sequence according to SEQ ID NO:2, nor the sequence according to SEQ ID NO:3, nor the sequence according to SEQ ID NO:4, nor consists of any of the following sequences: SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, and SEQ ID NO:31. Preferably, the polypeptide comprises the amino acid sequence according to SEQ ID NO: 10. It is also preferred, that the polypeptide does not comprise any of the following sequences: SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, and SEQ ID NO:31. Preferably such polypeptide comprises S or L, preferably S, at the position corresponding to X72.

Examples for inventive polypeptides are for instance polypeptides comprising SEQ ID NO:32, SEQ ID NO:33 or SEQ ID NO:34, as always with the proviso that such polypeptide does neither comprise the sequence according to SEQ ID NO:2, nor the sequence according to SEQ ID NO:3, nor the sequence according to SEQ ID NO:4. Other examples for inventive polypeptides are for instance polypeptides comprising SEQ ID NO:35, SEQ ID NO:36, SEQ ID NO:37, SEQ ID NO:38, SEQ ID NO:39, or SEQ ID NO:40.

A polypeptide according to the present invention exhibits preferably the activity of a peptidoglycan degrading enzyme, i.e. is capable of degrading bacterial peptidoglycan. Typically a polypeptide of the present invention will be capable of degrading the peptidoglycan of bacteria of Gram-negative bacteria, such as *Salmonella* sp. bacteria. The peptidoglycan degrading activity on gram negative bacteria can be measured by assays well known in the art, e.g. by muralytic assays in which the outer membrane of gram negative bacteria is permeabilized or removed (e.g. with chloroform) to allow the putative enzyme access to the peptidoglycan layer. If the enzyme is active, degradation of the peptidoglycan layer will lead to a drop of turbidity, which can be measured photometrically (see for example Briers et al., *J. Biochem. Biophys Methods* 70: 531-533, (2007).

A polypeptide according to the present invention may comprise additionally at least one further amino acid sequence stretch selected from the group consisting of amphipathic peptide, cationic peptide, polycationic peptide, hydrophobic peptide, or naturally occurring antimicrobial peptide, like sushi peptide and defensin. This additional at least one amino acid sequence stretch may in principle be present at any position in the inventive polypeptide, but is preferably present at the termini, i.e. in the N- or C-terminal region of the inventive polypeptide. Such additional amino acid sequence stretch may be fused directly, or via a peptide linker, to the rest of the polypeptide. It is understood that if one (or more) such additional amino acid sequence stretches according to the present invention are present in the N-terminal region of the inventive polypeptide, then there may be further additional amino acids on the N-terminus of the additional amino acid sequence stretch. Preferably these comprise the amino acid methionine (Met), or the sequence methionine, glycine and serine (Met-Gly-Ser).

This at least one additional amino acid sequence stretch preferably has the function to lead the inventive polypeptide through the outer membrane of bacteria and may have activity or may have no or only low activity when administered without being fused to the polypeptide of the invention. The function to guide the polypeptide through the outer membrane of Gram-negative bacteria is caused by the outer membrane or LPS disrupting, permeabilising or destabilizing activity of said amino acid sequence stretches.

Such outer membrane or LPS disrupting or permeabilising or destabilizing activity of these amino acid sequence stretches may be determined in a method as follows: The bacteria cells to be treated are cultured in liquid medium or on agar plates. Then the bacteria cell concentration in the liquid medium is determined photometrically at $OD_{600}$ nm or the colonies on the agar plates are counted, respectively. Now, the bacteria cells in liquid medium or on the plates are treated with a polypeptide according to the present invention exhibiting at least one additional amino acid sequence stretch as defined herein. After incubation the bacteria cell concentration in the liquid medium is determined photometrically at $OD_{600}$ nm or the colonies on the agar plates are counted again. If the protein exhibits such outer membrane or LPS disrupting or permeabilising or destabilizing activity, the bacteria cells are lysed due to the treatment with the polypeptide and thus, the bacteria cell concentration in the liquid medium or the number of the bacteria colonies on the agar plate is reduced. Thus, the reduction in bacteria cell concentration or in the number of bacteria colonies after treatment with the protein is indicative for an outer membrane or LPS disrupting or permeabilising or destabilizing activity of the polypeptide.

Especially preferred are cationic and/or polycationic amino acid sequence stretches comprising at least one motive according to SEQ ID NO:41 (KRKKRK). In particular cationic amino acid sequence stretches comprising at least 2, 3, 4, 5, 6, 7, 8, 9, 10, 11, 12, 13, 14, 15, 16 or 17 motives according to SEQ ID NO: 41 (KRKKRK) are preferred. More preferred are cationic peptide stretches comprising at least one KRK motive (lys-arg-lys), preferable at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 KRK motives.

In another preferred embodiment of the present invention the cationic amino acid sequence stretch comprises beside the positively charged amino acid residues, in particular lysine and/or arginine residues, neutrally charged amino acid residues, in particular glycine and/or serine residues. Preferred are cationic amino acid sequence stretches consisting of about 70% to about 100%, or about 80% to about 95%, or about 85% to about 90% positively charged amino acid residues, in particular lysine, arginine and/or histidine residues, more preferably lysine and/or arginine residues and of about 0% to about 30%, or about 5% to about 20%, or about 10% to about 20% neutrally charged amino acid residues, in particular glycine and/or serine residues. Preferred are amino acid sequence stretches consisting of about 4% to about 8% serine residues, of about 33% to about 36% arginine residues and of about 56% to about 63% lysine residues. Especially preferred are amino acid sequence stretches comprising at least one motive according to SEQ ID NO: 42 (KRXKR), wherein X is any other amino acid than lysine, arginine and histidine. Especially preferred are polypeptide stretches comprising at least one motive according to SEQ ID NO: 43 (KRSKR). More preferred are cationic stretches comprising at least about 2, 3, 4, 5, 6, 7, 8, 9, 10, 11, 12, 13, 14, 15, 16, 17, 18, 19 or at least about 20 motives according to SEQ ID NO: 42 (KRXKR) or SEQ ID NO: 43 (KRSKR).

Also preferred are amino acid sequence stretches consisting of about 9 to about 16% glycine residues, of about 4 to about 11% serine residues, of about 26 to about 32% arginine residues and of about 47 to about 55% lysine residues. Especially preferred are amino acid sequence stretches comprising at least one motive according to SEQ ID NO: 44 (KRGSG). More preferred are cationic stretches comprising at least about 2, 3, 4, 5, 6, 7, 8, 9, 10, 11, 12, 13, 14, 15, 16, 17, 18, 19 or at least bout 20 motives according to SEQ ID NO: 44 (KRGSG).

In another preferred embodiment of the present invention such cationic amino acid sequence stretch comprises beside the positively charged amino acid residues, in particular lysine and/or arginine residues, hydrophobic amino acid residues, in particular valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues. Preferred are cationic amino acid sequence stretches consisting of about 70% to about 100%, or about 80% to about 95%, or about 85% to about 90% positively charged amino acid residues, in particular lysine and/or arginine residues and of about 0% to about 30%, or about 5% to about 20%, or about 10% to about % hydrophobic amino acid residues, valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues. Examples for cationic and polycationic amino acid sequence stretches are listed in the following table:

TABLE 1

| amino acid sequence stretch | length | SEQ ID NO: |
|---|---|---|
| KRKKRK | 6 | 41 |
| KRKKRKKRK | 9 | 45 |
| RRRRRRRRR | 9 | 46 |
| KKKKKKKK | 8 | 47 |
| KRKKRKKRKK | 10 | 48 |
| KRKKRKKRKKRK | 12 | 49 |
| KRKKRKKRKKRKKR | 14 | 50 |
| KKKKKKKKKKKKKKKK | 16 | 51 |

TABLE 1-continued

| amino acid sequence stretch | length | SEQ ID NO: |
|---|---|---|
| KRKKRKKRKKRKKRKKRK | 18 | 52 |
| KRKKRKKRKKRKKRKKRKK | 19 | 53 |
| RRRRRRRRRRRRRRRRRRR | 19 | 54 |
| KKKKKKKKKKKKKKKKKKK | 19 | 55 |
| KRKKRKKRKRSKRKKRKKRK | 20 | 56 |
| KRKKRKKRKRSKRKKRKKRKK | 21 | 57 |
| KRKKRKKRKKRKKRKRKKRK | 21 | 58 |
| KRKKRKKRKRGSGKRKKRKKRK | 22 | 59 |
| KRKKRKKRKRGSGSGKRKKRKKRK | 24 | 60 |
| KRKKRKKRKKRKKRKKRKKRKKRKK | 25 | 61 |
| KRKKRKKRKRSKRKKRKKRKRSKRKKRKKRK | 31 | 62 |
| KRKKRKKRKRGSGSGKRKKRKKRKRGSGSGKRKKRKKRK | 38 | 63 |
| KRKKRKKRKKRKKRKKRKKRKKRKKRKKRKKRKKRKKRK | 39 | 64 |
| KRKKRKKRKRSKRKKRKKRKRSKRKKRKKRKRSKRKKRKKRK | 42 | 65 |

In a further aspect of the present invention at least one of the additional amino acid sequence stretches is an antimicrobial peptide, which comprises a positive net charge and around 50% hydrophobic amino acids. The antimicrobial peptides are amphipathic with a length of about 12 to about 50 amino acid residues. The antimicrobial peptides are naturally occurring in insects, fish, plants, arachnids, vertebrates or mammals. Preferably the antimicrobial peptide may be naturally occurring in radish, silk moth, wolf spider, frog, preferably in *Xenopus laevis*, *Rana* frogs, more preferably in *Rana catesbeiana*, toad, preferably Asian toad *Bufo bufo gargarizans*, fly, preferably in *Drosophila*, more preferably in *Drosophila melanogaster*, in *Aedes aegypti*, in honey bee, bumblebee, preferably in *Bombus pascuorum*, flesh fly, preferably in *Sarcophaga peregrine*, scorpion, horseshoe crab, catfish, preferably in *Parasilurus asotus*, cow, pig, sheep, porcine, bovine, monkey and human.

In another preferred embodiment of the present invention the antimicrobial amino acid sequence stretches consist of about 0% to about 5%, or about 0% to about 35%, or about 10% to about 35% or about 15% to about 45%, or about 20% to about 45% positively charged amino acid residues, in particular lysine and/or arginine residues and of about 50% to about 80%, or about 60% to about 80%, or about 55% to about 75%, or about 70% to about 90% hydrophobic amino acid residues, valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues.

In another preferred embodiment of the present invention the antimicrobial amino acid sequence stretches consist of about 4% to about 58% positively charged amino acid residues, in particular lysine and/or arginine residues and of about 33% to about 89% hydrophobic amino acid residues, valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues.

Examples for antimicrobial amino acid sequences which may be used in carrying out the present invention are listed in the following table.

TABLE 2

| Peptide | Sequence | SEQ ID NO |
|---|---|---|
| LL-37 | LLGDFFRKSKEKIGKEFKRIVQRIKDFLRNLVPRTES | 66 |
| SMAP-29 | RGLRRLGRKIAHGVKKYGPTVLRIIRIAG | 67 |
| Indolicidin | ILPWKWPWWPWRR | 68 |
| Protegrin | RGGRLCYCRRRFCVCVGR | 69 |
| Cecropin P1 | SWLSKTAKKLENSAKKRISEGIAIAIQGGPR | 70 |
| Magainin | GIGKFLHSAKKFGKAFVGEIMNS | 71 |
| Pleurocidin | GWGSFFKKAAHVGKHVGKAALTHYL | 72 |
| Cecropin A | GGLKKLGKKLEGAGKRVFNAAEKALPVVAGAKAL | 73 |

TABLE 2-continued

| Peptide | Sequence | SEQ ID NO |
|---|---|---|
| (A.aegypti) | RK | |
| Cecropin A (D. melanogaster) | GWLKKIGKKIERVGQHTRDATIQGLGIPQQAANV AATARG | 74 |
| Buforin II | TRSSRAGLQFPVGRVHRLLRK | 75 |
| Sarcotoxin IA | GWLKKIGKKIERVGQHTRDATIQGLGIAQQAANV AATAR | 76 |
| Apidaecin | ANRPVYIPPPRPPHPRL | 77 |
| Ascaphine 5 | GIKDWIKGAAKKLIKTVASHIANQ | 78 |
| Nigrocine 2 | GLLSKVLGVGKKVLCGVSGLVC | 79 |
| Pseudin 1 | GLNTLKKVFQGLHEAIKLINNHVQ | 80 |
| Ranalexin | FLGGLIVPAMICAVTKKC | 81 |
| Melittin | GIGAVLKVLTTGLPALISWIKRKRQQ | 82 |
| Lycotoxin 1 | IWLTALKFLGKHAAKKLAKQQLSKL | 83 |
| Parasin 1 | KGRGKQGGKVRAKAKTRSS | 84 |
| Buforin I | AGRGKQGGKVRAKAKTRSSRAGLQFPVGRVHRLL RKGNY | 85 |
| Dermaseptin 1 | ALWKTMLKKLGTMALHAGKAALGAAADTISQGTQ | 86 |
| Bactenecin 1 | RLCRIVVIRVCR | 87 |
| Thanatin | GSKKPVPIIYCNRRTGKCQRM | 88 |
| Brevinin 1T | VNPIILGVLPKVCLITKKC | 89 |
| Ranateurin 1 | SMLSVLKNLGKVGLGFVACKINIKQC | 90 |
| Esculentin 1 | GIFSKLGRKKIKNLLISGLKNVGKEVGMDVVRTG IKIAGCKIKGEC | 91 |
| Tachyplesin | RWCFRVCYRGICYRKCR | 92 |
| Androctonin | RSVCRQIKICRRRGGCYYKCTNRPY | 93 |
| alpha-defensin | DCYCRIPACIAGERRYGTCIYQGRLWAFCC | 94 |
| beta-defensin | NPVSCVRNKGICVPIRCPGSMKQIGTCVGRAVKC CRKK | 95 |
| theta-defensin | GFCRCLCRRGVCRCICTR | 96 |
| defensin (sapecin A) | ATCDLLSGTGINHSACAAHCLLRGNRGGYCNGKA VCVCRN | 97 |
| Thionin (crambin) | TTCCPSIVARSNFNVCRIPGTPEAICATYTGCII IPGATCPGDYAN | 98 |
| defensin from radish | QKLCQRPSGTWSGVCGNNNACKNQCIRLEKARHG SCNYVFPAHCICYFPC | 99 |
| Drosomycin | DCLSGRYKGPCAVWDNETCRRVCKEEGRSSGHCS PSLKCWCEGC | 100 |
| Hepcidin | DTHFPICIFCCGCCHRSKCGMCCKT | 101 |
| Bac 5 | RFRPPIRRPPIRPPFYPPFRPPIRPPIFPPIRPP FRPPLGRPFP | 102 |
| PR-39 | RRRPRPPYLPRPRPPPFPPRLPPRIPPGFPPRF PPRFP | 103 |
| Pyrrhocoricin | VDKGSYLPRPTPPRPIYNRN | 104 |
| Histatin 5 | DSHAKRHHGYKRKFHEKHHSHRGY | 105 |

TABLE 2-continued

| Peptide | Sequence | SEQ ID NO |
|---|---|---|
| ECP19 | RPPQFTRAQWFAIQHISLN | 106 |
| MSI-594 | GIGKFLKKAKKGIGAVLKVLTTG | 107 |
| TL-ColM | METLTVHAPSPSTNLPSYGNGAFSLSAPHVPGAGP | 108 |
| SBO | KLKKIAQKIKNFFAKLVA | 109 |

In a further aspect of the present invention at least one of the additional amino acid sequence stretches may be a sushi peptide which is described by Ding J L, Li P, Ho B Cell Mol Life Sci. 2008 April; 65(7-8):1202-19. The Sushi peptides: structural characterization and mode of action against Gram-negative bacteria. Especially preferred is the sushi 1 peptide according to SEQ ID NO: 110.

Preferred sushi peptides are sushi peptides S1 and S3 and multiples thereof; FASEB J. 2000 September; 14(12):1801-13.

In a further aspect of the present invention at least one of the additional amino acid sequence stretches is a hydrophobic peptide, which comprises at least 90% of the hydrophobic amino acid residues of valine, isoleucine, leucine, methionine, phenylalanine, tryptophan, cysteine, alanine, tyrosine, proline and/or glycine. In another preferred embodiment the hydrophobic peptide fused to the protein of the invention consists of about 90% to about 95%, or of about 90% to about 100%, or of about 95% to about 100% of the hydrophobic amino acid residues of valine, isoleucine, leucine, methionine, phenylalanine, tryptophan, cysteine, alanine, tyrosine, proline and/or glycine.

Preferred hydrophobic peptides are Walmagh1 having the amino acid sequence according to SEQ ID NO: 111 and the hydrophobic peptide having the amino acid sequence Phe-Phe-Val-Ala-Pro (SEQ ID NO: 112).

In a further aspect of the present invention at least one of the additional amino acid sequence stretches is an amphipathic peptide, which comprises one or more of the positively charged amino acid residues of lysine, arginine and/or histidine, combined to one or more of the hydrophobic amino acid residues of valine, isoleucine, leucine, methionine, phenylalanine, tryptophan, cysteine, alanine, tyrosine, proline and/or glycine. Side chains of the amino acid residues are oriented in order that cationic and hydrophobic surfaces are clustered at opposite sides of the peptide. Preferably, more than about 30, 40, 50, 60 or 70% of the amino acids in said peptide are positively charged amino acids. Preferably, more than about 30, 40, 50, 60 or 70%, of the amino acid residues in said peptide are hydrophobic amino acid residues. Advantageously, the amphipathic peptide is present at the N-terminal or the C-terminal end of the polypeptide according to the present invention.

In another embodiment of the invention, the amphipathic peptide consists of at least 5, more preferably at least of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or at least 50 amino acid residues. In a preferred embodiment at least about 30, 40, 50, 60 or 70% of said amino acid residues of the amphipathic peptide are either arginine or lysine residues and/or at least about 30, 40, 50, 60 or 70% of said amino acid residues of the amphipathic peptide are of the hydrophobic amino acids valine, isoleucine, leucine, methionine, phenylalanine, tryptophan, cysteine, alanine, tyrosine, proline and/or glycine.

In another preferred embodiment of the present invention the amphipathic peptide stretch comprises beside the positively charged amino acid residues, in particular lysine and/or arginine residues, hydrophobic amino acid residues, in particular valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues. Preferred are amphipathic peptide stretches consisting of about 10% to about 50%, or about 20% to about 50%, or about 30% to about 45% or about 5% to about 30% positively charged amino acid residues, in particular lysine and/or arginine residues and of about 50% to about 85%, or about 50% to about 90%, or about 55% to about 90%, or about 60% to about 90%, or about 65% to about 90% hydrophobic amino acid residues, valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues. In another preferred embodiment amphipathic peptide stretches consisting of 12% to about 50% positively charged amino acid residues, in particular lysine and/or arginine residues and of about 50% to about 85% hydrophobic amino acid residues, valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues.

Preferred amphipathic peptides are α4-helix of T4 lysozyme according to SEQ ID NO: 113 and WLBU2-Variant having the amino acid sequence according to SEQ ID NO: 114 and Walmagh 2 according to SEQ ID NO: 115.

The optional additional amino acid sequence stretches as specified above consist preferably of at least 5, more preferably at least of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or at least 100 amino acid residues. Especially preferred are those additional amino acid sequence stretches consisting of about 5 to about 100 amino acid residues, about 5 to about 50 or about 5 to about 30 amino acid residues. More preferred are peptide stretches consisting of about 6 to about 42 amino acid residues, about 6 to about 39 amino acid residues, about 6 to about 38 amino acid residues, about 6 to about 31 amino acid residues, about 6 to about 25 amino acid residues, about 6 to about 24 amino acid residues, about 6 to about 22 amino acid residues, about 6 to about 21 amino acid residues, about 6 to about 20 amino acid residues, about 6 to about 19 amino acid residues, about 6 to about 16 amino acid residues, about 6 to about 14 amino acid residues, about 6 to about 12 amino acid residues, about 6 to about 10 amino acid residues or about 6 to about 9 amino acid residues.

In a preferred embodiment the inventive polypeptide comprises at least one amino acid sequence stretch selected from the group consisting of KRK and SEQ ID NOs: 41-115. Preferably, the inventive polypeptide comprises at least one amino acid sequence stretch selected from the group consisting of KRK and SEQ ID NOs: 41-115 (see in particular tables 1 and 2), and an amino acid sequence selected from any one of SEQ ID NO: 1 and SEQ ID NO: 5 to 40, wherein preferably the amino acid sequence stretches, are fused to the N- and/or C-terminus of the amino acid sequence selected from the group consisting of SEQ ID NO: 1 and SEQ ID NO: 5 to 40.

The additional amino acid sequence stretch of the polypeptide according to the present invention may be linked to the rest of the enzyme by intervening additional amino acid residues e.g. due to cloning reasons. Alternatively, the additional amino acid sequence stretches may be directly linked to the rest of the enzyme sequence without intervening linker sequences. The additional amino acid sequences, if more than one present in the inventive polypeptide and positioned on the same terminus of the enzyme, may likewise be linked to each other by additional intervening amino acid residues or may be directly joined to each other.

Preferably, said intervening additional amino acid residues may not be recognized and/or cleaved by proteases. Preferably said additional amino acid sequences are linked to each other and/or to the enzyme by at least 1, 2, 3, 4, 5, 6, 7, 8, 9 or 10 additional intervening amino acid residues.

In a preferred embodiment the at least one additional amino acid sequence stretch is linked to the rest of the inventive polypeptide, preferably at the N- or C-terminus of the polypeptide according to the present invention, by the additional intervening amino acid residues glycine, serine and serine (Gly-Ser-Ser), glycine, alanine, glycine and alanine (Gly-Ala-Gly-Ala; SEQ ID NO:116), glycine, alanine, glycine, alanine, glycine and alanine (Gly-Ala-Gly-Ala-Gly-Ala-Gly-Ala; SEQ ID NO:117) or glycine, alanine, glycine, alanine, glycine, alanine, glycine, alanine, glycine, alanine, glycine and alanine (Gly-Ala-Gly-Ala-Gly-Ala-Gly-Ala-Gly-Ala-Gly-Ala; SEQ ID NO:118).

Aside of the enzymatic domain (i.e. a domain having the activity of degrading the peptidoglycan of Gram-negative bacteria, such as SEQ ID NO:1), and the optional additional amino acid sequence stretches, as defined herein, the inventive polypeptide may of course also comprise other amino acid sequence elements, e.g. one or more tags, e.g. a His-tag, Strep-tag, Avi-tag, Myc-tag, Gst-tag, JS-tag, cystein-tag, FLAG-tag or other tags known in the art, thioredoxin, maltose binding proteins (MBP) etc.

In this context, the inventive polypeptide, preferably having the ability of degrading the peptidoglycan layer of Gram negative bacteria such as *Salmonella* bacteria, may additional comprise a tag e.g. for purification. Preferred is a $His_6$-tag (SEQ ID NO: 119), preferably at the C-terminus and/or the N-terminus of the polypeptide according to the present invention. Said tag can be linked to the polypeptide by additional amino acid residues e.g. due to cloning reasons. Preferably said tag can be linked to the protein by at least 1, 2, 3, 4, 5, 6, 7, 8, 9 or 10 additional amino acid residues. Preferably said additional amino acid residues may not be recognized and/or cleaved by proteases. In a preferred embodiment the inventive polypeptide comprises a $His_6$-tag at its C-terminus linked to the polypeptide by the additional amino acid residues lysine and glycine (Lys-Gly) or leucine and glutamic acid (Leu-Glu). Preferably, said additional amino acid residues may be not recognized or cleaved by proteases. In another preferred embodiment the inventive polypeptide comprises a $His_6$-tag at its N-terminus linked to the polypeptide by the additional amino acid residues lysine and glycine (Lys-Gly) or leucine and glutamic acid (Leu-Glu). In another preferred embodiment the polypeptide comprises a $His_6$-tag at its N- and C-terminus linked to the polypeptide by the additional amino acid residues lysine and glycine (Lys-Gly) or leucine and glutamic acid (Leu-Glu).

A polypeptide according to the present invention can be produced by standard means known in the art, e.g. by recombinant expression of nucleic acids encoding the respective polypeptide in appropriate host cells. If the inventive polypeptide comprises for example additionally amino acid sequence stretches or tags etc., such fusion proteins may be produced by linking the required individual nucleic acid sequences using standard cloning techniques as described e.g. by Sambrook et al. 2001, Molecular Cloning: A Laboratory Manual. Such a polypeptide may be produced likewise with methods known in the art, e.g., in recombinant DNA expression systems.

III. Nucleic Acids, Vectors, Bacteriophages and Host Cells

The present invention does also relate to nucleic acids encoding one or more inventive polypeptide of the present invention. The inventive nucleic acid may take all forms conceivable for a nucleic acid. In particular the nucleic acids according to the present invention may be RNA, DNA or hybrids thereof. They may be single-stranded or double-stranded. The may have the size of small transcripts or of entire genomes, such as a bacteriophage genome. As used herein, a nucleic acid encoding one or more inventive polypeptides of the present invention may be a nucleic acid reflecting the sense strand. Likewise, the antisense strand is also encompassed. The nucleic acid may encompass a heterologous promotor for expression of the inventive polypeptide.

In a further aspect the present invention relates to a vector comprising a nucleic acid according to the present invention. Such vector may for example be an expression vector allowing for expression of an inventive polypeptide. Said expression may be constitutive or inducible. The vector may also be a cloning vector comprising the nucleic acid sequence of the current invention for cloning purposes.

The present invention does also relate to a bacteriophage comprising an inventive nucleic acid.

The present invention does also relate to (isolated) host cells comprising a polypeptide, nucleic acid, vector, or bacteriophage according to the present invention. The host cells may be selected in particular from the group consisting of bacterial cells and yeast cells. Where appropriate, other suitable host cells may be immortalized cell lines, e.g. of mammalian (in particular human) origin.

IV. Compositions

In a further aspect the present invention relates to a composition comprising a polypeptide according to the present invention, a nucleic acid according to the present invention, a vector according to the present invention, a bacteriophage according to the present invention and/or a host cell according to the present invention.

A composition according to the present invention may be a pharmaceutical composition comprising a pharmaceutical acceptable diluent, excipient or carrier.

BRIEF DESCRIPTION OF THE FIGURES

In the following a brief description of the appended FIGURE will be given. The FIGURE is intended to illustrate the present invention in more detail. However, it is not intended to limit the scope of the invention to these specific examples.

FIG. 1: illustrates the muralytic activity of polypeptides according to Lys68(1-132) (SEQ ID NO:32), Lys68(1-148) (SEQ ID NO:33) and Lys68(7-162) (SEQ ID NO:34). Buffer served as control. X-Axis: minutes. Y-Axis: $OD_{600}$.

V. Examples

In the following, specific examples illustrating various embodiments and aspects of the invention are presented. However, the present invention shall not to be limited in scope by the specific embodiments described herein. Indeed, various modifications of the invention in addition to those described herein will become readily apparent to those skilled in the art from the foregoing description, accompanying FIGURE and the examples below. All such modifications fall within the scope of the appended claims.

Example 1: Truncated Lys68 Endolysin does Still Exhibit Activity

Lys68 is a globular endolysin, i.e. does not exhibit an apparent domain structure with an enzymatic domain and a cell wall binding domain, as encountered for various other endolysins. The inventor hypothesized, that Lys68 endolysin may nonetheless exhibit a core region responsible for enzymatic activity and tested this hypothesis with truncated versions of Lys68, namely Lys68(1-132) (SEQ ID NO:32), Lys68(1-148) (SEQ ID NO:33) and Lys68(7-162) (SEQ ID NO:34).

Briefly, the following experiment was carried out: Exponentially growing P. aeruginosa cells were harvested by centrifugation and subsequently resuspended in 0.05 M Tris/HCl pH 7.7 buffer saturated with chloroform. This cell suspension was incubated for 45 minutes at room temperature. Afterwards, cells were washed with 20 mM HEPES pH 7.4 and finally adjusted to an OD600 of ca. 1.5 with 20 mM HEPES pH 7.4. In order to test the muralytic activity, 270 µl of chloroform treated cells were mixed with 30 µl of purified variants of Lys68 in a 96 well plate and the OD600 was monitored in a microplate reader.

The result is shown in FIG. 1. All constructs showed activity.

Example 2: Identification of Mutations Stabilizing Lys68 Endolysin

The inventor tested whether a polypeptide comprising SEQ ID NO:120 and further sequence elements would tolerate mutations in said sequence of SEQ ID NO:120 (i.e. not leading to a loss of function), which ideally exhibit in addition a positive effect on polypeptide stability.

Briefly, the following experiment was carried out: The purified variants of Lys68 were incubated in 20 mM HEPES pH 7.4 and 500 mM NaCl at given temperatures for 20 min. Subsequently, the protein solutions were cooled down to 4° C. and the minimal inhibitory concentration (MIC) was determined using *Salmonella* Manhattan (RKI 13-05699) cells. Therefore, exponentially growing cells with an OD600 of 0.6 are diluted 1:10 with Mueller-Hinton medium (not cation-adjusted). This bacterial solution is then further diluted 1:500 in Mueller-Hinton medium (not cation-adjusted). 180 µl of bacterial suspension are mixed with 18 µl of protein solution (20 mM HEPES pH 7.4, 500 mM NaCl) with increasing protein concentration in a 96 well plate. Additionally, EDTA is added to a final concentration of 500 µM. The 96 well plate is incubated for 18 to 20 hours at 37° C. The bacterial growth is subsequently determined in a microplate reader using a wavelength of OD600. The lowest protein concentration at which no bacterial growth is observed, is defined as the minimal inhibitory concentration (MIC).

Some of the most promising candidates identified are illustrated in the following table.

TABLE 3

| Mutation | RT | 37° C. | 39.6° C. | 42.2° C. |
|---|---|---|---|---|
| — | 10 | >45 | >45 | >45 |
| P78L | 20 | 10 | 10 | >45 |
| P78L G104D A156V | 10 | 10 | 10 | >45 |
| P78S | 10 | 10 | 10 | 10 |
| G19S P78S | 10 | 10 | 10 | 20 |
| I11V P78S | 10 | 10 | 10 | 20 |
| P78S G134C | 15 | 15 | 15 | 25 |

Table 3 indicates the minimal inhibitory concentration (MIC; µg/ml) for the various polypeptides which have been tested. ">" is intended to indicate, that the respective polypeptide did not show any inhibitory activity up to the indicated concentration. Concentrations above said value have not been tested. The position of the mutation is indicated with respect to the position in full length Lys68 (SEQ ID NO:2). The corresponding polypeptides comprise the modified Lys68 sequences according to SEQ ID NO:35, SEQ ID NO:36, SEQ ID NO:37, SEQ ID NO:38, SEQ ID NO:39, and SEQ ID NO:40, respectively. "---" represents the unmutated control.

Example 3: Preferred Embodiments of the Invention

In the following, particularly preferred embodiments of the invention are provided in items 1 to 31 below. Any aspect and particular embodiment discussed above with regard to the present invention may also be implemented in the context of the embodiments below:

1. Polypeptide comprising an amino acid sequence exhibiting at least 90% sequence identity with the sequence of SEQ ID NO:1, wherein SEQ ID NO:1 is characterized by
   X5 may be any amino acid, preferably I or V,
   X13 may be any amino acid, preferably G or S,
   X72 may be any amino acid, preferably P, L or S,
   X98 may be any amino acid, preferably G or D;
   with the proviso that the polypeptide does neither comprise the sequence according to SEQ ID NO:2, nor the sequence according to SEQ ID NO:3, nor the sequence according to SEQ ID NO:4.
2. The polypeptide according to item 1, wherein the polypeptide comprises an amino acid sequence exhibiting at least about 80% sequence identity with the sequence of SEQ ID NO: 9, wherein SEQ ID NO: 9 is characterized by
   X1 may be absent or any amino acid, in particular M,
   X11 may be any amino acid, preferably I or V, X19 may be any amino acid, preferably G or S,
X78 may be any amino acid, preferably P, L or S,
X104 may be any amino acid, preferably G or D,
X134 may be any amino acid, preferably G or C; and
X156 may be any amino acid, preferably A or V.

3. Polypeptide according to item 2, wherein at least one of the following applies:
X1 of SEQ ID NO: 9 is absent or M,
X11 of SEQ ID NO: 9 is I or V,
X19 of SEQ ID NO: 9 is G or S,
X78 of SEQ ID NO: 9 is P, L or S,
X104 of SEQ ID NO: 9 is G or D,
X134 of SEQ ID NO: 9 is G or C, and/or
X156 of SEQ ID NO: 9 is A or V.

4. Polypeptide according to item 2 or item 3, wherein the following applies:
X1 of SEQ ID NO: 9 is absent or M,
X11 of SEQ ID NO: 9 is I or V,
X19 of SEQ ID NO: 9 is G or S,
X78 of SEQ ID NO: 9 is P, L or S,
X104 of SEQ ID NO: 9 is G or D,
X134 of SEQ ID NO: 9 is G or C, and
X156 of SEQ ID NO: 9 is A or V.

5. Polypeptide according to any one of items 2 to 4, wherein at least one of the following applies:
X1 of SEQ ID NO: 9 is M,
X11 of SEQ ID NO: 9 is V,
X19 of SEQ ID NO: 9 is S,
X78 of SEQ ID NO: 9 is L or S,
X104 of SEQ ID NO: 9 is D,
X134 of SEQ ID NO: 9 is C and/or
X156 of SEQ ID NO: 9 is V.

6. The polypeptide according to any one of items 2 to 5, wherein the polypeptide exhibits in the amino acid sequence exhibiting at least about 80% sequence identity with the sequence of SEQ ID NO: 9 a glutamate residue (E) at the position corresponding to position 18 of SEQ ID NO: 9.

7. The polypeptide according to any one of items 2 to 6, wherein the amino acid sequence exhibiting at least 80% sequence identity with the sequence of SEQ ID NO: 9 exhibits at least 85%, at least 90%, at least 95%, at least 96%, at least 97%, at least 98%, at least 99%, at least 99.5% or even 100% sequence identity with the sequence of SEQ ID NO: 9.

8. The polypeptide according to any one of items 2 to 7, wherein the polypeptide comprises the sequence of SEQ ID NO: 9.

9. The polypeptide according to any one of items 2 to 8, wherein X11 of SEQ ID NO: 9 is V.

10. The polypeptide according to any one of items 2 to 9, wherein X19 of SEQ ID NO: 9 is S.

11. The polypeptide according to any one of items 2 to 10, wherein X104 of SEQ ID NO: 9 is D.

12. The polypeptide according to any one of items 2 to 11, wherein X134 of SEQ ID NO: 9 is C.

13. The polypeptide according to any one of items 2 to 12, wherein X156 of SEQ ID NO: 9 is V.

14. The polypeptide according to any one of items 2 to 13, wherein X78 of SEQ ID NO: 9 is L.

15. The polypeptide according to item 14, wherein X104 of SEQ ID NO: 9 is D.

16. The polypeptide according to item 15, wherein X156 of SEQ ID NO: 9 is V.

17. The polypeptide according to any one of items 2 to 13, wherein X78 of SEQ ID NO: 9 is S.

18. The polypeptide according to item 17, wherein X19 of SEQ ID NO: 9 is S.

19. The polypeptide according to item 17 or 18, wherein X11 of SEQ ID NO: 9 is V.

20. The polypeptide according to any one of items 17 to 19, wherein X134 of SEQ ID NO: 9 is C.

21. The polypeptide according to any one of items 2 to 20, wherein X1 of SEQ ID NO: 9 is not M.

22. The polypeptide according to item 1, wherein the polypeptide comprises a sequence selected from the group consisting of SEQ ID NO: SEQ ID NO:32, SEQ ID NO:33, SEQ ID NO:34, SEQ ID NO:35, SEQ ID NO:36, SEQ ID NO:37, SEQ ID NO:38, SEQ ID NO:39, and SEQ ID NO:40.

23. The polypeptide according to any one of the preceding items, wherein the polypeptide is capable of degrading the peptidoglycan of *Salmonella* bacteria.

24. The polypeptide according to any one of the preceding items, wherein the polypeptide comprises additionally at least one amino acid sequence stretch selected from the group consisting of amphiphatic peptide, cationic peptide, polycationic peptide, hydrophobic peptide, naturally occurring antimicrobial peptide, sushi peptide and defensin, wherein said amino acid sequence stretch is preferably at the N-terminus.

25. The polypeptide according to any one of the preceding items, wherein the polypeptide comprises at least one additional amino acid sequence stretch selected from the group consisting of: KRK and SEQ ID NOs: 41-115.

26. The polypeptide according to any one of the preceding items, wherein the polypeptide has an overall length not exceeding 300 amino acids.

27. Nucleic acid encoding a polypeptide according to any one of items 1 to 26.

28. Vector comprising a nucleic acid according to item 27.

29. Host cell comprising a polypeptide according to any one of items 1 to 26, a nucleic acid according to item 27, and/or a vector according to item 28.

30. Composition comprising a polypeptide according to any one of items 1 to 26, a nucleic acid according to item 27, a vector according to item 28 and/or a host cell according to item 29.

31. Composition according to item 30, wherein the composition is a pharmaceutical composition comprising a pharmaceutical acceptable diluent, excipient or carrier.

The invention claimed is:

1. A polypeptide comprising the amino acid sequence of SEQ ID NO:1, wherein SEQ ID NO:1 is characterized by:
    X5 may be any amino acid,
    X13 may be any amino acid,
    X72 may be L or S,
    X98 may be any amino acid;
    with the proviso that the polypeptide does neither comprise the sequence according to SEQ ID NO:2, nor the sequence according to SEQ ID NO:3, nor the sequence according to SEQ ID NO:4.

2. The polypeptide according to claim 1, wherein the polypeptide comprises the amino acid sequence of SEQ ID NO: 9, wherein SEQ ID NO: 9 is characterized by:
    X1 may be absent or any amino acid,
    X11 may be any amino acid,
    X19 may be any amino acid,
    X78 may be L or S,
    X104 may be any amino acid,
    X134 may be any amino acid, and
    X156 may be any amino acid.

3. The polypeptide according to claim 2, wherein at least one of the following applies:
    X1 of SEQ ID NO: 9 is absent or M,
    X11 of SEQ ID NO: 9 is I or V,
    X19 of SEQ ID NO: 9 is G or S,
    X104 of SEQ ID NO: 9 is G or D,
    X134 of SEQ ID NO: 9 is G or C, and/or
    X156 of SEQ ID NO: 9 is A or V.

4. The polypeptide according to claim 2, wherein the following applies:
    X1 of SEQ ID NO: 9 is absent or M,
    X11 of SEQ ID NO: 9 is I or V,
    X19 of SEQ ID NO: 9 is G or S,
    X104 of SEQ ID NO: 9 is G or D,
    X134 of SEQ ID NO: 9 is G or C, and
    X156 of SEQ ID NO: 9 is A or V.

5. The polypeptide according to claim 2, wherein at least one of the following applies:
    X1 of SEQ ID NO: 9 is M,
    X11 of SEQ ID NO: 9 is V,
    X19 of SEQ ID NO: 9 is S,
    X104 of SEQ ID NO: 9 is D,
    X134 of SEQ ID NO: 9 is C and/or
    X156 of SEQ ID NO: 9 is V.

6. The polypeptide according to claim 2, wherein X1 of SEQ ID NO: 9 is not M.

7. The polypeptide according to claim 1, wherein the polypeptide comprises a sequence selected from the group consisting of SEQ ID NO:35, SEQ ID NO:36, SEQ ID NO:37, SEQ ID NO:38, SEQ ID NO:39, and SEQ ID NO:40.

8. The polypeptide according to claim 2, wherein the polypeptide is capable of degrading the peptidoglycan of *Salmonella* bacteria.

9. The polypeptide according to claim 2, wherein the polypeptide comprises additionally at least one amino acid sequence stretch selected from the group consisting of amphipathic peptide, cationic peptide, polycationic peptide, hydrophobic peptide, naturally occurring antimicrobial peptide, sushi peptide and defensin.

10. The polypeptide according to claim 2, wherein the polypeptide comprises at least one additional amino acid sequence stretch selected from the group consisting of: KRK and SEQ ID NOs: 41-115.

11. The polypeptide according to claim 2, wherein the polypeptide has an overall length not exceeding 300 amino acids.

12. A composition comprising a polypeptide according to claim 1.

13. A composition according to claim 12, wherein the composition is a pharmaceutical composition comprising a pharmaceutical acceptable diluent, excipient or carrier.

14. The polypeptide according to claim 9, wherein said amino acid sequence stretch is at the N-terminus.

* * * * *